(12) United States Patent
Lewin et al.

(10) Patent No.: US 11,384,071 B2
(45) Date of Patent: Jul. 12, 2022

(54) INHIBITORS OF MECHANOTRANSDUCTION TO TREAT PAIN AND MODULATE TOUCH PERCEPTION

(71) Applicant: Max-Delbrück-Centrum für Molekulare Medizin in der Helmholtz-Gemeinschaft, Berlin (DE)

(72) Inventors: Gary Richard Lewin, Berlin (DE); Kathryn Anne Poole, Coogee (AU); Christiane Wetzel, Berlin (DE); Liudmila Lapatsina, Berlin (DE)

(73) Assignee: MAX-DELBRÜCK-CENTRUM FÜR MOLEKULARE MEDIZIN IN DER HELMHOLTZ-GEMEINSCHAFT, Berlin (DE)

(*) Notice: Subject to any disclaimer, the term of this patent is extended or adjusted under 35 U.S.C. 154(b) by 154 days.

(21) Appl. No.: 16/466,907

(22) PCT Filed: Dec. 7, 2017

(86) PCT No.: PCT/EP2017/081895
§ 371 (c)(1),
(2) Date: Jun. 5, 2019

(87) PCT Pub. No.: WO2018/104479
PCT Pub. Date: Jun. 14, 2018

(65) Prior Publication Data
US 2019/0382386 A1    Dec. 19, 2019

(30) Foreign Application Priority Data
Dec. 7, 2016 (EP) .................................. 16202753

(51) Int. Cl.
*C07D 405/12* (2006.01)
*A61K 9/00* (2006.01)
*A61K 31/53* (2006.01)
*C07D 417/12* (2006.01)
*A61P 25/04* (2006.01)

(52) U.S. Cl.
CPC .......... *C07D 405/12* (2013.01); *A61K 9/0014* (2013.01); *A61K 31/53* (2013.01); *A61P 25/04* (2018.01); *C07D 417/12* (2013.01)

(58) Field of Classification Search
None
See application file for complete search history.

(56) References Cited

U.S. PATENT DOCUMENTS

2015/0297602 A1    10/2015    Lambert et al.

OTHER PUBLICATIONS

Chemical Abstracts Database Registry, Registration No. 300689-25-2, Nov. 1, 2000.
Chemical Abstracts Database Registry, Registration No. 300803-69-4, Nov. 2, 2000.
Picci, C. 2014 "Exploitation of new pharmacological targets for neuropathic pain relief" Universita Degli Studi Di Cagliari Dottorato Di Recerca in Scienze morfologiche E Funzionali XXFII CICLO, (in 78 pages).
Wetzel, C. et al. 2017 "Small-molecule inhibition of STOML3 oligomerization reverses pathological mechanical hypersensitivity" Nature Neuroscience 20: 209-218, also including Online Methods (in 3 pages).
Yadav, P. et al. 2014 "Design, synthesis, docking and anti-inflammatory evaluation of novel series of benzofuran based prodrugs" *Bioorganic & Medicinal Chemistry Letters* 24: 2251-2255.

*Primary Examiner* — Savitha M Rao
*Assistant Examiner* — Gregg Polansky
(74) *Attorney, Agent, or Firm* — Knobbe, Martens, Olson & Bear, LLP

(57) ABSTRACT

Chemical compounds that are useful as inhibitors of mechanotransduction in the treatment of pain and modulation of touch perception and topical administration of the compounds described herein in the treatment of pain and modulation of touch perception.

24 Claims, 22 Drawing Sheets a b c d a b c

INHIBITORS OF MECHANOTRANSDUCTION TO TREAT PAIN AND MODULATE TOUCH PERCEPTION

FIELD

The invention relates to chemical compounds that are useful as inhibitors of mechanotransduction in the treatment of pain and modulation of touch perception. The invention further relates to the topical administration of the compounds described herein in the treatment of pain and modulation of touch perception.

BACKGROUND

All skin sensation starts with the transformation of a physical stimulus into an electrical signal called a receptor potential. The receptor potential is encoded as action potentials (AP), which convey information to the brain to initiate perception[1]. Pharmacological agents that modulate the first step in the transformation of light touch stimuli into an electrical signal, a process called sensory mechanotransduction, are currently not available.

The mechanosensitive ion channel Piezo2 and its modulator STOML3[2] have both been shown to be necessary for mechanoreceptors to transduce light touch[3-6]. Paradoxically, under pathophysiological conditions, intense pain can also be triggered by light touch[7,8], for example after traumatic nerve injury[9]. Nerve injury induced touch-evoked pain was found to be largely absent in Stoml3$^{-/-}$ mutant mice[6]. STOML3 is an endogenous regulator of the sensitivity of mechanosensitive ion channels like Piezo in sensory neurons and STOML3 self-association appears to be necessary for this function[10,11].

In light of the prior art there remains a significant need in the art to provide additional means for the inhibition of mechanotransduction, for the treatment of pain and modulation of touch perception.

SUMMARY

The present invention provides compounds capable of disrupting STOML3 self-association and function, and can be used to treat pain, in particular tactile-induced pain and modulate touch receptor function under normal and pathophysiological conditions.

The stomatin-domain of STOML3 protein is necessary for the normal function of this protein in maintaining the mechanosensitivity of touch receptors of the skin. The present invention provides small molecules that inhibit stomatin-domain oligomerization and block touch receptor function. The blockade of touch and pain receptors is an effective strategy to treat neuropathic and inflammatory pain. The inventors demonstrate that the compounds described herein exert antagonism of STOML3 function as a result of their binding to a specific inter-molecular interface that mediates self-association of STOML3. The compounds can block the mechanotransduction and the mechanosensitivity of sensory afferents. The compounds described herein are an example of a novel chemical strategy to treat a wide variety of painful conditions including neuropathic and inflammatory pain.

The present invention therefore relates to small molecule inhibitors of STOML3 oligomerization. The inhibitors reversibly reduce the sensitivity of mechanically-gated currents in sensory neurons and silence mechanoreceptors. The STOML3 inhibitors described herein are capable of reversibly attenuating touch perception in the skin of subjects.

Under pathophysiological conditions, for example following nerve injury or diabetic neuropathy, the slightest touch can evoke intense pain, and under these conditions it is herein demonstrated that STOML3 inhibitors can reverse mechanical hypersensitivity. Thus, the compounds of the present invention may be administered, either systemically or preferably locally, for example to the skin or other mucosal surface of a subject, in order to specifically modulate touch and/or sensory perception. The compounds described herein represent means of treating preferably tactile-driven pain, such as in neuropathic pain, in addition to means for the modulation of touch perception in a subject.

Neuropathic pain is typically very difficult to treat and the leading medication that has and is being used in the clinic is gabapentin and pregabalin (LYRICA™). This drug has efficacy in treating the severe symptoms of neuropathic pain but only in a small subset of patients. This drug is thought to act by modulating calcium channels in the pre-synaptic terminals of sensory afferents within the spinal cord. The CNS site of action of this drug is associated with a variety of side effects of central nervous system origin.

Drugs acting to inhibit mechanotransduction in the periphery have the advantage that they do not have to penetrate the CNS to have efficacy. The treatment as described by the present invention is predicted to be symptomatic in the sense that it is the peripheral activation of mechanoreceptors and pain receptors that always triggers symptoms. By reducing such signals the present invention enables an effective symptomatic treatment. The pathophysiological origin of neuropathic pain is extremely diverse, which means that a treatment aimed at the symptoms (mechanical stimulation triggers activation of sensory fibers that initiate pain) has a high chance of success in any neuropathic pain patient regardless of the pathophysiological origin of the disorder. The compounds of the invention therefore are capable of reducing side effects compared to centrally acting compounds due to their local site of action in the periphery.

The compounds of the present invention according to Formulae I-IX, and in particular according to OB-1, OB-2, MDC-D38, MDC-D30 and MDC-D33 represent effective means in the treatment of pain and modulation of touch perception. Despite any structural differences in the compounds described herein, the compounds of the invention represent unitary subject matter, as they are all defined by the common characteristic of a small-molecule mechanotransduction inhibitor directly effecting STOML3 oligomerization and function. To the knowledge of the inventors, at the present time, no effective small molecule inhibitors of this nature are known in the art. The common mechanistic and/or functional features of the compounds described herein are novel and entirely unexpected. Common structural elements of the compounds according to Formulae I-IX in the context of their function in treatment of pain and modulation of touch perception also represent potentially unifying features.

Compounds of similar structure to Formula I have been previously disclosed as anti-inflammatory agents (Pratima et al, Bioorganic & Medicinal Chemistry Letters, 2014, vol. 24, no. 10, p 2251-2255). Compounds of similar structure to Formula III have been previously disclosed as means for inhibiting HPV viral infections (US 2015/0297602). No suggestion is evident in the art that the compounds described herein may be suitable for the treatment of pain and modulation of touch perception.

In light of the prior art the technical problem underlying the present invention is to provide alternative and/or improved means for the treatment of pain and/or for the modulation of touch perception.

This problem is solved by the features of the independent claims. Preferred embodiments of the present invention are provided by the dependent claims.

The invention therefore relates to a compound for use as a medicament in the treatment of pain according to Formula I,

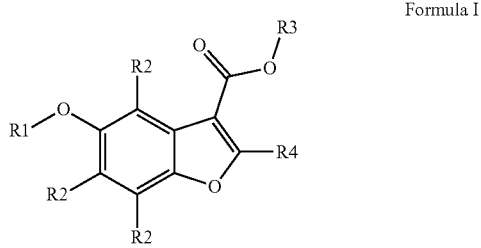

Formula I wherein

R1=5-membered aromatic heterocycle, comprising one or more of N, O and/or S, optionally substituted with $Y_x$, wherein x=0, 1, 2, 3, wherein Y can be the same or different, and wherein Y is nitro, halogen (preferably Br, Cl or F), C1-C7 (preferably C1-C5 or C1-C3) alkyl, alkoxy, optionally substituted with halogen (preferably Br, Cl or F);

R2=can be the same or different, H, halogen (preferably Br, Cl or F), C1-C7 (preferably C1-C5 or C1-C3) alkyl, alkoxy;

R3=H, C1-C7 (preferably C1-C5 or C1-C3) alkyl, cycloalkyl, alkoxy, aryl, optionally substituted with one or more halogens (preferably Br, Cl or F);

R4=H, C1-C7 (preferably C1-C5 or C1-C3) alkyl, cycloalkyl, alkoxy, aryl, optionally substituted with one or more halogens (preferably Br, Cl or F).

To the knowledge of the inventors the compounds of Formula I described above have not been previously described in the context of pain treatment. The compounds encompassed by Formula I are structurally related to the compound OB-1, which has been demonstrated to be an inhibitor of both mouse and human STOML3-oligomerization and function, and is an inhibitor of mechanosensitive currents, thereby enabling pain treatment and modulation of touch perception in subjects. To the knowledge of the inventors no suggestion is evident in the art that the compounds according to Formula I would exhibit such properties.

In a preferred embodiment, the invention relates to a compound for use as a medicament according to Formula I (embodiment I-a),

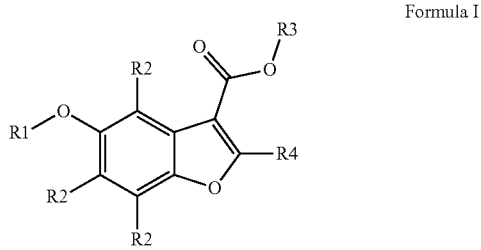

Formula I wherein

R1=5-membered aromatic heterocycle, comprising 1-2 N atoms, optionally substituted with $Y_x$, wherein x=0, 1, 2, 3, wherein Y can be the same or different, and wherein Y is nitro, halogen (preferably Br, Cl or F), C1-C7 (preferably C1-C5 or C1-C3) alkyl, optionally substituted with halogen (preferably Br, Cl or F);

R2=H,

R3=H, C1-C7 (preferably C1-C5 or C1-C3) alkyl, optionally substituted with one or more halogens (preferably Br, Cl or F), R4=H, C1-C7 (preferably C1-C5 or C1-C3) alkyl, cycloalkyl, aryl, optionally substituted with one or more halogens (preferably Br, Cl or F).

The above-mentioned embodiment I-a represents a preferred set of substituents for each of R1 to R4 for Formula I. In some embodiments of the invention, for any embodiment of Formula I, the C1-C7 alkyl, cycloalkyl and/or alkoxy substituents, for example all of said groups of the embodiment, preferably alkyl, is C1-C5, or C1-C3, whereby the remaining substituents of the embodiment remain as described above. Without being bound to theory, if steric restrictions are in some embodiments to be considered, the smaller side chains may be preferred. In further embodiments, for any embodiment of Formula I, one or more halogens, for example all halogens of the embodiment, is Br, Cl or F, whereby the remaining substituents of the embodiment remain as described above. In one embodiment of Formula I aryl is phenyl, whereby the remaining substituents of the embodiment remain as described above. In one embodiment of Formula I the aryl substituent may exhibit more than 7 C atoms, whereby the remaining substituents of the embodiment remain as described above.

In one embodiment, the invention relates to a compound for use as a medicament according to the preceding claim, according to Formula II,

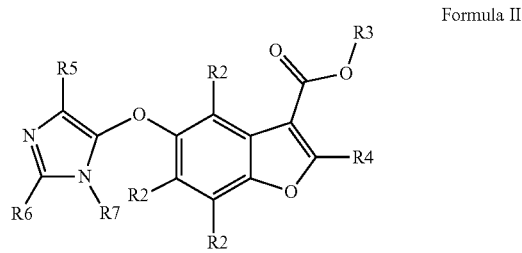

Formula II wherein

R2=can be the same or different, H, halogen (preferably Br, Cl or F), C1-C7 (preferably C1-C5 or C1-C3) alkyl, alkoxy;

R3=H, C1-C7 (preferably C1-C5 or C1-C3) alkyl, cycloalkyl, alkoxy, aryl, optionally substituted with one or more halogens (preferably Br, Cl or F);

R4=H, C1-C7 (preferably C1-C5 or C1-C3) alkyl, cycloalkyl, alkoxy, aryl, optionally substituted with one or more halogens (preferably Br, Cl or F);

R5=H, nitro, halogen (preferably Br, Cl or F), C1-C7 (preferably C1-C5 or C1-C3) alkyl, cycloalkyl, alkoxy, optionally substituted with one or more halogens (preferably Br, Cl or F);

R6=H, halogen (preferably Br, Cl or F), C1-C7 (preferably C1-C5 or C1-C3) alkyl, cycloalkyl, alkoxy, optionally substituted with one or more halogens (preferably Br, Cl or F);

R7=H, C1-C7 (preferably C1-C5 or C1-C3) alkyl, cycloalkyl, optionally substituted with one or more halogens (preferably Br, Cl or F).

The compounds encompassed by Formula II are structurally related to the compound OB-1, which has been demonstrated to be an inhibitor of both mouse and human STOML3-oligomerization and function, and is an inhibitor of mechanosensitive currents, thereby enabling pain treatment and modulation of touch perception in subjects. There appears to be no suggestion in the art that the compounds of Formula II, similar to those of Formula I but characterized by the 5-membered heterocycle in position R1 of Formula I, would exhibit the desired properties.

In a preferred embodiment, the invention relates to a compound for use as a medicament according to Formula II (embodiment II-a),

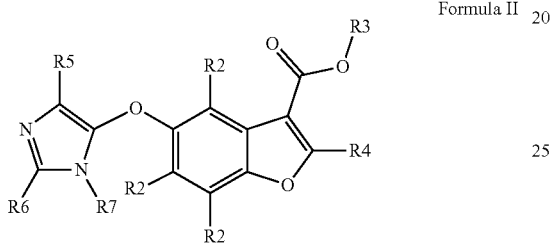

Formula II wherein
R2=H,
R3=H, C1-C7 (preferably C1-C5 or C1-C3) alkyl, optionally substituted with one or more halogens (preferably Br, Cl or F),
R4=H, C1-C7 (preferably C1-C5 or C1-C3) alkyl, cycloalkyl, aryl, optionally substituted with one or more halogens (preferably Br, Cl or F).
R5=H, nitro, halogen (preferably Br, Cl or F), C1-C7 (preferably C1-C5 or C1-C3) alkyl, optionally substituted with one or more halogens (preferably Br, Cl or F), most preferably nitro;
R6=H, halogen (preferably Br, Cl or F), C1-C7 (preferably C1-C5 or C1-C3) alkyl, optionally substituted with one or more halogens (preferably Br, Cl or F);
R7=H, C1-C7 (preferably C1-C5 or C1-C3) alkyl, optionally substituted with one or more halogens (preferably Br, Cl or F).

The above-mentioned embodiment II-a represents a preferred set of substituents for each of R2 to R7 for Formula II. In some embodiments of the invention, for any embodiment of Formula II, the C1-C7 alkyl, cycloalkyl and/or alkoxy substituents, for example all of said groups of the embodiment, preferably alkyl, is C1-C5, or C1-C3, whereby the remaining substituents of the embodiment remain as described above. Without being bound to theory, if steric restrictions are in some embodiments to be considered, the smaller side chains may be preferred. In further embodiments, for any embodiment of Formula II, one or more halogens, for example all halogens of the embodiment, is Br, Cl or F, whereby the remaining substituents of the embodiment remain as described above. In one of Formula II embodiment aryl is phenyl, whereby the remaining substituents of the embodiment remain as described above. In one embodiment of Formula II the aryl substituent may exhibit more than 7 C atoms, whereby the remaining substituents of the embodiment remain as described above.

For the purpose of the present invention the following features in combination with any one of the above embodiments of Formula I or II are preferred, or in some embodiments any given two or more of the following features may be combined, preferably with the remaining substituents as described above for any given embodiment of Formula I or II, in order to arrive at embodiments of the subject matter of the present invention:

In a preferred embodiment of Formula I as described herein, the 5-membered aromatic heterocycle of R1 is an optionally substituted imidazole group, whereby the remaining substituents are preferably as described above for any embodiment of Formula I;

In a preferred embodiment of Formula I and/or Formula II as described herein, Substituent Y of Formula I or R5, R6 and R7 of Formula II comprise at least one nitro substituent, whereby the remaining substituents are preferably as described for Formula I or II as above;

In a preferred embodiment of Formula I and/or Formula II as described herein, Substituent Y of Formula I or R5, R6 and R7 of Formula II comprise at least one nitro substituent, one C1 alkyl and one H, whereby the remaining substituents are preferably as described for Formula I or II as above;

In a preferred embodiment of Formula II as described herein, R5 is nitro, whereby the remaining substituents are preferably as described for Formula II as above;

In a preferred embodiment of Formula II as described herein, R5 is nitro, R7 is $CH_3$, and R6 is preferably H, whereby the remaining substituents are preferably as described for Formula II as above;

In a preferred embodiment of Formulae I as described herein, R2 is H, whereby the remaining substituents are preferably as described in Formula I above;

In a preferred embodiment of Formula I and/or Formula II as described herein, R3 is C1-C7, C1-C5 or C1, C2 or C3, preferably C2 alkyl, whereby the remaining substituents are preferably as described in Formula I and/or II above; and/or In a preferred embodiment of Formula I and/or Formula II as described herein, R4 is C1-C7 cycloalkyl or phenyl, preferably C6 cycloalkyl or phenyl, more preferably phenyl, whereby the remaining substituents are preferably as described in Formula I and/or II above.

In one embodiment of the invention the compound of Formula I or II is:

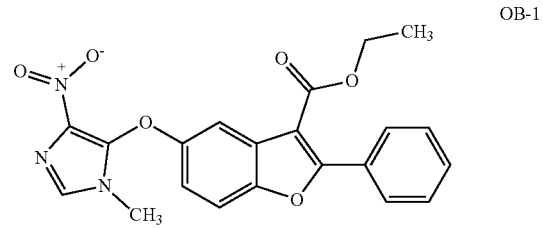

OB-1

A further aspect of the invention relates to a compound, preferably for use as a medicament as disclosed herein, according to Formula V:

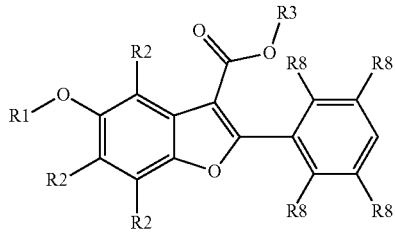

Formula V wherein
R1=5-membered aromatic heterocycle, comprising one or more of N, O and/or S, optionally substituted with Yx, wherein x=0, 1, 2, 3, wherein Y can be the same or different, and wherein Y is nitro, halogen (preferably Br, Cl or F), C1-C7 (preferably C1-C5 or C1-C3) alkyl, alkoxy, optionally substituted with halogen (preferably Br, Cl or F);

R2=can be the same or different, H, halogen (preferably Br, Cl or F), C1-C7 (preferably C1-C5 or C1-C3) alkyl, alkoxy;

R3=H, C1-C7 (preferably C1-C5 or C1-C3) alkyl, cycloalkyl, alkoxy, aryl, optionally substituted with one or more halogens (preferably Br, Cl or F);

R8=can be the same or different, H, halogen (preferably Cl), wherein at least one of R8 is halogen.

In one embodiment, the compound of Formula V is characterized by the following substituents:

R1=5-membered aromatic heterocycle, comprising 1-2 N atoms, optionally substituted with Yx, wherein x=0, 1, 2, 3, wherein Y can be the same or different, and wherein Y is nitro, halogen (preferably Br, Cl or F), C1-C7 (preferably C1-C5 or C1-C3) alkyl, optionally substituted with halogen (preferably Br, Cl or F);

R2=H,

R3=H, C1-C7 (preferably C1-C5 or C1-C3) alkyl, optionally substituted with one or more halogens (preferably Br, Cl or F), R8=can be the same or different, H, halogen (preferably Cl), wherein at least one of R8 is halogen.

A further aspect of the invention relates to a compound, preferably for use as a medicament as disclosed herein, according to Formula VI:

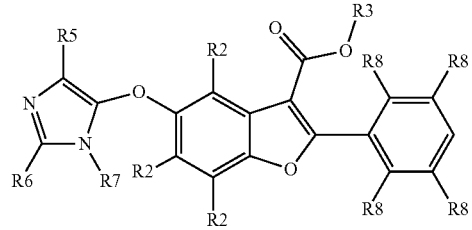

Formula VI wherein
R2=can be the same or different, H, halogen (preferably Br, Cl or F), C1-C7 (preferably C1-C5 or C1-C3) alkyl, alkoxy;

R3=H, C1-C7 (preferably C1-C5 or C1-C3) alkyl, cycloalkyl, alkoxy, aryl, optionally substituted with one or more halogens (preferably Br, Cl or F);

R5=H, nitro, halogen (preferably Br, Cl or F), C1-C7 (preferably C1-C5 or C1-C3) alkyl, cycloalkyl, alkoxy, optionally substituted with one or more halogens (preferably Br, Cl or F);

R6=H, halogen (preferably Br, Cl or F), C1-C7 (preferably C1-C5 or C1-C3) alkyl, cycloalkyl, alkoxy, optionally substituted with one or more halogens (preferably Br, Cl or F);

R7=H, C1-C7 (preferably C1-C5 or C1-C3) alkyl, cycloalkyl, optionally substituted with one or more halogens (preferably Br, Cl or F), R8=can be the same or different, H, halogen (preferably Cl), wherein at least one of R8 is halogen.

In one embodiment, the compound of Formula VI is characterized by the following substituents:

R2=H,

R3=H, C1-C7 (preferably C1-C5 or C1-C3) alkyl, optionally substituted with one or more halogens (preferably Br, Cl or F), R5=H, nitro, halogen (preferably Br, Cl or F), C1-C7 (preferably C1-C5 or C1-C3) alkyl, optionally substituted with one or more halogens (preferably Br, Cl or F), most preferably nitro;

R6=H, halogen (preferably Br, Cl or F), C1-C7 (preferably C1-C5 or C1-C3) alkyl, optionally substituted with one or more halogens (preferably Br, Cl or F);

R7=H, C1-C7 (preferably C1-C5 or C1-C3) alkyl, optionally substituted with one or more halogens (preferably Br, Cl or F), R8=can be the same or different, H, halogen (preferably Cl), wherein at least one of R8 is halogen.

A further aspect of the invention relates to a compound, preferably for use as a medicament as disclosed herein, according to Formula VII:

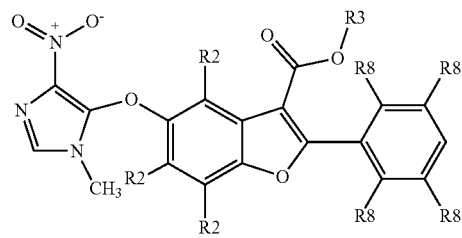

Formula VII wherein
R2=can be the same or different, H, halogen (preferably Br, Cl or F), C1-C7 (preferably C1-C5 or C1-C3) alkyl, alkoxy;

R3=H, C1-C7 (preferably C1-C5 or C1-C3) alkyl, cycloalkyl, alkoxy, aryl, optionally substituted with one or more halogens (preferably Br, Cl or F);

R8=can be the same or different, H, halogen (preferably Cl), wherein at least one of R8 is halogen.

In one embodiment, the compound of Formula VII is characterized by the following substituents:

R2=H,

R3=H, C1-C7 (preferably C2) alkyl,

R8=can be the same or different, H, halogen (preferably Cl), wherein at least one of R8 is halogen.

A further aspect of the invention relates to a compound, preferably for use as a medicament as disclosed herein, according to Formula I:

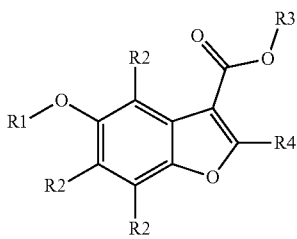

Formula I wherein
R1=5-membered aromatic heterocycle, comprising at least one N and at least one S (preferably one N and one S), optionally substituted with Y$_x$, wherein x=0, 1, 2, 3, wherein Y can be the same or different, and wherein Y is nitro, halogen (preferably Br, Cl or F), C1-C7 (preferably C1-C5 or C1-C3) alkyl, alkoxy, optionally substituted with halogen (preferably Br, Cl or F);
R2=can be the same or different, H, halogen (preferably Br, Cl or F), C1-C7 (preferably C1-C5 or C1-C3) alkyl, alkoxy;
R3=H, C1-C7 (preferably C1-C5 or C1-C3) alkyl, cycloalkyl, alkoxy, aryl, optionally substituted with one or more halogens (preferably Br, Cl or F);
R4=H, C1-C7 (preferably C1-C5 or C1-C3) alkyl, cycloalkyl, alkoxy, aryl, optionally substituted with one or more halogens (preferably Br, Cl or F).

In one embodiment, the compound of Formula I is characterized by the following substituents:
R1=5-membered aromatic heterocycle, comprising one N and one S,
R2=H,
R3=H, C1-C7 (preferably C1-C5 or C1-C3) alkyl, optionally substituted with one or more halogens (preferably Br, Cl or F),
R4=aryl, optionally substituted with one or more halogens (preferably Br, Cl or F).

A further aspect of the invention relates to a compound, preferably for use as a medicament as disclosed herein, according to Formula VIII:

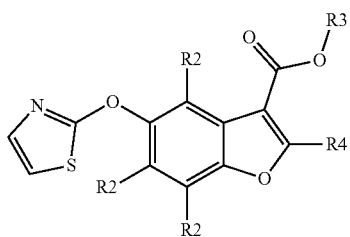

Formula VIII wherein
R2=can be the same or different, H, halogen (preferably Br, Cl or F), C1-C7 (preferably C1-C5 or C1-C3) alkyl, alkoxy;
R3=H, C1-C7 (preferably C1-C5 or C1-C3) alkyl, cycloalkyl, alkoxy, aryl, optionally substituted with one or more halogens (preferably Br, Cl or F);
R4=H, C1-C7 (preferably C1-C5 or C1-C3) alkyl, cycloalkyl, alkoxy, aryl, optionally substituted with one or more halogens (preferably Br, Cl or F).

In one embodiment, the compound of Formula VIII is characterized by the following substituents:
R2=H,
R3=H, C1-C7 (preferably C1-C5 or C1-C3) alkyl, optionally substituted with one or more halogens (preferably Br, Cl or F),
R4=H, C1-C7 (preferably C1-C5 or C1-C3) alkyl, cycloalkyl, aryl, optionally substituted with one or more halogens (preferably Br, Cl or F).

A further aspect of the invention relates to a compound, preferably for use as a medicament as disclosed herein, according to Formula IX:

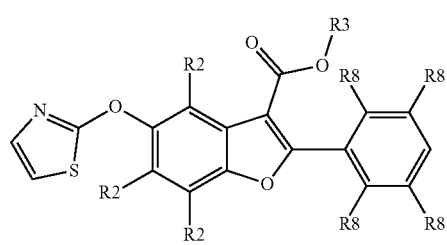

Formula IX wherein
R2=can be the same or different, H, halogen (preferably Br, Cl or F), C1-C7 (preferably C1-C5 or C1-C3) alkyl, alkoxy;
R3=H, C1-C7 (preferably C1-C5 or C1-C3) alkyl, cycloalkyl, alkoxy, aryl, optionally substituted with one or more halogens (preferably Br, Cl or F);
R8=can be the same or different, H, halogen (preferably Cl), preferably wherein at least one of R8 is halogen.

In one embodiment, the compound of Formula IX is characterized by the following substituents:
R2=H,
R3=H, C1-C7 (preferably C1-C5 or C1-C3) alkyl, optionally substituted with one or more halogens (preferably Br, Cl or F),
R8=can be the same or different, H, halogen (preferably Cl), preferably wherein at least one of R8 is halogen.

In each of formula I-II, and V-IX, R3 is preferably C2 alkyl.

In each of formula I-II, and V-IX, R2 is preferably H.

In one embodiment of the invention the compound of Formula I-II, or V-IX is:

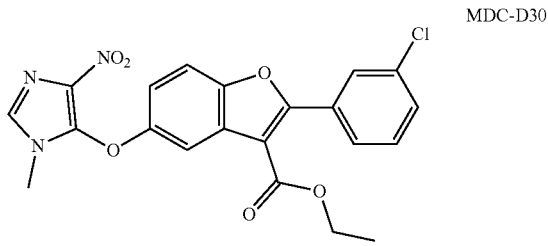 [SMILES: CCOC(=O)c1c(-c2cccc(Cl)c2)oc2ccc(Oc3c([N+](=O)[O-])ncn3C)cc12]

MDC-D30

In one embodiment of the invention the compound of Formula I-II, or V-IX is:

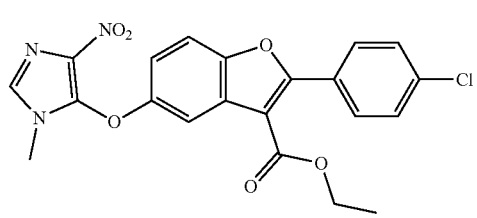

MDC-D34

In one embodiment of the invention the compound of Formula I-II, or V-IX is:

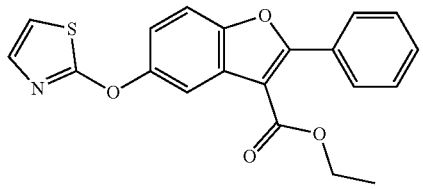

MDC-D38

The invention further relates to the compounds of Formulae I-IX, as described herein, for example OB-1, OB-2, MDC-D30, MDC-D34, MDC-D38, for use as a medicament in the treatment of pain, or for use in a method for modulation of touch perception.

A further aspect of the invention relates to a compound for use as a medicament in the treatment of pain according to Formula III,

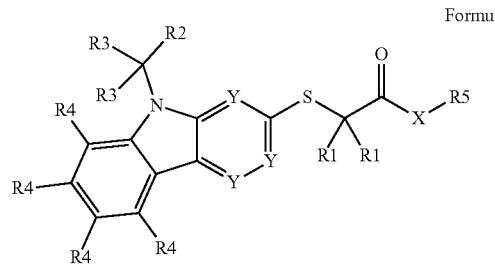

Formula III wherein
X=NR6, wherein R6 is H, C1-C7 (preferably C1-C5 or C1-C3) alkyl, alkoxy, optionally substituted with one or more halogens (preferably Br, Cl or F);
R1=can be the same or different, H, C1-C7 (preferably C1-C5 or C1-C3) alkyl, optionally substituted with one or more halogens (preferably Br, Cl or F);
R2=5- or 6-membered carbon ring structure, optionally aromatic, optionally substituted with $Z_x$, wherein x=0-5, wherein Z can be the same or different, and wherein Z is selected from halogen (preferably Br, Cl or F), C1-C7 (preferably C1-C5 or C1-C3) alkyl, alkoxy, wherein Z is optionally substituted with one or more halogens (preferably Br, Cl or F);
R3=can be the same or different, H, C1-C7 (preferably C1-C5 or C1-C3) alkyl, optionally substituted with one or more halogens (preferably Br, Cl or F);
R4=can be the same or different, H, halogen (preferably Br, Cl or F), C1-C7 (preferably C1-C5 or C1-C3) alkyl, alkoxy, optionally substituted with one or more halogens (preferably Br, Cl or F);
R5=6-membered aromatic heterocycle, comprising one or more of N, O and/or S, optionally substituted with $Z_x$, wherein x=0-5, wherein Z can be the same or different, and wherein Z is selected from halogen (preferably Br, Cl or F), C1-C7 (preferably C1-C5 or C1-C3) alkyl, alkoxy, wherein Z is optionally substituted with one or more halogens (preferably Br, Cl or F);
Y=C, N.

To the knowledge of the inventors the structures described above under Formulae III have not been previously described in the context of pain treatment. The compounds encompassed by Formulae III are structurally related to the compound OB-2, which has been demonstrated to be an inhibitor of STOML3-oligomerization and function, and an inhibitor of mechanosensitive currents, thereby enabling pain treatment and modulation of touch perception in subjects.

In a preferred embodiment the invention relates to a compound for use as a medicament according to Formula III (embodiment III-a),

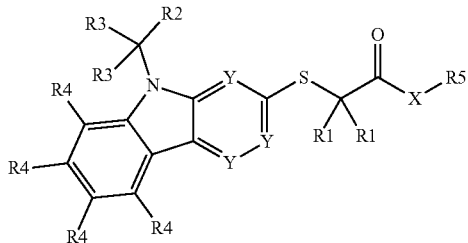

Formula III wherein
X=NR6, wherein R6 is H, C1-C7 (preferably C1-C5 or C1-C3) alkyl, optionally substituted with one or more halogens (preferably Br, Cl or F);
R1=can be the same or different, H, C1-C7 (preferably C1-C5 or C1-C3) alkyl, optionally substituted with one or more halogens (preferably Br, Cl or F);
R2=6-membered carbon ring structure,
optionally aromatic, optionally substituted with $Z_x$, wherein x=0-5, wherein Z can be the same or different, and wherein Z is selected from halogen (preferably Br, Cl or F), C1-C7 (preferably C1-C5 or C1-C3) alkyl, wherein Z is optionally substituted with one or more halogens (preferably Br, Cl or F);
R3=can be the same or different, H, C1-C7 (preferably C1-C5 or C1-C3) alkyl, optionally substituted with one or more halogens (preferably Br, Cl or F);
R4=can be the same or different, H, halogen (preferably Br, Cl or F), C1-C7 (preferably C1-C5 or C1-C3) alkyl, optionally substituted with one or more halogens (preferably Br, Cl or F);
R5=6-membered aromatic heterocycle, comprising 1 or 2 N atoms, optionally substituted with $Z_x$, wherein x=0-5, wherein Z can be the same or different, and wherein Z is selected from halogen (preferably Br, Cl or F), C1-C7 (preferably C1-C5 or C1-C3) alkyl, wherein Z is optionally substituted with one or more halogens (preferably Br, Cl or F);

Y=C, N, wherein at least one (preferably 2 or 3) Y is N.

The above mentioned embodiment III-a represents a preferred set of substituents for each of X, Y, and R1 to R5 for Formula III. In some embodiments of the invention, for any embodiment of Formula IIII, the C1-C7 alkyl, cycloalkyl and/or alkoxy substituents, for example all of said groups of the embodiment, preferably alkyl, is C1-C5, or C1-C3, whereby the remaining substituents of the embodiment remain as described above. Without being bound to theory, if steric restrictions are in some embodiments to be considered, the smaller side chains may be preferred. In further embodiments, for any embodiment of Formula III, one or more halogens, for example all halogens of the embodiment, is Br, Cl or F, whereby the remaining substituents of the embodiment remain as described above.

In a preferred embodiment the invention relates to a compound for use as a medicament according to Formula IV,

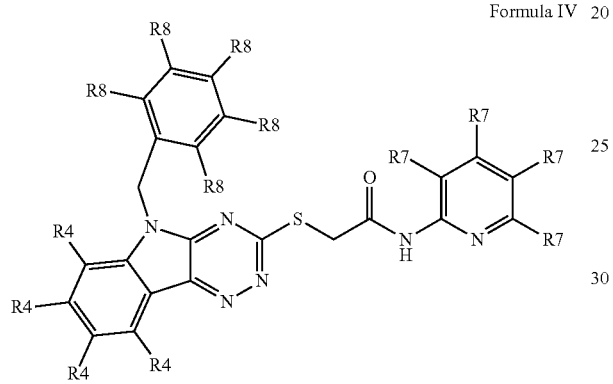

Formula IV wherein

R4=can be the same or different, H, halogen (preferably Br, Cl or F), C1-C7 (preferably C1-C5 or C1-C3) alkyl, optionally substituted with one or more halogens (preferably Br, Cl or F), wherein preferably at least 2 or 3 of R4 are H;

R7=can be the same or different, H, halogen (preferably Br, Cl or F), C1-C7 (preferably C1-C5 or C1-C3) alkyl, optionally substituted with one or more halogens (preferably Br, Cl or F), wherein preferably at least 2 or 3 of R7 are H, and preferably one of R7 is CH3;

R8=can be the same or different, H, halogen (preferably Br, Cl or F), C1-C7 (preferably C1-C5 or C1-C3) alkyl, optionally substituted with one or more halogens (preferably Br, Cl or F), wherein preferably at least 3 or 4 of R8 are H.

To the knowledge of the inventors the structures described above under Formulae IV have not been previously described in the context of pain treatment. The compounds encompassed by Formulae IV are structurally related to the compound OB-2, which has been demonstrated to be an inhibitor of STOML3-oligomerization and function, and an inhibitor of mechanosensitive currents, thereby enabling pain treatment and modulation of touch perception in subjects.

The above mentioned embodiment of Formula IV represents a preferred structure falling under Formula III. In some embodiments of the invention, for any embodiment of Formula IV, the C1-C7 alkyl, cycloalkyl and/or alkoxy substituents, for example all of said groups of the embodiment, preferably alkyl, is C1-C5, or C1-C3, whereby the remaining substituents of the embodiment remain as described above. Without being bound to theory, if steric restrictions are in some embodiments to be considered, the smaller side chains may be preferred. In further embodiments of Formula IV, one or more halogens, for example all halogens of the embodiment, is Br, Cl or F, whereby the remaining substituents of the embodiment remain as described above.

For the purpose of the present invention the following features in combination with any one of the above embodiments of Formula III or IV are preferred, or in some embodiments any given two or more of the following features may be combined, preferably with the remaining substituents as described above for any given embodiment of Formula III or IV, in order to arrive at embodiments of the subject matter of the present invention:

In a preferred embodiment of Formula III as described herein, the 5- or 6-membered carbon ring structure of R2 is an optionally substituted phenyl, whereby the remaining substituents are preferably as described above for any embodiment of Formula III;

In a preferred embodiment of Formula III substituents R1 and/or R3 are H, whereby the remaining substituents are preferably as described above for any embodiment of Formula III;

In a preferred embodiment of Formula III and/or Formula IV as described herein, substituents R4, R7 and/or R8 is H, whereby the remaining substituents are preferably as described for Formula III or IV as above;

In a preferred embodiment of Formula III as described herein, R5 is an optionally substituted pyridine ring, preferably substituted with one C1-C3 alkyl, preferably a CH3 substituent, whereby the remaining substituents are preferably as described for Formula III as above;

In a preferred embodiment of Formula IV as described herein, Substituent R4 is H, whereby the remaining substituents are preferably as described for Formula IV as above; and/or In a preferred embodiment of Formula IV as described herein, Substituent R4 is H, R8 is H and one R7 Is C1-C3 alkyl, and the remaining R7 are H, whereby the remaining substituents are preferably as described for Formula IV as above.

In one embodiment of the invention the compound of Formula III or IV is:

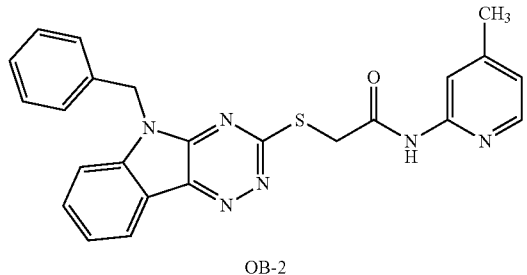 [SMILES: Cc1ccnc(NC(=O)CSc2nnc3c4ccccc4n(Cc4ccccc4)c3n2)c1 ; "OB-2"]

OB-2

The invention relates to a compound as described herein for use as a medicament in the treatment of pain. The invention therefore also relates to a method for the production of a pharmaceutical composition comprising a compound as described herein for the treatment of pain. The invention therefore also relates to a method for the treatment of pain in a subject in need thereof, comprising administration of a compound as described herein to a subject in need thereof.

As mentioned above, pharmacological agents that modulate the first step in the transformation of light touch stimuli into an electrical signal, a process called sensory mechanotransduction, are currently not available.

The compounds of the present invention according to Formulae I-IX, and in particular according to OB-1, OB-2, MDC-D38, MDC-D30 and MDC-D33, represent effective means in modulating sensory mechanotransduction, and therefore may be applied in the treatment of pain and modulation of touch perception. Despite any structural differences in the compounds described herein, the compounds of the invention represent unitary subject matter, as they are all defined by the common characteristic of a small-molecule mechanotransduction inhibitor directly effecting STOML3 oligomerization and function. The common structural, mechanistic and/or functional features of the compounds described herein of the Formulae I to IV are novel and entirely unexpected.

In a preferred embodiment the compound described herein for use as a medicament in the treatment of pain, or the method for the treatment of pain, is characterised in that said pain is neuropathic pain.

In a preferred embodiment the compound described herein for use as a medicament in the treatment of pain, or the method for the treatment of pain, is characterised in that said pain is nociceptive pain.

In a preferred embodiment the compound described herein for use as a medicament in the treatment of pain, or the method for the treatment of pain, is characterised in that said pain is induced by and/or associated with tactile stimulation.

In a preferred embodiment the compound described herein for use as a medicament in the treatment of pain, or the method for the treatment of pain, is characterised in that the subject of treatment exhibits painful diabetic neuropathy or any symptom thereof.

In a preferred embodiment of the compound described herein for use as a medicament in the treatment of pain, or the method for the treatment of pain, is characterised in that said treatment comprises the topical administration of a compound as described herein, or a composition comprising said compound, to a subject in need thereof.

In a preferred embodiment of the compound described herein for use as a medicament in the treatment of pain, or the method for the treatment of pain, is characterised in that said treatment comprises the local administration of a compound as described herein, for example locally in the region of pain, or a composition comprising said compound, to a subject in need thereof.

A further aspect of the invention relates to a method for the modulation of touch perception comprising the administration of a compound as described herein, or a composition comprising said compound, to a subject. In a preferred embodiment the administration occurs via topical administration, for example to the skin, or to a mucosal surface. This embodiment relates for example to a non-medical use.

A further aspect of the invention relates to a pharmaceutical composition for use as a medicament in the treatment of pain comprising one or more compounds as described herein, with a pharmaceutically acceptable carrier. Preferably the composition is suitable for topical administration. The invention further relates to the use of the compounds described herein in in vitro methods and/or as research tools, for example as STOML3-inhibitors.

TABLE 1

Preferred compounds of the present invention

| Structure | Name | Molar Mass |
| --- | --- | --- |
| 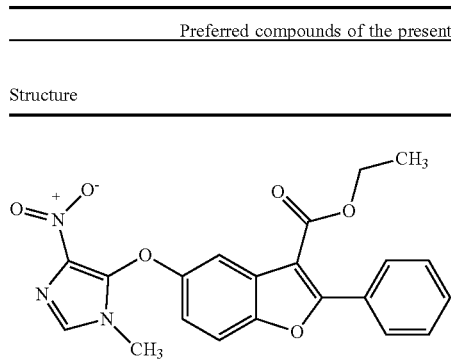 | OB-1 | 407.11 |
| 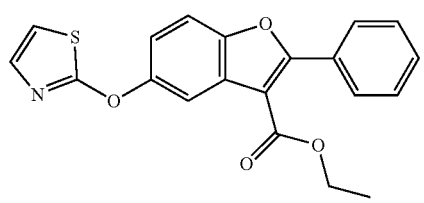 [SMILES: CCOC(=O)c1c(-c2ccccc2)oc2ccc(Oc3nccs3)cc12] | MDC-038 | 366.1 |
| 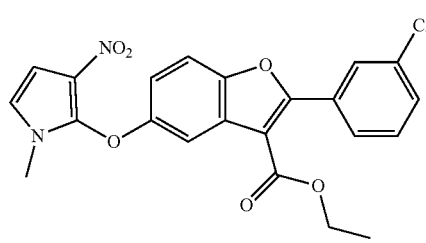 | MDC-D30 | 442.1 |

TABLE 1-continued

Preferred compounds of the present invention

| Structure | Name | Molar Mass |
|---|---|---|
| (structure) | MDC-034 | 442.1 |
| (structure) | OB-2 | 440.14 |

BRIEF DESCRIPTION OF THE DRAWINGS

The invention is further described by the following figures. These are not intended to limit the scope of the invention, but represent preferred embodiments of aspects of the invention provided for greater illustration.

Figure 17:
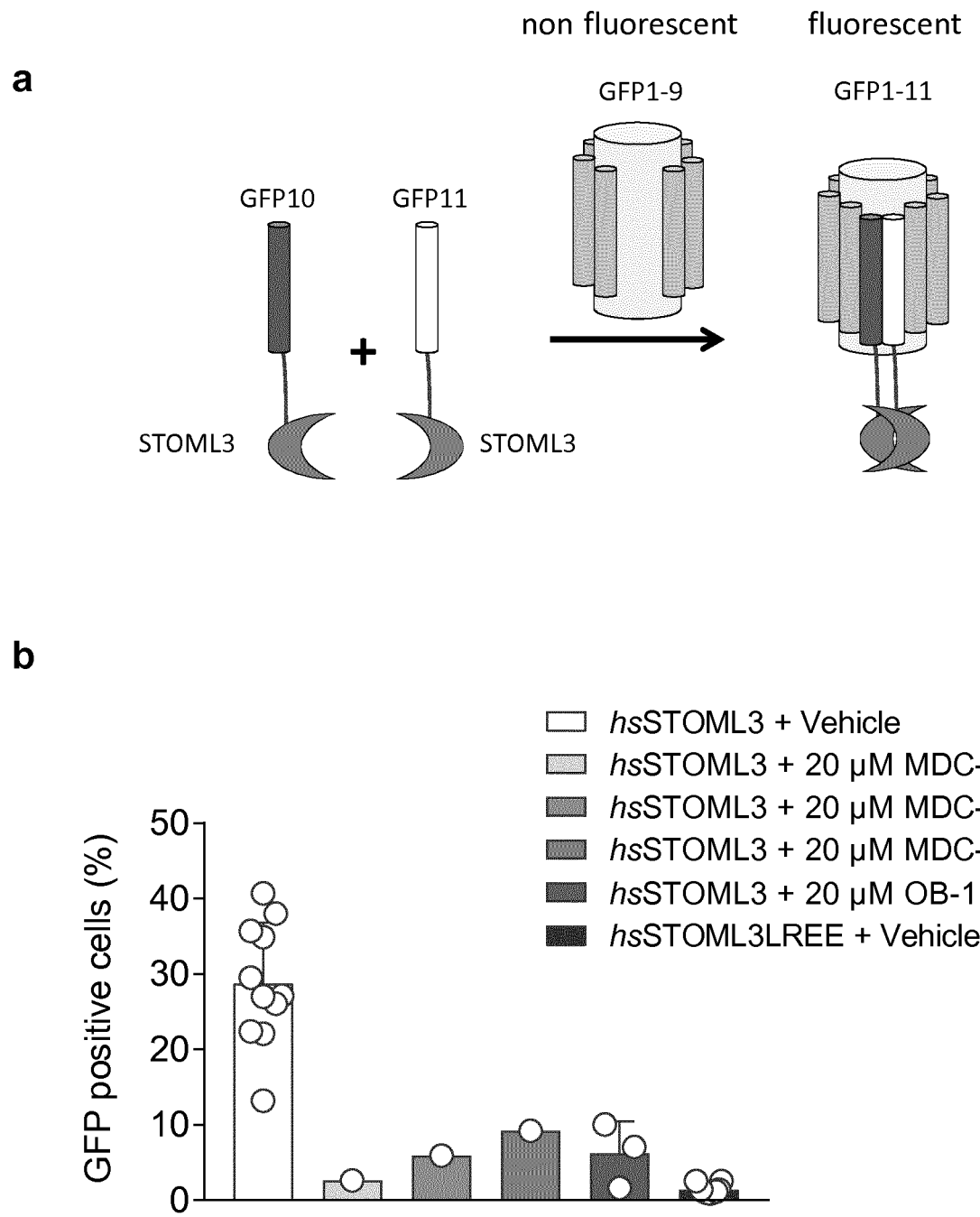

FIG. 17: TriGFP-Assay. (a) The assay is based on the tripartite association between the two twenty amino-acids long GFP tags GFP10 and GFP11, which were fused to hsSTOML3 protein partners, and the complementary GFP1-9 detector (Reference 50). When hsSTOML3 proteins interact, GFP10 and GFP11 self-associate with GFP1-9 and reconstitute functional GFP. GFP signal intensity is measured using flow cytometry technology; quantification of measurements is shown in (b) demonstrating that as a result of hsSTOML3 protein-protein interaction functional GFP is assembled while mutations inserted into hsSTOML3 (hsSTOML3LR93,94EE) as well as the inhibitory compound OB-1 and its derivatives strongly reduce hsSTOML3 self-association resulting in substantially lower GFP signal intensity.

DETAILED DESCRIPTION

The invention relates to chemical compounds that are useful as inhibitors of mechanotransduction in the treatment of pain and modulation of touch perception. A description of the claimed compounds, function and uses of the compounds of the invention is provided in more detail below.

The skin is equipped with specialized mechanoreceptors that allow animals to perceive slight contacts or even a gentle breeze. Indeed some mechanoreceptors are capable of detecting nanometer-scale movements. Movement is transformed into electrical signals via the gating of mechanically-activated ion channels at mechanoreceptor terminals in the skin. The sensitivity of Piezo mechanically-gated ion channels are controlled by stomatin-like protein-3 (STOML3), which is required for normal mechanoreceptor function.

The present invention therefore relates to small molecule inhibitors of STOML3 oligomerization that reversibly reduce the sensitivity of mechanically-gated currents in sensory neurons and silence mechanoreceptors in vivo. STOML3 inhibitors in the skin also reversibly attenuate fine touch perception in normal mice. Under pathophysiological conditions following nerve injury or diabetic neuropathy the slightest touch can evoke intense pain, and under these conditions it is herein demonstrated that STOML3 inhibitors can reverse mechanical hypersensitivity. Thus, the compounds of the present invention may be administered, preferably locally to the skin of a subject, in order to specifically modulate touch. The compounds described herein represent means of treating preferably tactile-driven pain, such as in neuropathic pain.

The present invention is directed to the compounds described herein and their therapeutic and non-therapeutic use in methods comprising administering them to a subject.

Any references herein to murine protein or gene names are intended to refer explicitly also to human homologues or analogues, as may be determined by one skilled in the art based on functional, structural or sequence analysis of the relevant molecule.

The term "subject" includes both human and veterinary subjects. The term "treatment" refers to a therapeutic intervention that ameliorates a sign or symptom of a disease or pathological condition after it has begun to develop. As described herein, the pain experienced by a subject, including those particular embodiments of pain described herein, is considered a disease or pathological condition that may be ameliorated by administration of the compounds described herein. Pain is typically considered an unpleasant sensory experience, for example associated with actual or potential tissue damage. For the purposes of the invention, pain as such is treatable using the compounds described herein, wherein the pain may be the medical condition to be treated or a symptom of a medical condition.

As used herein, the term "ameliorating", with reference to a disease or pathological condition, such as the sensing of pain in a subject, refers to any given beneficial effect of the treatment, such as a reduction in the intensity and/or duration of pain. The beneficial effect can be evidenced, for example, by a delayed onset of clinical symptoms of the disease in a subject, a reduction in severity of some or all clinical symptoms of the disease, a slower progression of the disease, an improvement in the overall health or well-being of the subject, or by other parameters well known in the art that are specific to the particular disease. The present invention therefore relates to an alleviation of pain as a symptom of other disease, or the alleviation of pain as a medical condition itself.

The present invention encompasses both therapeutic treatment and prophylactic treatment of a subject. A "prophylactic" treatment is a treatment administered to a subject, who does not exhibit signs of the medical condition or who preferably exhibits indications of developing or developing further any given medical condition, for the purpose of decreasing the risk of developing pathology or clinical symptoms, such as pain. A prophylactic administration may comprise the administration of the compounds in advance of sensing pain, thereby avoiding or reducing the subsequent occurrence of pain Pain is the most common symptom of disease and the most frequent complaint with which patients present to physicians. Pain is commonly segmented by duration (acute vs. chronic), intensity (mild, moderate, and severe), and type (nociceptive vs. neuropathic). The treatment of pain, in general, and in particular the specific types of pain described herein are the subject matter of the present invention.

Nociceptive pain is caused by noxious stimulation of nociceptors (e.g., a needle stick or skin pinch), which then transmit impulses over intact neural pathways to the spinal nerves and then to the brain. Nociceptive pain is the most well-known type of pain, and is caused by tissue injury detected by nociceptors at the site of injury. After the injury, the site becomes a source of ongoing pain and tenderness. This pain and tenderness are considered "acute" nociceptive pain. This pain and tenderness gradually diminish as healing progresses and disappear when healing is complete. Examples of acute nociceptive pain include surgical procedures (post-op pain) and bone fractures. Even though there may be no permanent nerve damage, "chronic" nociceptive pain results from some conditions when pain extends beyond six months. Examples of chronic nociceptive pain include inflammation, osteoarthritis, rheumatoid arthritis, and musculoskeletal conditions (e.g., back pain), cancer pain, etc.

Neuropathic pain is defined as "pain initiated or caused by a primary lesion or dysfunction in the nervous system" by the International Association for the Study of Pain. Neuropathic pain is not exclusively associated with nociceptive stimulation, although the passage of nerve impulses that is ultimately perceived as pain by the brain is the same in both nociceptive and neuropathic pain. The term neuropathic pain encompasses a wide range of pain syndromes of diverse etiologies. The three most commonly diagnosed pain types of neuropathic nature are diabetic neuropathy, cancer neuropathy, and HIV pain. In addition, neuropathic pain is diagnosed in patients with a wide range of other disorders, including trigeminal neuralgia, post-herpetic neuralgia, traumatic neuralgia, phantom limb, as well as a number of other disorders of ill-defined or, unknown origin.

Neuropathic pain is a form of chronic pain that can persist for weeks, months, years, or decades following an injury or a viral infection such as herpes zoster (shingles) and typically results from damage to peripheral nerves, nerve roots, the spinal cord or certain brain regions. Neuropathic pain is caused by damage to neural structures, such as damage to peripheral nerve endings or nociceptors, which become extremely sensitive to stimulation and can generate impulses in the absence of stimulation (e.g., herpes zoster pain after the rash has healed or phantom limb pain).

Peripheral nerve damage can lead to pathological states where the pain threshold is reduced (i.e., allodynia), an increased response to noxious stimuli (hyperalgesia), or a prolonged response duration (chronic pain). There are two broad types of neuropathic pain: deafferentation pain (caused by partial or complete interruption of central or peripheral neural activity) and sympathetically maintained pain (due to efferent sympathetic activity) (See "Neuropathic Pain," in The Merck Manual, 17th Ed., M. H. Beers and R. Berkow, eds., Merck Research Laboratories, Whitehouse Station, N.J., 1999, pp. 1371-1372). Examples of neuropathic pain include diabetic neuropathy, postherpatic neuralgia and chronic musculoskeletal disorders.

A preferred embodiment of the invention relates to the treatment of tactile allodynia.

A preferred embodiment of the invention relates to the treatment of painful diabetic neuropathy.

A preferred embodiment of the invention relates to the treatment of inflammatory pain.

A preferred embodiment of the invention relates to the treatment of pain induced by or associated with damage to the nervous system, as may arise in viral infections, diabetes, chemotherapy, or multiple sclerosis.

The invention further relates to methods for the modulation, preferably the inhibition of modulation of touch perception.

The term "touch perception" refers to the subject's ability to feel or register physical stimulation via their somatosensory system. The somatosensory system refers to a system of nerve cells that responds to changes to the surface or internal state of the body. Nerve cells called "sensory receptors" (including thermoreceptors, mechanoreceptors, chemoreceptors and nociceptors) send signals along a chain of nerve cells to the spinal cord where they may be processed by other nerve cells and then relayed to the brain for further processing. Sensory receptors are found in many parts of the body including the skin, epithelial tissues, skeletal muscles, bones and joints, internal organs, and the cardiovascular system. In preferred embodiments the invention relates to methods for modulating touch perception, in particular with respect to modulation of mechanoreceptor and/or nociceptor function via administration of the compounds described herein.

The present invention therefore encompasses non-medical treatments, for example comprising the administration of a compound as described herein to modulate touch perception in a subject without a medical disorder, or in cases in cases of prophylactic administration of a compound in situations where pain thresholds are not reached or not to be reached, such that a medical condition does not arise.

With respect to the chemical compounds described herein, the term "alkyl" refers to a branched or unbranched saturated hydrocarbon group of preferably 1 to 7 carbon atoms, such as methyl, ethyl, n-propyl, isopropyl, w-butyl, isobutyl, f-butyl, pentyl, hexyl, heptyl, and the like. Preferred alkyl groups have 1-7 carbon atoms, more preferably 1-6, 1-5, 1-4 or 1-3, 2 or 1 carbon atoms. Any one or more of the alkyl groups described herein may be "substituted alkyls", wherein one or more hydrogen atoms are substituted with a substituent such as halogen, cycloalkyl, alkoxy, hydroxyl, aryl, or carboxyl.

The term "cycloalkyl" refers to a configuration derived from a cycloalkane by removal of an atom of hydrogen, thereby forming preferably cyclopropyl, cyclobutyl, cyclopentyl, cyclohexyl or cycloheptyl, or the like.

The term "alkoxy" refers to a straight, branched or cyclic hydrocarbon configuration and combinations thereof, including preferably 1-7 carbon atoms, more preferably 1-6, 1-5, 1-4 or 1-3 carbon atoms, that include an oxygen atom at the point of attachment (such as O-alkyl). An example of an "alkoxy group" is represented by the formula —OR, or —ROR, where R can be an alkyl group, optionally substituted with halogen, aryl, cycloalkyl, halogenated alkyl. Suitable alkoxy groups include methoxy, ethoxy, n-propoxy, i-propoxy, n-butoxy, i-butoxy, sec-butoxy, cyclohexyloxy, and the like.

The term "aryl" refers to any carbon-based aromatic group including, but not limited to, benzene, naphthalene, and the like. The term "aromatic" also includes "heteroaryl group," which is defined as an aromatic group that has at least one heteroatom incorporated within the ring of the aromatic group. Examples of heteroatoms include, but are not limited to, nitrogen, oxygen, sulfur. The aryl group can be substituted with one or more groups including, but not limited to, alkyl, aryl, halogen, nitro, hydroxy, carboxylic acid, or alkoxy, or the aryl group can be unsubstituted.

Optionally substituted groups, such as "optionally substituted" refers to groups, such as an alkyl group, that when substituted, have from 1-5 substituents, typically 1, 2 or 3 substituents.

The term "5-membered aromatic heterocycle, comprising one or more of N, O and/or S" refers to a configuration comprising a 5-membered ring structure comprising C and one or more of N, O and/or S, preferably selected from a configuration if a hydrogen atom is removed from furan, pyrrole, oxazole, thiophene, thiazole, pyrazole, imidazole, and the like.

In some embodiments, the 5-membered aromatic heterocycle, comprising one or more of N, O and/or S, according preferably to the formulae I, II and/or V, is selected from the list, or a sub-group of the list, from the table below:

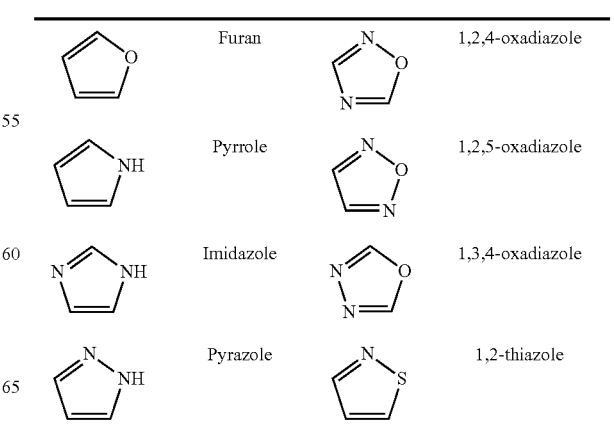

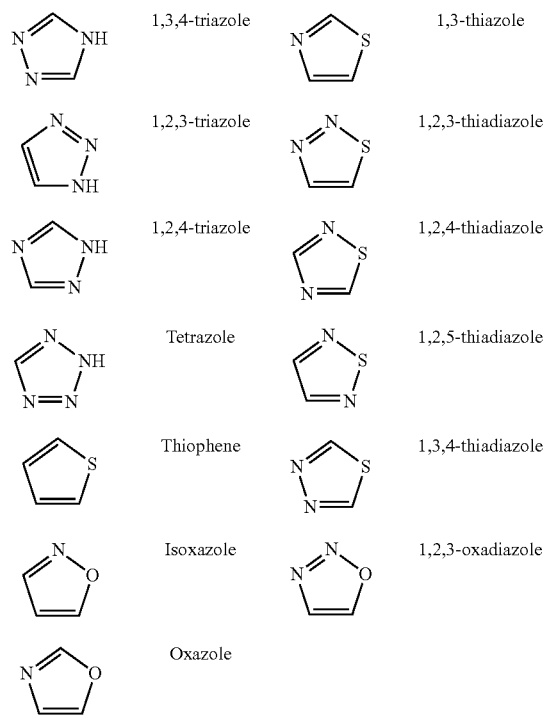

The preferred 5-membered aromatic heterocycles above may, preferably in the context of the embodiments of formulae I, II and/or V, be optionally substituted with Yx, wherein x=0, 1, 2, 3, wherein Y can be the same or different, and wherein Y is nitro, halogen (preferably Br, Cl or F), C1-C7 (preferably C1-C5 or C1-C3) alkyl, alkoxy, optionally substituted with halogen (preferably Br, Cl or F). The preferred 5-membered aromatic heterocycles above may, preferably in the context of the embodiments of formulae I, II and/or V, be covalently bound (as R1) to the O adjacent to R1 via any C atom of the 5-membered aromatic heterocycle. Corresponding changes in the presence and/or position of C=C double bonds or other heteroaromatic binding in the 5-membered aromatic heterocycles may be adjusted appropriately and are within the knowledge of a skilled person.

The "5- or 6-membered carbon ring structure, optionally aromatic" as described herein relates preferably to a cycloalkyl, cycloalkane non-aromatic cyclic structures, such as cyclopentyl or cyclohexyl, and optionally to aromatic cyclic structures, such as phenyl, and the like.

The "6-membered carbon ring structure, optionally aromatic" as described herein relates preferably to a cycloalkyl, cycloalkane non-aromatic cyclic structures, such as cyclohexyl, or to aromatic cyclic structures, such as phenyl, and the like.

The "6-membered aromatic heterocycle, comprising one or more of N, O and/or S" as described herein refers to a configuration comprising a 6-membered ring structure comprising C and one or more of N, O and/or S, preferably selected from a configuration if a hydrogen atom is removed from pyridine, pyridazine, pyrimidine, pyrazine, pyran, triazine, thiazine, thiopyran, oxazine, and the like.

The "6-membered aromatic heterocycle, comprising 1 or 2 N atoms" as described herein refers to a configuration comprising a 6-membered ring structure comprising C and 1 or 2 N atoms, preferably selected from pyridine, pyridazine, pyrimidine, pyrazine, triazine, thiazine, oxazine, and the like. Preferred heterocycles comprise only 1 or 2 N atoms.

Where reference is made to "C1-C7 (preferably C1-C5 or C1-C3) alkyl, cycloalkyl, alkoxy, aryl," or the like, the number of carbon atoms C1-C7 preferably refers to each of the substituents mentioned, although in some embodiments the shorter substituents of C1-C5 or C1-C3 apply to the alkyl, cycloalkyl and/or alkoxy groups, whereby aryl may remain preferably C1-C7, such as C6 phenyl.

The term "nitro" refers to an $NO_2$ group, represented either as $NO_2$ or as

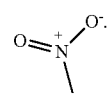

Protected derivatives of the disclosed compound also are contemplated, for example for use in the synthesis of the disclosed compounds. A variety of suitable protecting groups for use with the disclosed compounds are disclosed in Greene and Wuts Protective Groups in Organic Synthesis; 3rd Ed.; John Wiley & Sons, New York, 1999. In general, protecting groups are removed under conditions which will not affect the remaining portion of the molecule. These methods are well known in the art and include acid hydrolysis, hydrogenolysis and the like.

Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures.

The compounds of the invention may also exist in various polymorphous forms, for example as amorphous and crystalline polymorphous forms. All polymorphous forms of the compounds of the invention belong within the framework of the invention and are a further aspect of the invention.

The compound of the invention may also comprise deuterium replacing hydrogen. This replacement may in some circumstances lead to improved metabolic stability (Nature Reviews Drug Discovery 15, 219-221 (2016)).

It is understood that substituents and substitution patterns of the compounds described herein can be selected by one of ordinary skill in the art to provide compounds that are chemically stable and that can be readily synthesized by techniques known in the art and further by the methods set forth in this disclosure.

The present invention relates further to pharmaceutically acceptable salts of the compounds described herein. The term "pharmaceutically acceptable salt" refers to salts or esters of the compounds described herein prepared by conventional means that include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. Any chemical compound recited in this specification may alternatively be administered as a pharmaceutically acceptable salt thereof. Also included are acidic salts of inorganic and organic bases, including but not limited to sodium, potassium, ammonium, triethylamine and the like.

"Pharmaceutically acceptable salts" are also inclusive of the free acid, base, and zwitterionic forms. Descriptions of suitable pharmaceutically acceptable salts can be found in Handbook of Pharmaceutical Salts, Properties, Selection and Use, Wiley VCH (2002). For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

Another aspect of the disclosure includes pharmaceutical compositions prepared for administration to a subject and which include a therapeutically effective amount of one or more of the compounds disclosed herein. In certain embodiments, the pharmaceutical compositions are useful for treating pain. The therapeutically effective amount of a disclosed compound will depend on the route of administration, the species of subject and the physical characteristics of the subject being treated. Specific factors that can be taken into account include disease severity and stage, weight, diet and concurrent medications. The relationship of these factors to determining a therapeutically effective amount of the disclosed compounds is understood by those of skill in the art.

Pharmaceutical compositions for administration to a subject can include at least one further pharmaceutically acceptable additive such as carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. Remington's Pharmaceutical Sciences, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The pharmaceutical compositions can be administered to subjects by a variety of mucosal administration modes, including by oral, rectal, intraocular, intranasal, intrapulmonary, or transdermal delivery, or by topical delivery to other surfaces. Optionally, the compositions can be administered by non-mucosal routes, including by intramuscular, intraocular, subcutaneous, intravenous, intra-arterial, intra-articular, intraperitoneal, intrathecal, intracerebroventricular, or parenteral routes.

The compositions of the disclosure can alternatively contain as pharmaceutically acceptable carrier substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

In a preferred embodiment the invention comprise the topical and/or local administration of a compound as described herein and/or a composition comprising a compound as described herein to a subject. The term "topical administration" refers to the delivery of a pharmacologically active agent to the skin or mucosa of a patient. Topical administration can provide a local rather than a systemic effect. The terms "topical administration" and "transdermal administration" are used interchangeably to mean administration of a pharmacologically active agent to the skin or mucosa of a patient to achieve a therapeutic effect in treating or preventing pain or discomfort at the site of topical or transdermal administration. Preferred administration modes relate to a topical solution, lotion, shake lotion, cream, ointment, gel, foam, transdermal patch, powder, solid form, sponge, tape, paste or tincture. Preferred embodiments relate to creams, foams, gels, lotions, and ointments.

Various additives, known to those skilled in the art, may be included in topical compositions of the present disclosure. For example, solvents, including relatively small amounts of alcohol, may be used to solubilize a compound of the invention. Other optional additives include antioxidants, fragrances, colorant, gelling agents, emulsifiers, thickening agents, stabilizers, surfactants, buffers, cooling agents (e.g., menthol) and the like. Other agents may also be added, such as antimicrobial agents, to prevent spoilage upon storage, i.e., to inhibit growth of microbes such as yeasts and molds. Examples of suitable antimicrobial agents include methyl and propyl esters of p-hydroxybenzoic acid (i.e., methyl and propyl paraben), sodium benzoate, sorbic acid, imidurea, and the like. When applied to skin, a topical composition of the present disclosure can be covered with an occlusive or non-occlusive dressing, which may be porous or non-porous, so as to protect the composition from mechanical removal during the period of treatment, e.g. a plastic film food wrap or other non-absorbent film. Various inert coverings may be employed. Non-woven or woven coverings may be employed, particularly elastomeric coverings, which allow for heat and vapor transport. These coverings can allow for cooling of the pain site, which can provide for greater comfort, while protecting the composition from mechanical removal.

Compositions of the present disclosure can be included in a skin-contacting plaster or patch, i.e., a transdermal system, wherein the composition is contained within a material, e.g., a drug reservoir layer, that can be affixed to the skin. In certain embodiments, the active agent or agents can be contained in a drug reservoir layer underlying an upper backing layer. The system may contain a single reservoir, or it may contain multiple reservoirs. In these systems the active agent(s) may be formulated with the adhesive used to adhere the system to the skin. The system can include a backing layer which functions as the primary structural element of the transdermal system and can provide the system with flexibility and, preferably, occlusivity. The material used for the backing layer can be inert and incapable of absorbing the components of the composition contained within the system.

Further methods of administration relate to those employed for anesthetics. Considering the action of the compounds described herein, namely the inhibition of STOML3 oligomerization and reversible reduction in sensitivity of mechanically-gated currents in sensory neurons, the compounds as described herein may, in some embodiments, be considered or used as anesthetics. An anesthetic (or anaesthetic) is a drug that causes a (preferably reversible) loss of sensation. For example the compounds of the invention may be considered or used as local anesthetics, which cause a reversible loss of sensation in a limited region of the body, in other words, as agents that prevent transmission of nerve impulses without causing unconsciousness.

As such, methods of administration encompassed by the present invention include, but are not limited to, local anesthesia, directed towards treatments to temporarily stop the sense of pain in a particular area of the body, e. g. for minor surgery, the compound can be administered via injection to the site in need, regional anesthesia, intended effectively numb only the portion of the body that undergoes pain or will receive e. g. surgical procedure, whereby an injection of compound is given in the area of nerves that provide feeling to that part of the body. Further means of administration relate to a spinal anesthetic, for example as used for lower abdominal, pelvic, rectal, or lower extremity surgery. Epidural administration may also be envisaged, whereby epidural is similar to a spinal administration and is commonly used for surgery of the lower limbs and during labor and childbirth. Epidural may also be used for chest or abdominal surgical procedures.

In accordance with the various treatment methods of the disclosure, the compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

"Administration of" and "administering a" compound should be understood to mean providing a compound, a prodrug of a compound, or a pharmaceutical composition as described herein. The compound or composition can be administered by another person to the subject (e.g., intravenously, gel, cream, spray) or it can be self-administered by the subject (e.g., tablets, gel, cream, spray).

Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth.

The present invention also relates to a method of treatment of subjects suffering from the various medical conditions disclosed herein. The method of treatment comprises preferably the administration of a therapeutically effective amount of a compound disclosed herein to a subject in need thereof.

A "therapeutically effective amount" refers to a quantity of a specified agent sufficient to achieve a desired effect in a subject being treated with that agent. For example, this may be the amount of a compound disclosed herein useful in alleviating pain in a subject. The therapeutically effective amount or diagnostically effective amount of an agent will be dependent on the subject being treated, the severity of pain, and the manner of administration of the therapeutic composition. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a compound and/or other biologically active agent within the methods and formulations of the disclosure is about 0.001 mg/kg body weight to 50 mg/kg body weight, 0.01 mg/kg body weight to about 20 mg/kg body weight, such as about 0.05 mg kg to about 5 mg/kg body weight, or about 0.2 mg/kg to about 2 mg/kg body weight.

The instant disclosure also includes kits, packages and multi-container units containing the herein described pharmaceutical compositions, active ingredients, and/or means for administering the same for use in the prevention and treatment of diseases and other conditions in mammalian subjects.

EXAMPLES

The invention is further described by the following examples. These are not intended to limit the scope of the invention, but represent preferred embodiments of aspects of the invention provided for greater illustration.

Methods Employed in the Examples

Behavioral Assessment:

The experiments in this study were carried out on adult inbred male mice (adult C57Bl6/6 obtained from Charles River, Sulzfeld, Germany) or adult mice generated and breed in the laboratory (Stoml3$^{-/-}$ or Stoml3$^{lacz}$). Animal housing and care, as well as protocols for humane euthanasia, are registered and approved by the appropriate German federal authorities (State of Berlin). All experiments were performed in compliance with the German laws and the guidelines of the European Community for the use of animals in research and were approved by the local ethical committee by the appropriate German federal authorities (State of Berlin). Animals were kept under controlled temperature and a 12-h light, 12-h dark cycle with lights on at 06:00 A.M., all behavioral tests were conducted during the light phase.

Statistical Analysis:

All data were tested for normal distribution. Appropriate statistical tests applied for data analysis are referred to in the figure legend. Multiple comparisons were performed by repeated measures two-way ANOVA followed by Bonferroni post hoc test. Significance levels of $p<0.05$ (*), $p<0.01$ (), and $p<0.001$ (*) were used. Statistical analyses and exponential fits were made using the GraphPad Prism or Igor Pro 6.11. software.

Expression Constructs:

Constructs for BiFC analysis were created by inserting the gene of interest, in frame, into the multiple cloning site of pBiFC-VC155 or pBiFC-VN173. Point mutations were introduced using PCR-based site-directed mutagenesis. FLAG-tagged variants were generated using standard cloning techniques.

Rt-PCR Analysis:

Lumbar L3-L6 dorsal root ganglia (DRG) and olfactory bulb were dissected from CCI and control mice, pooled and total RNA was extracted by TRIzol method (Invitrogen) as per manufacturer recommendations and treated with the TURBO DNA-Free™ Kit to avoid DNA contamination. RNA was quantified using NanoDrop 2000 UV-Vis spectrophotometer (Thermo Scientific) and reverse-transcribed using SuperScript® III Reverse Transcriptase (Invitrogen). TaqMan Quantitative RT-PCR was used to detect the expression of STOML3 mRNA with appropriate primers in combination with the TaqMan probe #53 from Roche Universal Probe Library. Each sample was performed in triplicate in an ABI Prism 7700 Sequence Detection System (Thermo Scientific).

HEK-293 cells (passage numbers 4-20) were cultured in DMEM plus 10% fetal calf serum (FCS). Neuro2A (N2A) cells were cultured in DMEM/Opti-MEM media plus 10% FCS.—Sensory DRG neurons were isolated from 4 week old *Mus musculus* (C57Bl/6). Approximately 20 ganglia were collected from each mouse and individual cells were isolated by treating ganglia with 1 µg/ml collagenase IV for 30 min, followed by 1 ml of 0.05% trypsin, in PBS, for 5-20 min at 37° C. Enzyme-treated ganglia, in DMEM/F-12 media containing 10% Horse Serum (HS), were disrupted by gently passaging through a 20 G needle; cells were then collected by centrifugation (1000 rpm, 3 min), washed and finally re-suspended in DMEM/F-12, 10% HS media (at no point were neurotrophins added to the culture). Sensory neurons were then seeded on EHS-laminin coated substrate and cultured overnight. Experiments involving isolated sensory neurons were conducted within 24-36 hours of isolation of the cells.

High Through-Put Screen:

HEK-293 cells were cultured in T-150 flasks to approximately 70% confluence; cells were co-transfected with plasmids encoding STOML3-VC and STOML3-VN using Fugene-HD, as per manufacturer's instructions. The transfection reaction was allowed to proceed for 8 h before cells were recovered from the dishes, resuspended in DMEM media containing 25 mM HEPES and lacking phenol red. Cells were plated in PLL-coated 384 well plates using an automated dispenser (EL406 Microplate Washer Dispenser). Plates already contained compound from the ChemBioNet compound library1. The final assay volume was 40 µl cells with 10 µM of compound. Two positive control columns on each individual plate did not contain compound and the according amount of DMSO was added instead. Development of the YFP fluorescence signal was monitored overnight (15 h), with readings taken every 3 h (ex: 515±8 nm, em: 535±8 nm). In between readings cells were maintained at 37° C., 5% CO2, and 95% humidity. The overnight monitoring of signal development was performed on a Freedom Evo workstation equipped with a robotic arm for plate transport and a Safirell plate reader for fluorescence measurement (Tecan Group Ltd, Männedorf, Switzerland), and an integrated STX44-ICSA automated plate incubator (Liconic AG, Mauren, Liechtenstein) for plate storage in between measurements. Experiments were repeated with 20 plates each day until the entire compound library had been screened and data was normalized to in-plate controls.

Compounds of interest were selected from the slope of YFP-signal vs time. Each well was compared to the average slope of in-plate positive controls (normalized percent activity), and compared to the mean and standard deviation of all samples on a plate (without the controls), giving a Z score as a measure of statistical significance. Initially, compounds were re-screened in triplicate to confirm whether or not the noted differences were repeatable; compounds with confirmed activity were selected for further analysis.

TriGFP Assay

N2a cells were cultured in 6-well plates to approximately 70% confluence; cells were co-transfected with plasmids encoding GFP1-9, STOML3-GFP10 and STOML3-GFP11 using PEI, as per manufacturer's instructions. The transfection reaction was allowed to proceed for 8 h before compound incubation at 20 µM final concentration. Twenty-four hours after transfection cells were collected, fixed with 4% PFA for 10 minutes and resuspended in PBS. Cell suspensions were used for flow cytometry analysis.

dSTORM Imaging:

N2A cells were cultured on EHS-Laminin coated precision coverglass, thickness 0.17, then transfected with a plasmid encoding STOML3-FLAG. After overnight incubation, cells were treated for 3 hours with 20 µM compound, or DMSO as a control. Cells were then fixed (15 min, 4% PFA), permeabilized (0.05% TritonX 100, 5 min) and blocked (phosphate buffered saline (PBS) containing 10% fetal goat serum (FGS), 37° C., 1 hr). Cell were labeled with mouse anti-FLAG antibody (M2 clone, 1:100 in PBS containing 10% FGS). The secondary antibody was an Alexa647-conjugated, goat anti-mouse antibody (1:100 in PBS plus 10% FGS, 1 h, 37° C.). After staining, the samples were fixed again. Prior to dSTORM imaging, coverslips were mounted in dSTORM buffer PBS, pH 7.4, containing an oxygen scavenger (0.5 mg/ml glucose oxidase), 40 mg/ml catalase, 10% (w/v) glucose and 100 mM MEA$^2$.

The custom-built dSTORM system was based on a Nikon Ti microscope. Before acquisition, we illuminated the Alexa647-labeled sample with 643 nm to switch fluorophores into the OFF state. After the molecules started blinking, we acquired a sequence of frames (typically 10,000-20,000) using a 100×1.49 NA objective, a 1.5 magnification lens and non-binned EMCCD array. An exposure time of 30 ms was used to have good signal-to-noise and a high number of blinking single molecules/frame.

dSTORM Localization, Drift Correction and Reconstruction

In order to aid drift correction PLL-coated Tetra-speck fluorescent beads were allowed to adhere to the sample overnight. Localization: Single molecules were localized using open source software rapidSTORM 3.2. In short, the source images are first smoothed via median operator followed by a fill-hole operation to reduce noise. In these 'de-noised' images, rapidSTORM performs a Gaussian fit (Levenberg-Marquardt parameter estimation) to each intensity spot, whereas the fit quality and peak maxima were used as a quality measure for the localization. This fit yields the precise position of the single molecule with sub-pixel accuracy, the total intensity of the single molecule event and the frame number of the event within the image sequence. Sample drift was corrected by using fiduciary beads in the sample as reference points (custom written algorithm, GREGOR).

For analysis of STOML3 domain size, all reconstructed images were blinded and then from each imaged cell 100 individual dots were cropped (size: 20×20 pixels). A 2D-Gaussian fit was calculated using the Igor software (WaveMetrics, USA). The x-width and y-width for each dot were included in the data set as domains were not necessarily circular. After domain sizes had been determined for each cell, images were unblinded and then normalized against the average domain size for control cells prepared and imaged on the same day.

Chemical Synthesis OB-1:

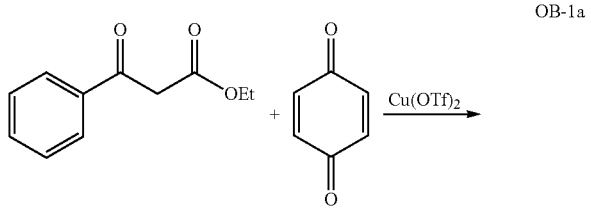

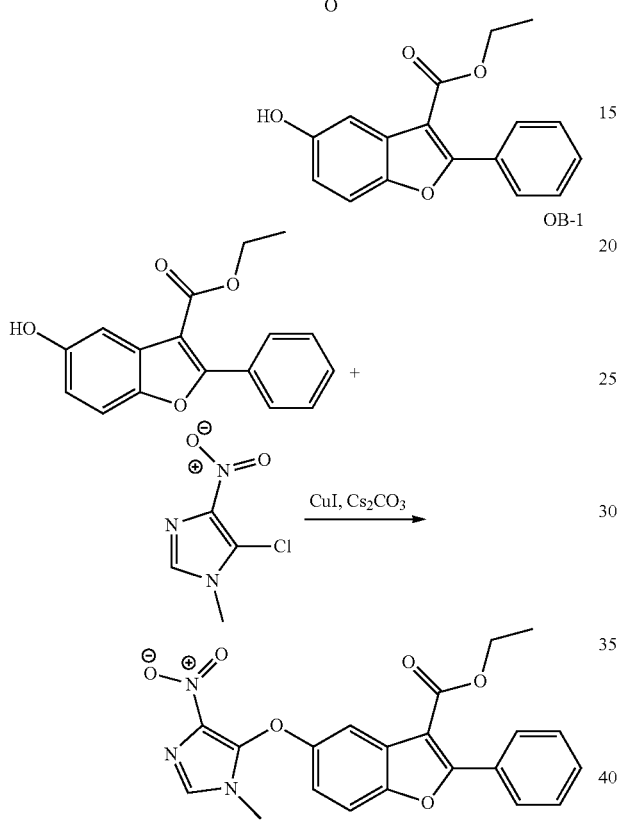

Ethyl 5-hydroxy-2-phenylbenzofuran-3-carboxylate 5.6 g (29.06 mmol) of ethyl-3-oxo-3-phenylpropanoate was solubilized in 50 ml toluene and 525 mg (1.45 mmol) of Cu(OTf)$_2$ was added. Next, 1.57 g (14.5 mmol) of benzoquinone was solubilized in 20 ml of toluene and added dropwise to the reaction mixture followed by reflux for 3 h. The mixture was quenched with NH$_4$Cl and extracted three times with ethyl acetate. The combined organic layers were washed with brine and dried with Na$_2$SO$_4$. The crude product was purified by chromatography on silica gel eluting with a gradient of Hex/EE (10:1) to give 2.24 g of ethyl-5-hydroxy-2-phenylbenzofuran-3-carboxylate (Yield: 27%).

$^1$H NMR (300 MHz, DMSO-d$_6$) δ 9.48 (s, 1H), 7.93 (dd, J=6.6, 2.9 Hz, 2H), 7.56-7.46 (m, 4H), 7.37 (d, J=2.4 Hz, 1H), 6.85 (dd, J=8.8, 2.5 Hz, 1H), 4.31 (q, J=7.1 Hz, 2H), 1.31 (t, J=7.1 Hz, 3H). LCMS: Rt=3.66 min; MS (ESIpos) m/z=283.1 [M+H]$^+$.

Ethyl 5-((1-methyl-4-nitro-1H-imidazol-5-yl)oxy)-2-phenylbenzofuran-3-carboxylate (OB-1)

0.5 g (1.77 mmol) of ethyl-5-hydroxy-2-phenylbenzofuran-3-carboxylate was solubilized in 20 ml DMF and 1.2 eq Cs$_2$CO$_3$ (0.7 g, 2.1 mmol), 0.1 eq CuI (33 mg, 0.17 mmol) and 285 mg (1.77 mol) 5-chloro-1-methyl-4-nitro-1H-imidazole were added. The mixture was stirred for 3 h at RT. The organic solvent was removed under reduced pressure. The crude product was purified by chromatography on silica gel eluting with a gradient of Hex/EE (3:2) to give 644 mg of ethyl-5-(1-methyl-4-nitro-1H-imidazol-5-yloxy)-2-phenylbenzofuran-3-carboxylate (Yield: 89%).

$^1$H NMR (300 MHz, DMSO-d$_6$) δ 8.01-7.95 (m, 2H), 7.85 (s, 1H), 7.77 (d, J=9.0 Hz, 1H), 7.59-7.52 (m, 3H), 7.47 (d, J=2.7 Hz, 1H), 7.25 (dd, J=9.0, 2.8 Hz, 1H), 4.26 (q, J=7.1 Hz, 2H), 3.61 (s, 3H), 1.21 (t, J=7.1 Hz, 3H). LCMS: Rt=3.73 min; MS (ESIpos) m/z=408.1 [M+H]$^+$.

Additional Preparative Examples

The following examples were synthesized similar to the synthesis of OB-1.

Example: Ethyl 2-phenyl-5-(thiazol-2-yloxy)benzofuran-3-carboxylate (A1) (MDC-D38)

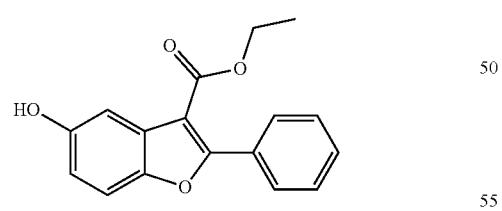

Ethyl-5-hydroxy-2-phenylbenzofuran-3-carboxylate (50 mg, 0.177 mmol) was dissolved in DMF (2 ml). Cs$_2$CO$_3$ (70 mg, 0.21 mmol, 1.18 eq), CuI (3.3 mg, 0.0177 mmol, 0.1 eq) and 2-chlorothiazole (15.19 μl, 0.177 mmol, 1 eq) were added. The mixture was shaken at room temperature for 15 h. After HPLC showed only minor product formation, the mixture was stirred at 80° C. for 1 hour. The mixture was stirred additionally at 120° C. overnight. The mixture was cooled to room temperature, diluted, filtered and purified by preparative HPLC (eluents: water and acetonitrile). The desired fractions were lyophilized to yield the title compound A1 (16 mg, 0.04 mmol, 25%) as a white powder. $C_{20}H_{15}NO_4S$. LCMS: Rt=1.72 min; MS (ESIpos) m/z=366.1 [M+H]⁺.

Example: Ethyl 2-(3-chlorophenyl)-5-((1-methyl-4-nitro-1H-imidazol-5-yl)oxy)benzofuran-3-carboxylate (B2) (MDC-D30)

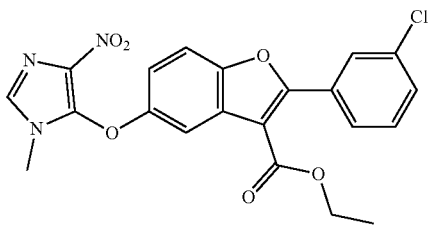 [SMILES: CCOC(=O)c1c(-c2cccc(Cl)c2)oc2ccc(Oc3c([N+](=O)[O-])ncn3C)cc12]

Step 1: Ethyl 2-(3-chlorophenyl)-5-hydroxybenzofuran-3-carboxylate (B1)

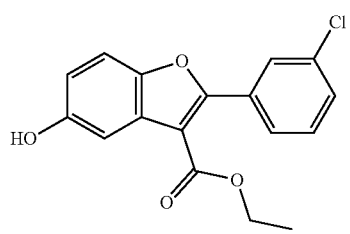 [SMILES: CCOC(=O)c1c(-c2cccc(Cl)c2)oc2ccc(O)cc12]

Ethyl-(3-chlorobenzoyl)acetate (300 mg, 1.32 mmol) was dissolved in toluene (10 ml). Cu(OTf)₂ (48 mg, 0.132 mmol, 0.1 eq) was added. Then benzoquinone (152 mg, 1.39 mmol, 1.05 eq) dissolved in toluene (10 ml) was added dropwise to the solution. The mixture was stirred at reflux for 2 hours. The mixture was cooled to room temperature. Saturated aq. NH₄Cl solution (10 ml) and EtOAc (30 ml) were added. The layers were separated and the aqueous phase was extracted with EtOAc (2×20 ml). The combined organic layers were washed with brine (20 ml), dried with Na₂SO₄ and concentrated in vacuo. The mixture was purified by flash column chromatography yielding the compound B1 as a light brown solid (80 mg, 0.25 mmol, 19%). $C_{17}H_{13}ClO_4$. LCMS: Rt=1.55 min; MS (ESIpos) m/z=317.1 [M+H]+; MS (ESIneg) m/z=315.1 [M−H]⁻.

Step 2: Ethyl 2-(3-chlorophenyl)-5-((1-methyl-4-nitro-1H-imidazol-5-yl)oxy)benzofuran-3-carboxylate (B2)

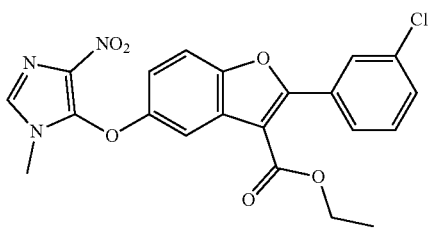 [SMILES: CCOC(=O)c1c(-c2cccc(Cl)c2)oc2ccc(Oc3c([N+](=O)[O-])ncn3C)cc12]

Ethyl 2-(3-chlorophenyl)-5-hydroxybenzofuran-3-carboxylate (B1) (70 mg, 0.22 mmol) was dissolved in DMF (2 ml). Cs₂CO₃ (85 mg, 0.261 mmol, 1.18 eq) was added, followed by CuI (4 mg, 0.022 mmol, 0.1 eq) and 5-chloro-1-methyl-4-nitroimidazole (36 mg, 0.22 mmol, 1 eq). The mixture was stirred overnight at 120° C. The mixture was cooled to room temperature, diluted with acetonitrile, filtered and purified by preparative HPLC (eluents: water and acetonitrile). The desired fractions were lyophilized to yield the title compound B2 (5 mg, 0.01 mmol, 5%) as a white powder. $C_{21}H_{16}ClN_3O_6$. LCMS: Rt=1.59 min; MS (ESIpos) m/z=442.1 [M+H]⁺.

Example: Ethyl 2-(4-chlorophenyl)-5-((1-methyl-4-nitro-1H-imidazol-5-yl)oxy)benzofuran-3-carboxylate (C2) (MDC-D34)

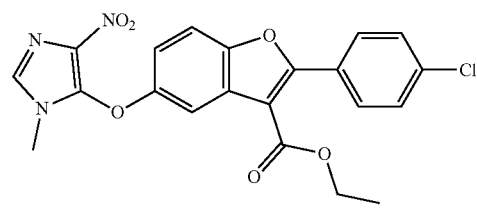 [SMILES: CCOC(=O)c1c(-c2ccc(Cl)cc2)oc2ccc(Oc3c([N+](=O)[O-])ncn3C)cc12]

Step 1: Ethyl 2-(4-chlorophenyl)-5-hydroxybenzofuran-3-carboxylate (C1)

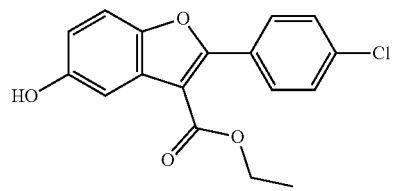 [SMILES: CCOC(=O)c1c(-c2ccc(Cl)cc2)oc2ccc(O)cc12]

3-(4-Chlorophenyl)-3-oxo-propionic acid ethyl ester (200 mg, 0.88 mmol) was dissolved in toluene (10 ml). Cu(OTf)₂ (33.45 mg, 0.0925 mmol, 0.1 eq) was added. Then benzoquinone (100 mg, 0.925 mmol, 1.05 eq) dissolved in toluene (10 ml) was added dropwise to the solution. The mixture was stirred at reflux for 2 hours. The mixture was cooled to room temperature. Saturated aq. NH₄Cl solution (10 ml) and EtOAc (30 ml) were added. The layers were separated and the aqueous phase was extracted with EtOAc (2×20 ml). The combined organic layers were washed with brine (20 ml), dried over Na₂SO₄ and concentrated in vacuo. The mixture was purified by flash column chromatography yielding the compound C1 as a light brown solid (117 mg, 0.37 mmol, 21%). $C_{17}H_{13}ClO_4$. LCMS: Rt=1.56 min; MS (ESIpos) m/z=317.1 [M+H]+; MS (ESIneg) m/z=315.1 [M−H]⁻.

Step 2: Ethyl 2-(4-chlorophenyl)-5-((1-methyl-4-nitro-1H-imidazol-5-yl)oxy)benzofuran-3-carboxylate (C2)

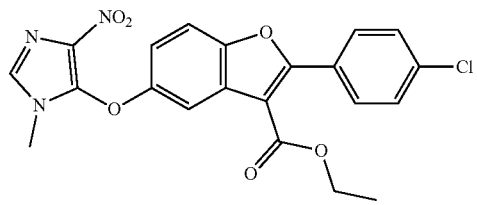 [SMILES: CCOC(=O)c1c(-c2ccc(Cl)cc2)oc2ccc(Oc3c([N+](=O)[O-])ncn3C)cc12]

Ethyl 2-(4-chlorophenyl)-5-hydroxybenzofuran-3-carboxylate (C1) (80 mg, 0.25 mmol) was dissolved in DMF (2 ml). $Cs_2CO_3$ (97 mg, 0.298 mmol, 1.18 eq) was added, followed by CuI (5 mg, 0.025 mmol, 0.1 eq) and 5-chloro-1-methyl-4-nitroimidazole (40 mg, 0.25 mmol, 1 eq). The mixture was stirred overnight at 120° C. The mixture was cooled to room temperature, diluted with acetonitrile, filtered and purified by preparative HPLC (eluents: water and acetonitrile). The desired fractions were lyophilized to yield the title compound C2 (11 mg, 0.02 mmol, 10%) as a white powder. $O_{21}H_{16}ClN_3O_6$. LCMS: Rt=1.60 min; MS (ESIpos) m/z=442.1 [M+H]+.

General Synthesis Scheme:

The general method of synthesis may be employed for compounds of Formula I-II. In the synthesis, different aromatic and alkyl $R_1$ groups are used. For most of the compounds $R_2$=ethyl. The other ester derivatives are obtained by transesterification of the ethyl ester. The resulting benzofuran derivatives 3 will be arylated on the phenol position with thiazole and imidazole derivatives 4 to produce the final targets 5.

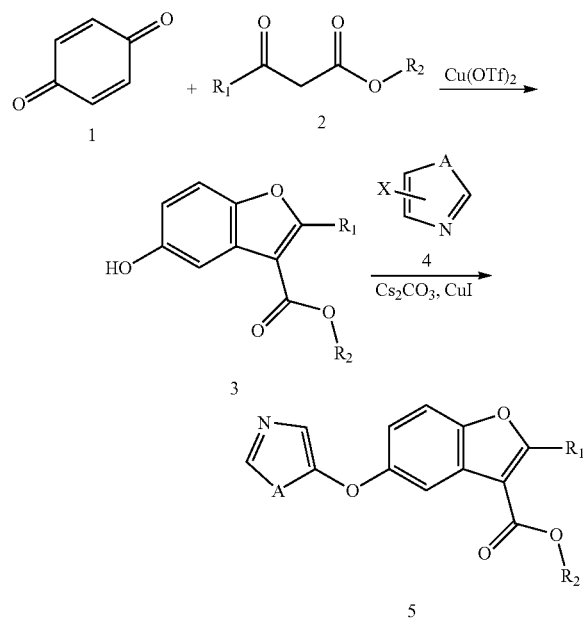

Electrophysiology:

Whole-cell, patch-clamp recordings were conducted as previously described 5-7, using patch pipettes with a tip resistance of 3-6 MΩ, filled with a solution of: 110 mM KCl, 10 mM NaCl, 1 mM MgCl2, 1 mM EGTA and 10 mM HEPES, adjusted to pH 7.3 with KOH. (For experiments on DRG neurons 10 mM QX-314 was added to the pipette to block voltage-gated sodium channels 8 Extracellular solutions contained 140 mM NaCl, 4 mM KCl, 2 mM CaCl2, 1 mM MgCl2, 4 mM glucose, 10 mM HEPES, adjusted to pH 7.4 with NaOH. A Zeiss 200 inverted microscope and an EPC-10 amplifier in combination with Patchmaster software was used, data was analyzed using Fitmaster software (HEKA Electronik GmbH, Germany). Pipette and membrane capacitance were compensated using the auto function of Patchmaster, series resistance was compensated by at least 60% to minimize voltage errors. Mechanical stimuli were applied using a polished glass probe driven by the MM3A micromanipulator (Kleindiek Nanotechnik, Germany). Mechanical stimuli were applied by either; indenting the cell soma or by culturing cells on elastomeric pillar arrays and applying the stimulus to the cell-substrate interface by deflecting an individual pilus.

Briefly, elastomeric pillar arrays of defined dimensions were cast in PDMS with an elasticity of 2 MPa. Cells cultured on these arrays were monitored using whole-cell patch-clamp whilst a glass probe was used to apply repeated deflections (of differing magnitudes) to an individual pilus directly beneath the cell. Images were obtained of the pilus before and after deflection and images were analyzed off-line to determine the exact deflection for each data point. Images were obtained using a 40×LD objective and a CoolSNAP EZ CCD camera. Images were analyzed off-line using Igor software (WaveMetrics, USA). The collection of stimulus-response data using pillar arrays generates data sets with variation in both x and y. In order to effectively compare groups for each cell studied we binned response data by stimulus size in the following bins: 0-10, 10-50, 50-100, 100-250, 250-500, 500-1000. For each cell, current amplitudes within each bin were averaged and then bins averaged between cells—we then tested for significance by testing whether the current amplitude for a given stimulation range (i.e. bin) differed between samples. A power analysis was used to determine that moderate to strong effects between samples could be detected with a sample size >4. Data sets were in excess of this number. To distinguish mechanoreceptors from nociceptors in the mixed population of acutely prepared DRG neurons, the shape of the generated action potential (AP) was used. Cells with APs that exhibited a hump in the falling phase were classified as nociceptors. For quantitative analysis of mechanosensitivity we measured responses in the most sensitive sub-population of mechanoreceptors, previously defined as TypeII mechanoreceptors (Poole et al., 2014). This population was identified as those cells with APs lacking a hump in the falling phase and a full width at half maximum (FWHM) of at least 0.7 ms, (average, ±s.e.m.: 0.9±0.04 ms)

To test the effect of compounds on stomatin modulation of ASIC currents CHO cells were transfected with vectors encoding Stomatin and ASIC3, in a ratio of 4:1 using lipofectamine, as per manufacturer's instructions. Cells were incubated with 20 μM OB-1 for 3 hours in extracellular buffer (see above), and OB-1 was maintained in the media during electrophysiological experiments. ASIC3 channels were gated by applying solutions of pH6 and pH4, and both the transient and sustained peak current density was measured.

Ex Vivo Skin Nerve Preparation:

Mice were killed by CO2 inhalation for 2-4 min followed by cervical dislocation. The saphenous nerve and the shaved skin of the hind limb were dissected free and placed in an organ bath. The chamber was perfused with a synthetic interstitial fluid (SIF buffer) the composition of which was (in mM): NaCl, 123; KCl, 3.5; MgSO4, 0.7; NaH2PO4, 1.7; CaCl2), 2.0; sodium gluconate, 9.5; glucose, 5.5; sucrose, 7.5; and HEPES, 10 at a pH of 7.4. The skin was placed with the corium side up in the organ bath. The nerve was placed in an adjacent chamber on a mirror to aid fiber teasing under a stereomicroscope. Fine filaments were teased from the saphenous nerve and placed on the recording electrode. Electrical isolation was achieved with mineral oil.

For the electrical search protocol a micro electrode (1 MΩ) was gently maneuvered to contact the epineurium of the nerve trunk and an electrical stimulation was delivered at a one second interval with square wave pulses of 50-500 ms duration. In most filaments 3-5 single units were counted. The electrical nerve stimulation was done at 2 distant sites of the saphenous nerve to trace electrically identified units to their receptive fields. Mechanical sensitivity of single units was tested by mechanical stimulation with a glass rod. For the mechanical search protocol, single units were identified by gentle mechanical stimulation of their receptive field with a glass rod. Mechanically-evoked spikes were visualized and the template saved in an oscilloscope. Then, a sharp tungsten metal electrode was placed in the receptive field and an electrically evoked spike was elicited with suprathreshold current pulses and the electrical latency, the time from the stimulation artifact to spike, was recorded. The distance between the stimulating and recording electrode was designated as the conduction distance. For each isolated fiber the conduction velocity was calculated by dividing conduction distance over electrical latency for the spike.

A computer-controlled nanomotor (Kleindiek, Reutlingen, Germany) was used to apply controlled displacement stimuli of known amplitude and velocity. The probe was a stainless steel metal rod and the diameter of the flat circular contact area was 0.8 mm containing a force transducer (Kleindiek, Reutlingen, Germany). The signal driving the movement of the linear motor and raw electrophysiological data were collected with a Powerlab 4.0 system (ADInstruments) and spikes were discriminated off-line with the spike histogram extension of the software.

Tactile Perception Task:

Male C57B16/J mice were anaesthetized and a lightweight metal headholder was implanted to the skull using glue (Loctite 401, Henkel) and dental cement (Paladur®, Heraeus). Mice were habituated to the head-restraint and the behavioral setup over 1-2 days. Mouse licking and forepaw behavior was monitored with three custom-made capacitance sensors: a licking sensor, a rest sensor and a target sensor that provided an online monitor of paw or tongue contact. The rest sensor was a ball (diameter: 6 mm) mounted on a glass rod of 30 mm length, glued to a piezoelectric bender (PICMA® Multilayer Piezo Bender Actuator, Physik Instrumente). The piezo generated a 30 ms cosine tactile pulse via a piezo amplifier system (Sigmann Elektronik). A urethane foam buffer (Poron®, Rogers Cooperation) was placed between the piezo and the supporting platform to reduce ringing oscillations after the stimulus pulse. The stimulus amplitude was calibrated with a highspeed (300 Hz) camera (Dalsa Genie HM640). The target sensor (diameter: 6 mm) had a start position of 10 mm horizontally in front of the rest sensor and was attached to a Fisso 3D articulated arm on a linear translation stage (ST9-100-2 eco-P, ITK Dr. Kassen GmbH, Germany). Mice were water restricted and given approximately 4×0.6 μl water rewards on condition of touching the target sensor within a defined latency from stimulus onset and licking the water dispenser. The target sensor moved to the start position at the start of a new trial and away from the mouse at the end of the trial. Inter-trial interval was randomized between 7 and 13 s. White noise was played throughout the trial. The response window (rewarded stimulus-to-touch latency) was reduced during behavioral training to 500 ms during the testing session. Mice were trained with high amplitude stimuli (620 μm) and then tested in the same session with seven different stimulus amplitudes (in μm: 45, 80, 125, 170, 275, 385, 620) and a no-stimulus trial to calculate the false alarm rate. Stimuli were presented in a randomized order. The setup was controlled with custom written software in LabView 10.0 (National Instruments 2010). Drug injections of OB-1 or DMSO alone were dissolved in Ringer's solution (in mM: 135 NaCl, 5 KCl, 5 HEPES, 1.8 CaCl2, 1 MgCl2) to make the OB-1 and vehicle solution. To test the impact of OB-1 on tactile perception we made subcutaneous injections into the right forepaw of OB-1 or the vehicle solution. Injections were made 3 to 5 hours prior to behavioral testing.

Approximately 5 μl was injected into the digits with a glass micropipette and 10 μl into the palm with a Hamilton syringe, gauge 33. During the injection procedure, the mouse was anaesthetized with isoflurane (1.5 to 2.0% in O2). The injection procedure lasted around 15 minutes after which the mouse was moved to the home cage for recovery before behavioral testing.

To construct the psychometric curves we first averaged the rates of pressing the target sensor within 500 ms from stimulus onset across 5 mice. Next we fitted the data with a sigmoid function in Igor Pro 6.11 (WaveMetrics):

$$f(x) = \text{base} + \frac{\text{max}}{1 + \exp\left(\frac{xY50 - x}{\text{slope}}\right)}$$

Figure 5:
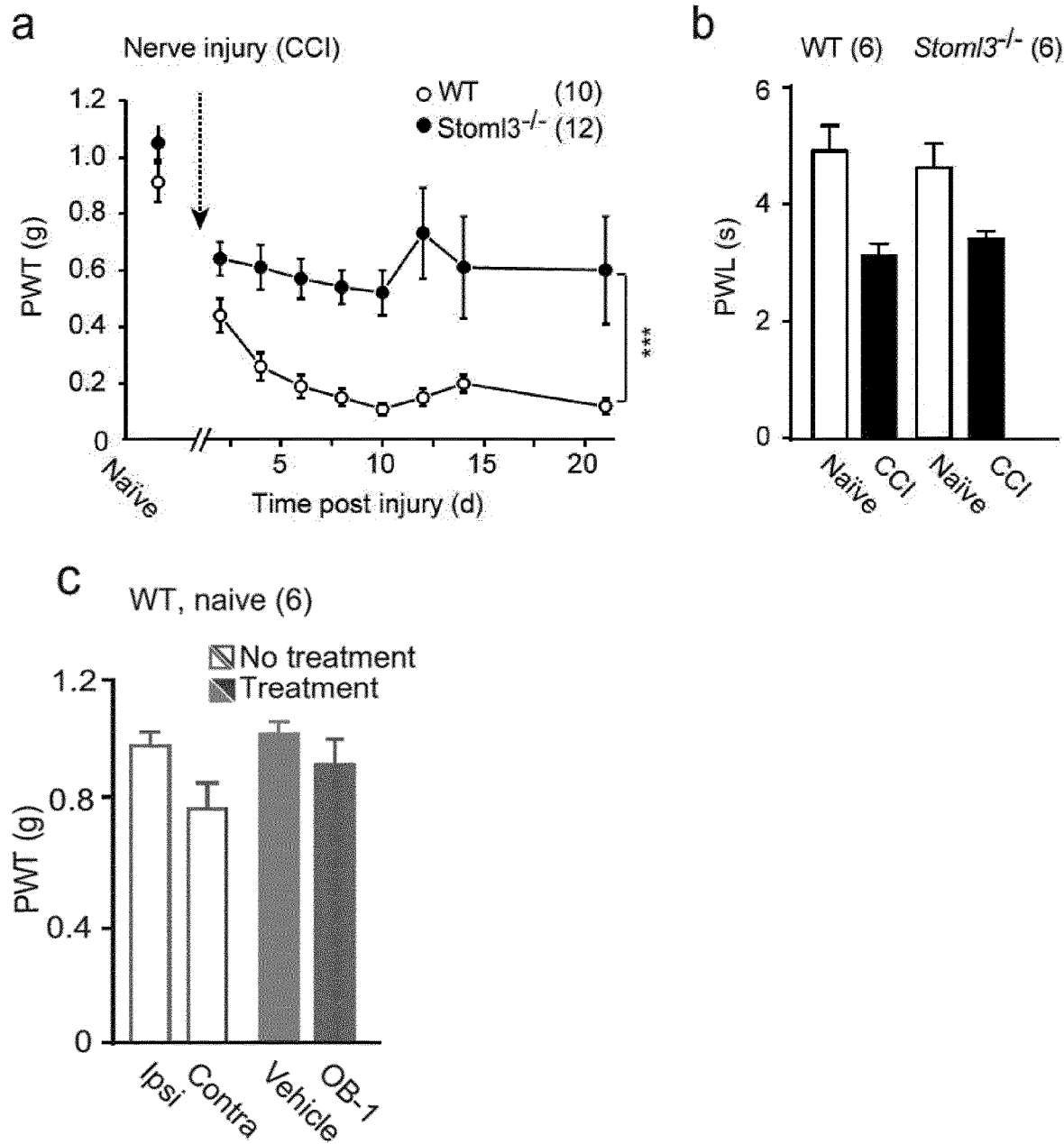
FIG. 5: Tactile-evoked pain can be treated with OB-1. a, Development of tactile-evoked pain after traumatic nerve injury is shown. Paw withdrawal thresholds (PWT) to varying forces of von Frey filaments before and after unilateral CCI were measured. Note that after nerve injury Stoml3−/− mice develop significantly less tactile-evoked pain compared to wild type animals (*$p<0.001$; Two-way ANOVA; numbers indicate numbers of mice examined data are displayed as mean of individual median PWTs; +s.e.m.). b, Paw withdrawal latencies (PWLs) to a standard radiant heat source applied to the ipsilateral hind paw of wild type and Stoml3−/− mice before and after CCI were not different between the genotypes; numbers indicate mice treated; data are displayed as mean PWL±s.e.m.). c, Treatment of naive mice with OB-1 does not alter PWTs. d, PWT measured before and after nerve injury shows clear hypersensitivity that is not reversed by injection of drug vehicle, note that local ipsilateral treatment of the neuropathic paw with OB-1 effectively normalizes PWT, but treatment of the contralateral paw does not. Note that alleviation of hypersensitivity with OB-1 treatment is indistinguishable from gabapentin treatment (*$p<0.001$; $p<0.01$; Mann-Whitney U test; numbers indicate mice treated; data are displayed as mean of individual median PWTs; error bars indicate s.e.m.). e, Measurement of PWTs over time; the maximal analgesic efficacy developed between 3 h and 9 h after local OB-1 injection (numbers indicate mice treated; data are displayed as mean of individual median PWTs). f, Dose-response relationship of OB-1 is shown, ED50=4.42 µM or approximately 20 pmol (*$p<0.001$; **$p<0.01$; *$p<0.05$; Wilcoxon Signed Rank Test; numbers indicate drug treatments; data are displayed as mean of individual median PWTs; error bars indicate s.e.m.). g, No significant change in PWT was measured in Stoml3−/− mice with CCI after local administration of OB-1. h, Stoml3 copy number derived from lumbar DRG L4-6 (two mice per preparation) determined using real-time PCR showing an ipsilateral up-regulation of Stoml3 mRNA. Note that the last two bars represent data from Stoml3−/− mice (**$p<0.01$, *$p<0.05$; Mann-Whitney U test; numbers indicate RNA preparations; data represent the mean copy number±s.e.m.).
Figure 5:
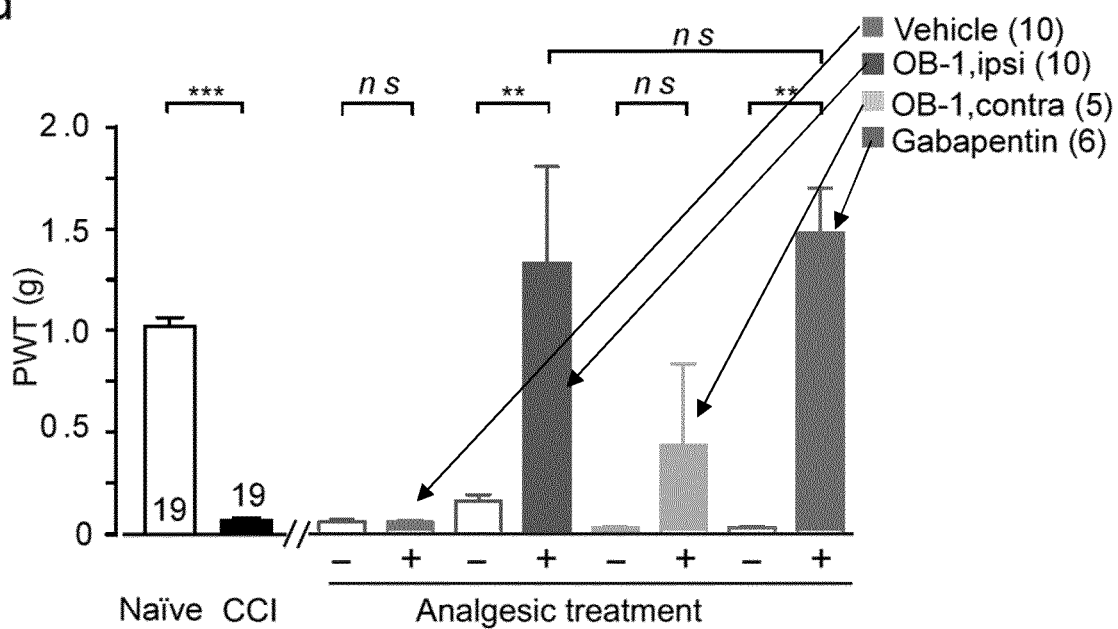
Figure 5:
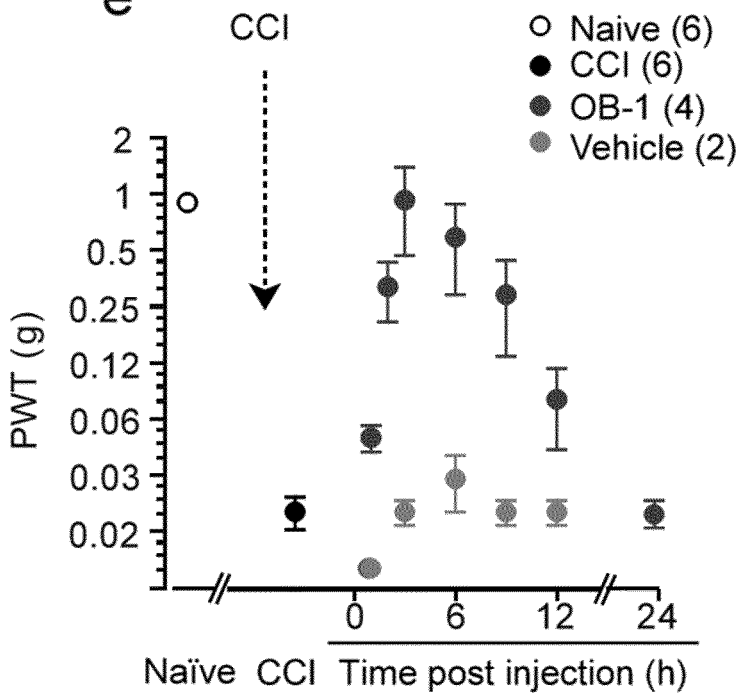
Figure 5:
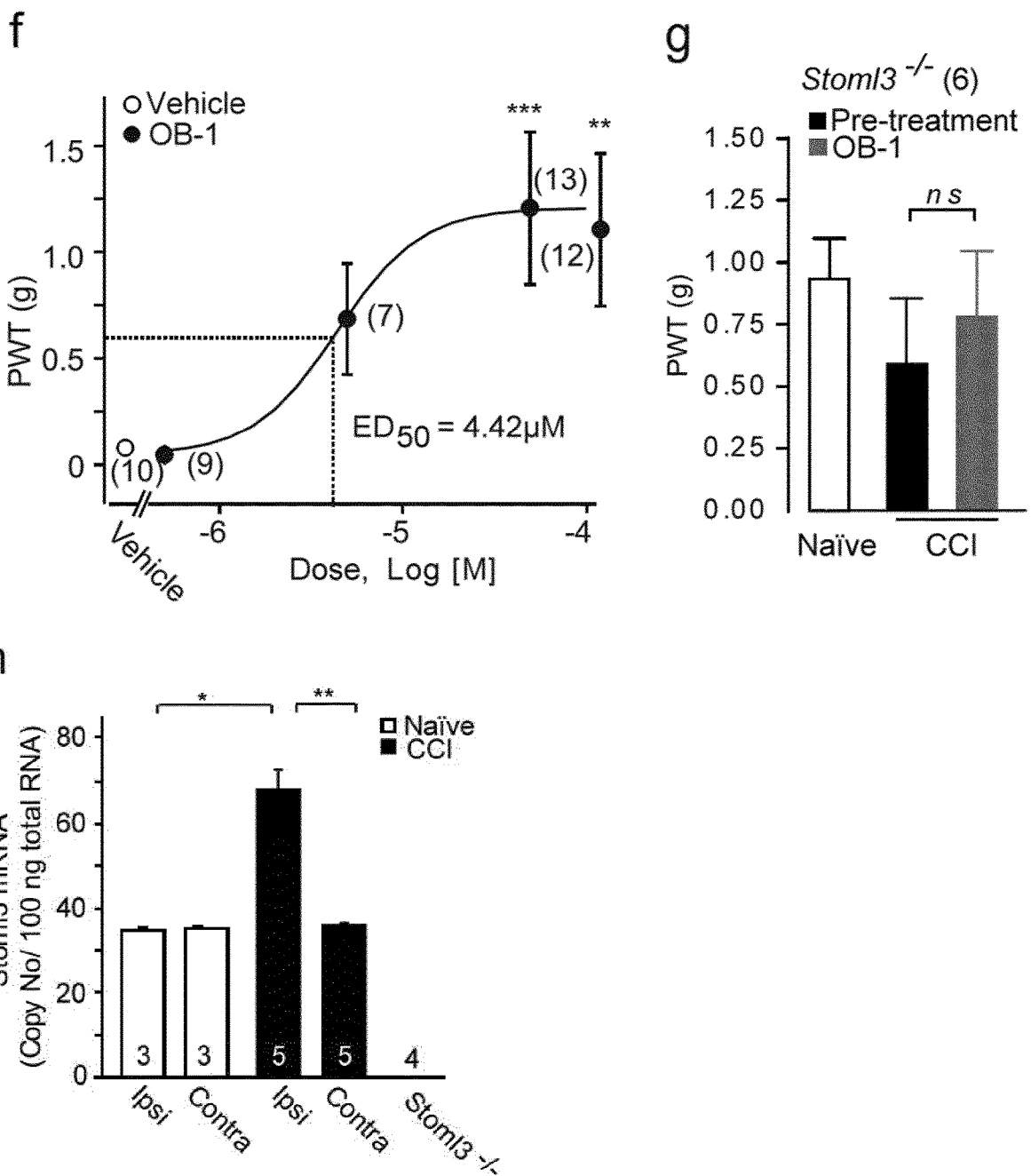

We compared behavioural performance in FIG. 5H with a two-tailed Wilcoxon Signed-Rank test (Igor Pro 6.11).

Mouse Pain Models and Behavioral Experiments:

Chronic Constriction Injury:

In deeply anaesthetized mice using isoflurane delivered in 100% O2 (Univentor 410 Anaesthesia unit; Univentor, Malta), four loose silk (5/0; Catgut GmbH Markneukirchen) ligatures were placed around the sciatic nerve at the level of the right mid-thigh as described previously (Wetzel et al., 2007).

Diabetic Neuropathy Model:

Eight week old C57Bl/6 mice were used for diabetes experiments. Diabetes was induced. Briefly, 6 consecutive intraperitoneal injections of streptozotocin (STZ, Sigma-Aldrich, #S0130) were given with 24 h intervals at 60 mg/Kg body weight in citrate buffer (0.05M, pH 4.5) to induce diabetes. Blood glucose was maintained between 400 and 500 mg/dL throughout the experimental period. Mechanical sensitivity was measured in regular intervals and only those mice showing increased sensitivity to von Frey filaments as compared with basal sensitivity were selected for testing the effects of OB-1.

Behavioral Testing:

Von Frey filaments of increasing strength (0.07, 0.16, 0.4, 0.6, 1.0 and 1.4 g) are applied 5 times with at least 1 min interval to intraplantar surface of hind paws to test the mechanical sensitivity. Stimulus was applied until the filament was bent and a sharp withdrawal of paw was considered as a positive response. Frequency of positive responses was recorded out of 5 stimuli and percent of withdrawal frequency was calculated. Threshold was calculated as the von Frey filament strength required to elicit 60% withdrawal frequency. Vehicle or OB-1 (approximately 20 μl solution, 250 pmol per paw) was injected subcutaneously into intraplantar surface of diabetic mice under mild isoflurane anesthesia and mechanical sensitivity was measured from both injected (ipsilateral) and non-injected (contralateral) paws at 4 and 24 h post-injection.

Assessing Touch Evoked Pain:

Mice were allowed to habituate to the testing apparatus (acrylic chambers 10×10 cm in size, suspended above a wired mesh grid) one hour prior to behavioral testing. Only once the subject was at rest and not moving, calibrated von-Frey hair monofilaments (Aesthesio® set of 20 monofilaments, Ugo Basil) were applied to the plantar surface of the hind paw in order to deliver target forces from 0.008 grams to 4 grams increasing in an approximately logarithmic scale. A single stimulus indicated by a slight bending of the filament lasted for two seconds unless the mouse withdrew its paw. In order to measure mechanosensitivity the up-and-down method described by Chaplan[13] was adapted as follows: Testing began with a filament delivering a target force of 0.4 g, but filaments were applied three times. A positive response was noted if the subject withdrew the paw to all three filament applications, so that the successively smaller filament was presented next. A negative response was noted if the subject did not respond to at least one of the filament presentations, in this case the successively larger filament was presented next. Paw withdrawal thresholds were calculated as median of 23 to 30 determined turning points of the particular force stimuli applied to the subject.

Drug injections of OB-1 or DMSO alone were dissolved in Ringer's solution (in mM: 135 NaCl, 5 KCl, 5 HEPES, 1.8 CaCl2), 1 MgCl2) to make the OB-1 and vehicle solution. Injections were made 3 hours prior to behavioral testing, approximately 20 μl solution, 250 pmol per paw, was injected into the palm with a Hamilton syringe, gauge 33. During the injection procedure, the mouse was anaesthetized with isoflurane (1.5 to 2.5% in O2). The injection procedure lasted around 3 minutes after which the mouse was moved to the home cage for recovery before behavioral testing.

Assessing Temperature Evoked Pain Behavior:

Tests were performed on the plantar surface of the hind paw by a focused, radiant heat light source (IITC Life Science Inc.). The light beam was focused to the top of a built-in heating base digitally controlled for consistent temperatures (here 32° C.) and created a 4×6 mm intense spot on the hind paw of the subject. The time to paw withdrawal in response to a constantly increasing heat stimulus (maximal active intensity=25% of the light source) with a cutoff of 20 seconds was determined. Heat stimuli were repeated 6 times for each paw with a stimulus interval of 1 minute.

Drug injections of OB-1 or DMSO alone were dissolved in Ringer's solution (in mM: 135 NaCl, 5 KCl, 5 HEPES, 1.8 CaCl2), 1 MgCl2) to make the OB-1 and vehicle solution. Injections were made 3 hours prior to behavioral testing, approximately 20 μl solution, 250 pmol per paw, was injected into the palm with a Hamilton syringe, gauge 33. During the injection procedure, the mouse was anaesthetized with isoflurane (1.5 to 2.5% in O2). The injection procedure lasted around 3 minutes after which the mouse was moved to the home cage for recovery before behavioral testing.

Generation of Stoml3$^{Lacz}$ mice:

The C57BL/6J mouse BAC clones (https:bacpac.chori.org) containing/Stoml3/gene was isolated from RPCI-23 library[14]. A 12-kb DNA fragment containing the exon1 and its flanking regions of Stoml3 gene was isolated by gap repair[15]. Homologous recombination in bacteria[15,16] was used to fuse an NLS-lacZ cassette to the ATG of Stoml3 and to introduce the self-excision neo cassette [17] into the Stoml3 locus. The MC1-diphteria toxin A (DTA) cassette was placed at the 3' end of the vector and was used for negative selection. Colonies of the E14.1 ES cell line (129/Ola) that had incorporated the targeting vector into their genome were selected by G418 and analyzed for homologous recombination by Southern blot analysis using 5' and 3' probes that lie outside of the targeting vector. Two clones were microinjected into C57Bl/6 blastocysts to generate chimeras that transmitted the Stoml3lacZ allele. Routine genotyping was performed by PCR (Stoml3-LacZ F: gac agt gtg atg tca ggg aag; LacZ int R: cct tcc tgt agc cag ctt tca tc; Stoml3-LacZ R: cct tgt aaa ctg ata gcg ggg ac) and, occasionally, genotypes were verified by Southern blot hybridization.

Immunohistochemistry:

Mice were perfused with ice-cold PBS until liver blanching, followed by 0.5% gluteraldehyde for 20 minutes. Lumbar DRG were dissected, post-fixed in 0.5% gluteraldehyde in PBS for 1 h at 4° C., washed several times in PBS and cryoprotected in 30% sucrose overnight at 4°. DRGs were embedded in O.C.T. Tissue-Tek (Sakura Finetek, Netherland), frozen on dry ice and stored at −80° C. Frozen embedded tissue was cut on a Cryostat CM3050S (Leica) and slides were incubated in X-gal reaction buffer (35 mM potassium ferrocyanide, 35 mM potassium ferricyanide, 2 mM MgCl2, 0.02% Nonidet P-40, 0.01% Na deoxycholate and 1 mg/ml of X-Gal) for 2 days at 37°. Slices were washed several times in PBS until the solution no longer turned yellow, air-dried and sealed with a coverslip. Sections were observed on a Zeiss Axiovert 135 microscope using Zen imaging software (Zeiss, Germany). Image J (NIH, USA) was used to manually trace the outlines of cell in order to obtain cell area.

Electron Microscopy:

Mice were perfused with freshly prepared 4% formaldehyde in 0.1 M phosphate buffer. Sciatic nerves were dissected and post-fixed in 4% formaldehyde/2.5% glutaraldehyde in 0.1 M phosphate buffer for 3 days. Following treatment with 1% OsO4 for 2 h, they were dehydrated in a graded ethanol series and propylene oxide and embedded in Poly/Bed$^R$ 812 (Polysciences, Inc., Eppelheim, Germany). Semithin sections were stained with toluidine blue. Ultrathin sections (70 nm) were contrasted with uranyl acetate and lead citrate and examined with a Zeiss 910 electron microscope. Digital images were taken with a 1 k×1 k high-speed slow scan CCD camera (Proscan) at an original magnification of 5600×. The imaging was done by Bettina Purfürst at the MDC electron microscopy core facility.

Identification of Small Molecule STOML3 Inhibitors

Figure 1:
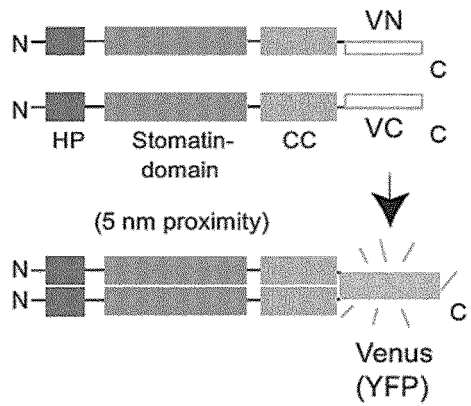
FIG. 1: Screening for small molecules that modulate STOML3 oligomerization. a, Schematic representation of BiFC analysis of protein-protein interactions used for small molecule screen. b, Signal development observed when STOML3-VC was used as prey and VN-tagged STOML3 variants that do not properly oligomerize were used as bait (normalized slope of BiFC signal development, data represents mean±s.e.m. of triplicates). The slope of signal development was used as a measure of oligomerization (normalized slope of BiFC signal development, data are displayed mean±s.e.m.). c, Structures of hit compounds, the oligomerization blockers, OB-1 and OB-2. d, e, Normalized slope of BiFC signal development in cells overexpressing Mus musculus or Homo sapiens STOML3 in the presence of OB-1 and OB-2 is shown; data are displayed mean±s.e.m. f, Representative reconstructed dSTORM images of STOML3-FLAG overexpressed in N2A cells. g, Distribution of STOML3-FLAG domain size as detected by dSTORM imaging. Each data point represents a single cell; for each cell the FHWM of 100 randomly chosen domains was measured ($p<0.01$; *$p<0.001$; Student's t-test).
Figure 1:
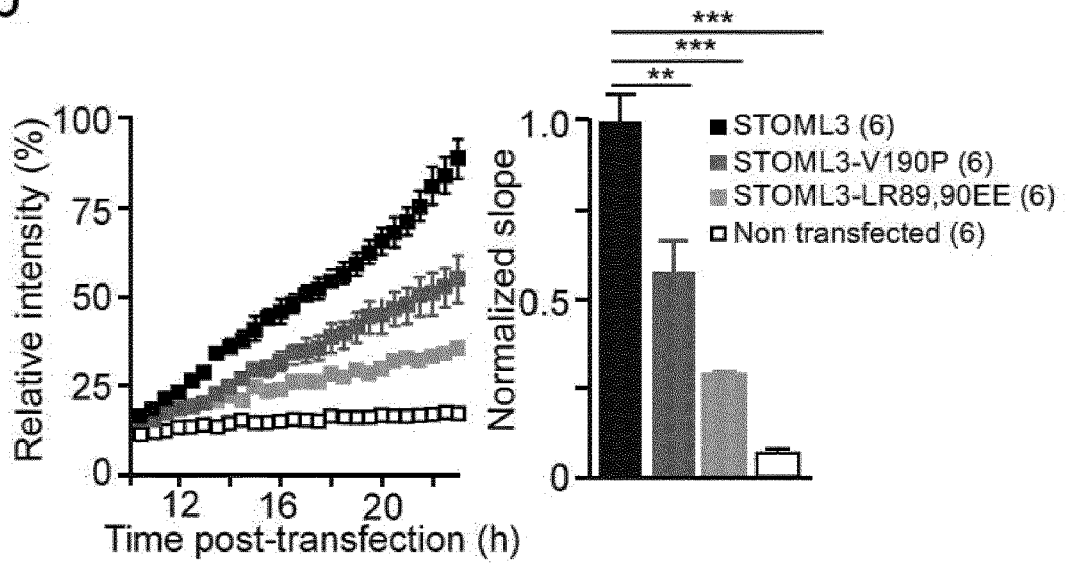
Figure 1:
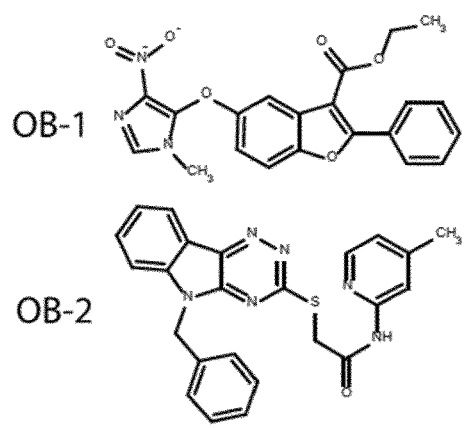
Figure 1:
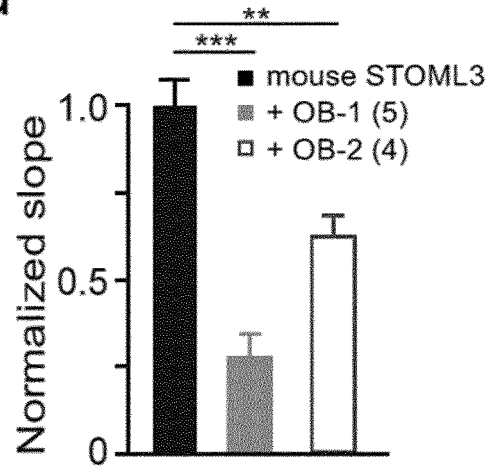
Figure 1:
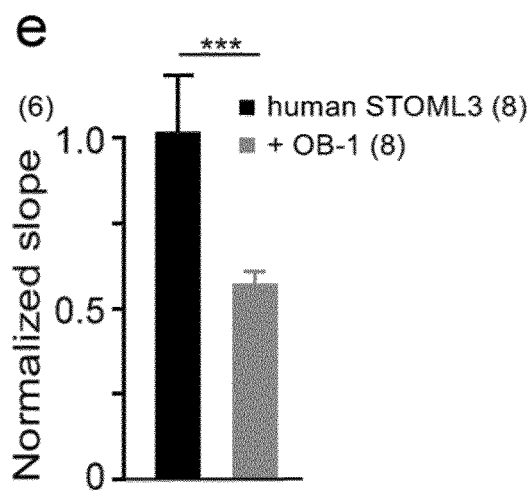
Figure 1:
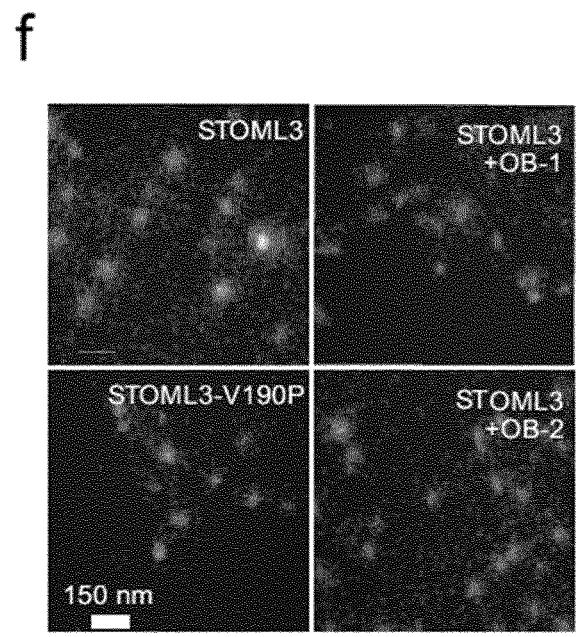
Figure 1:
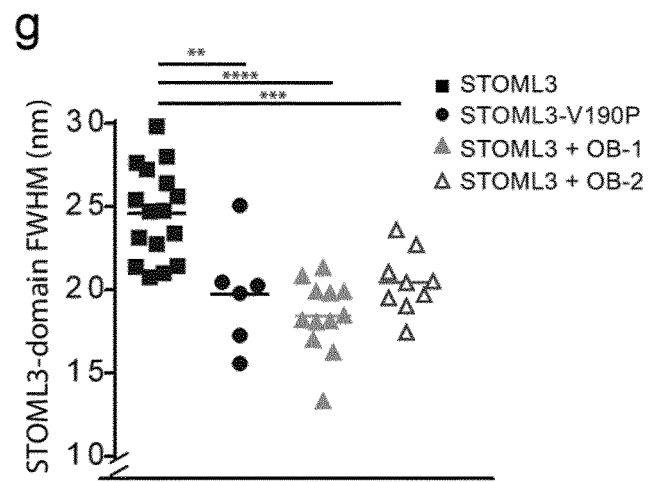
Figure 8:
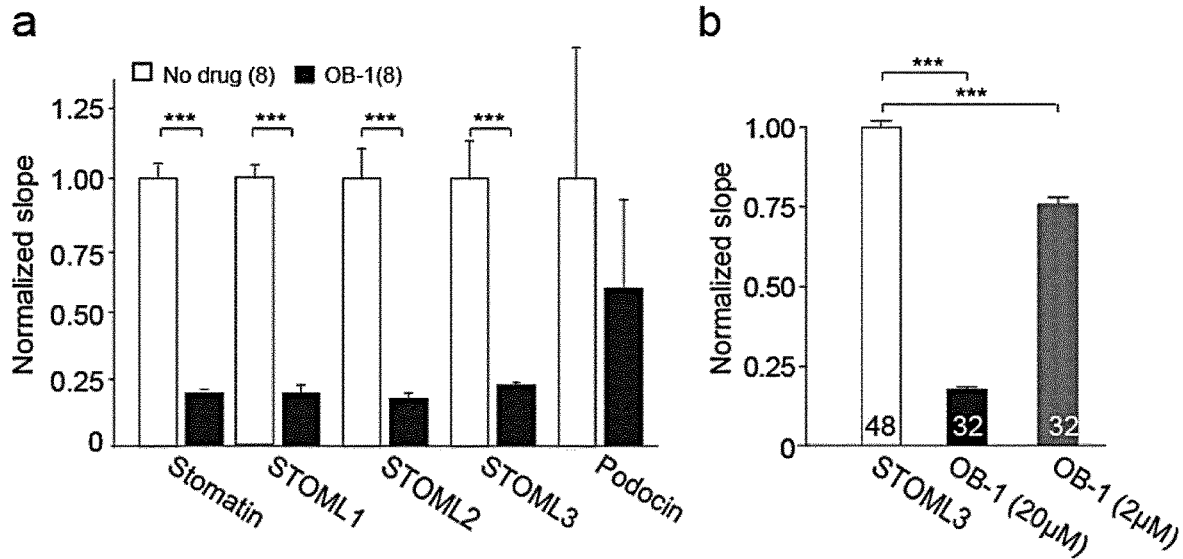
FIG. 8: Effects of STOML3 modulating molecules on other Stomatin-domain proteins. (a) BiFC signal development observed when cells were transfected with Stomatin-VC/-VN, STOML1-VC/-VN, STOML2-VC/-VN, STOML3-VC/-VN or Podocin-VC/-VN expression constructs respectively. Note that OB-1 significantly inhibits oligomerization of Stomatins ($p<0.005$, Mann Whitney test) but does not affect with Podocin. (b) OB-1 was tested at two different concentrations (2 µm and 20 µm) using the BiFC assay where wild type STOML3 was used as both bait and prey. In comparison with controls the normalized slope calculated from the signal development data are presented and was significantly reduced when OB-1 was present (Student's t-test, $p<0.001$).

In mammals STOML3 belongs to a family of five structurally conserved membrane proteins, including stomatin, STOML1, STOML2, and podocin[10,12-16], all of which self-associate via their stomatin-domain (FIG. 8a)[10]. Self-association of stomatin-domain proteins can be monitored in HEK293 cells using Bimolecular Fluorescence Complementation (BiFC) whereby N- and C-terminal halves of the YFP molecule are tagged to the prey and bait protein STOML3[2,17] (FIG. 1a). Irreversible association of the YFP fragments produces fluorescence that increases linearly over time (FIG. 1b). Mutations in one STOML3 pair that disrupt oligomerization (V190P or LR89,90EE) significantly reduce the rate of signal development (FIG. 1b)[2,10]. We used this cellular assay in a high throughput format to screen for small molecules that significantly inhibit the BiFC signal, a measure of STOML3 self-association. In a primary screen of about 35000 small molecules (each at 10 M), obtained from the central compound collection of the Leibniz Institute for Molecular Pharmacology screening unit, 21 molecules were found to reproducibly decrease STOML3 self-association based on the slope of YFP signal development. The two most effective inhibitory compounds were designated Oligomerization Blocker 1 and 2, (OB-1 and OB-2) (FIG. 1c,d). In further BiFC assays, the STOML3 oligomerization blocker, OB-1 was an effective inhibitor of the self-association of stomatin, STOML1, STOML2, but not podocin (FIG. 8a). Lower OB-1 concentrations (2 M) also inhibited the BiFC signal (FIG. 8b). The OB-1 molecule was also re-synthesized and exhibited the same activity in the BiFC assay as the commercially available sample. The human STOML3 peptide sequence is 92% identical to that of the mouse and 100% identical in the core stomatin-domain and this sequence tested in our BiFC assay also showed self-association (FIG. 1e). More importantly for clinical development self-association of the human STOML3 protein was also inhibited by OB-1 (FIG. 1e).

STOML3 Oligomerization Dictates Domain Size in the Plasma Membrane

Figure 9:
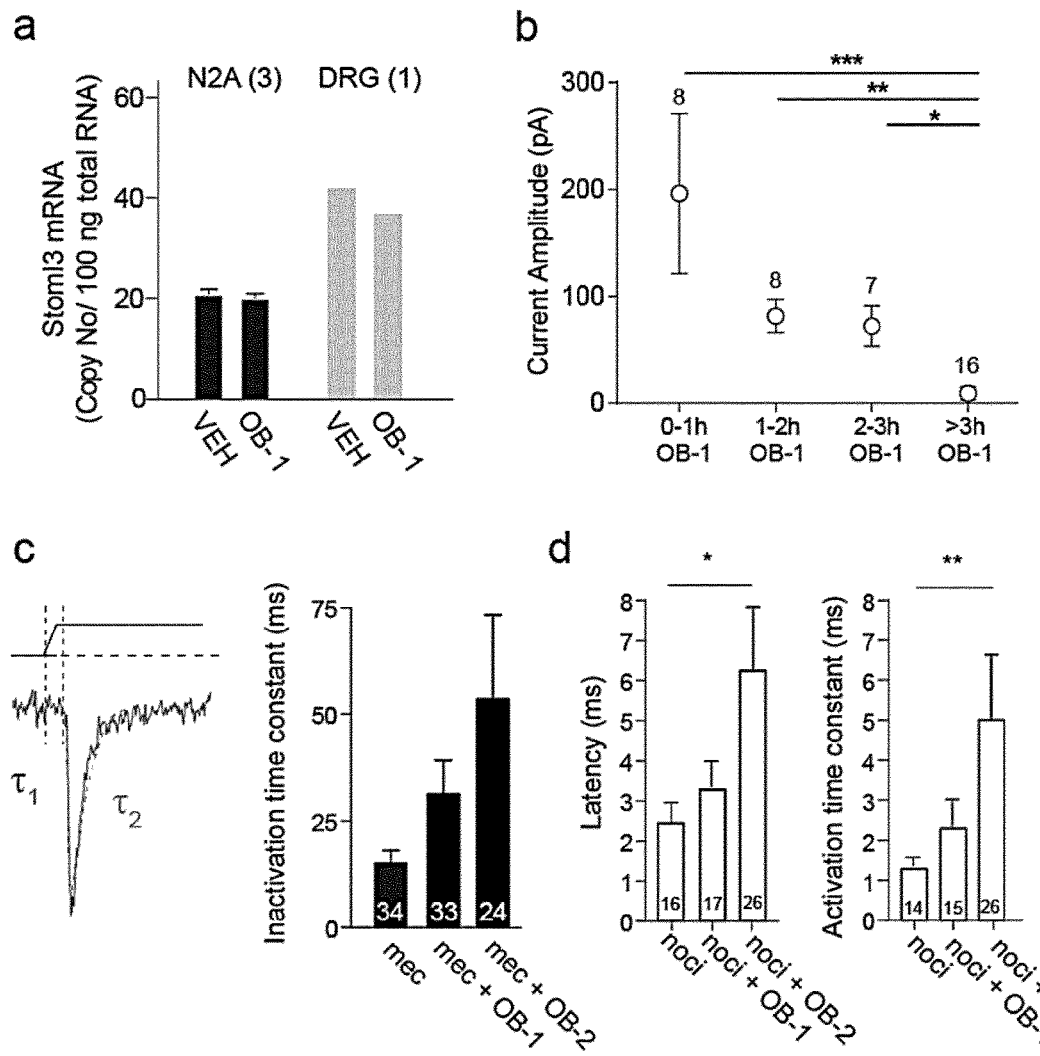
FIG. 9: Stoml3 mRNA levels after inhibitor treatment and quantitative analysis of mechanically gated currents. (a) N2A cells and acutely isolated DRGs were treated with either vehicle or OB-1 (20 µM) for 3 hours before mRNA was isolated, reverse transcribed and analysed using qPCR. There were no detectable differences in Stoml3 transcript levels. (b) Time course analysis of OB-1 activity in N2A cells. Cells were treated with 20 µM OB-1 for between 0-3 hours and mechanotransduction was monitored using pillar arrays. Treatment of 3 hours was required for maximum inhibition of mechanically-gated currents. (c) Representative current trace with latency (magenta) activation time constant (τ1, blue) and inactivation time constant (τ2, green) indicated by dashed lines. The inactivation time constant of mechanically gated currents in DRG mechanoreceptors (mec) is shown measured using elastomeric pillar arrays. There is a trend for longer inactivation time constants that is not significant. (d) In nociceptors (noci) treatment with OB-2 led to significantly longer latencies and significantly slower activation time constants. Number of currents indicated on graph; data is mean±s.e.m.
Figure 10:
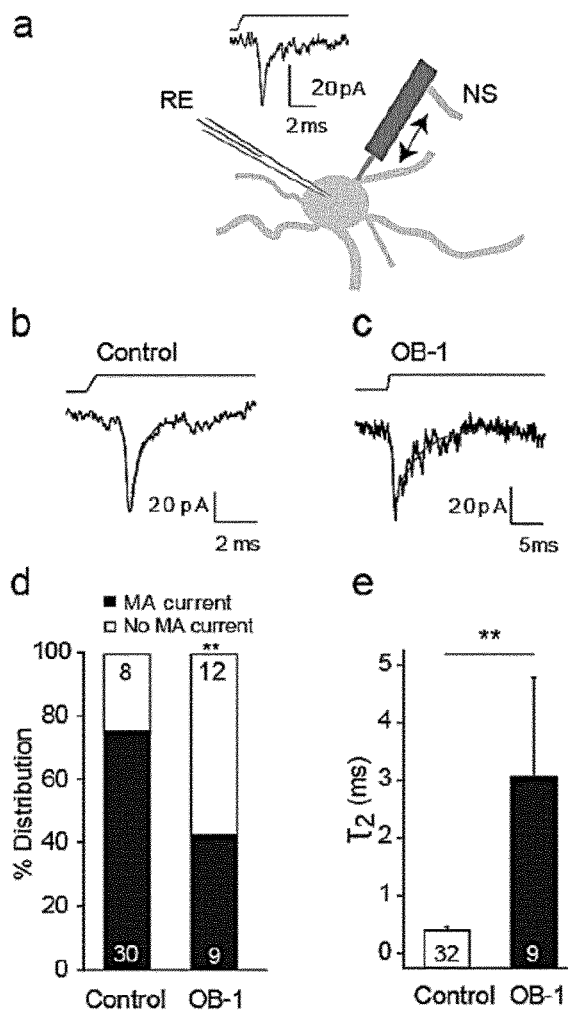
FIG. 10: Effects of OB-1 on mechanically-activated currents in mouse sensory neurons. (a) Schematic diagram of a large diameter mouse sensory neuron with recording electrode (RE) and nanostimulator (NS). (b) Typical RA-mechanosensitive current evoked from poking the cell soma (c) Typical RA-mechanosensitive currents evoked from neurons pre-incubated with OB-1 or vehicle (control). Red lines indicate the exponential fit of the current inactivation to determine □2 (d) Distribution of cells found with and without a mechanically-activated current (MA current) in both groups. Note significant loss of mechanically-activated currents in OB-1 treated neurons (p<0.01 compared to control, Fishers's exact test). (e) The mean inactivation time constants (τ2) of mechanically-gated currents, note the slowed τ2 in OB-1 treated neurons.

We next determined whether OB-1 and OB-2 modulation of STOML3 oligomerization state influences clustering of the protein in the plasma membrane. We used super-resolution dSTORM microscopy[18-20] to visualize FLAG-tagged STOML3 at the plasma membrane of transfected N2A cells. Using dSTORM we could show that STOML3 was present in microdomains at the plasma membrane (FIG. 1f). The size of the STOML3 clusters was variable (full width at half maximum, FWHM=24.6±2.8 nm, mean±s.d.) but these domains may contain more than one STOML3 dimer[10]. Introduction of the V190P mutation disrupts oligomerization of STOML3 and abolishes its ability to modulate the mechanosensitivity of Piezo1 channels[2]. This STOML3 variant exhibited significantly smaller clusters in the plasma membrane (FIG. 1f,g), demonstrating that by disrupting STOML3 oligomerization we can manipulate and measure nanoscale changes in STOML3 cluster size. Pre-incubation of N2A cells expressing STOML3-FLAG with OB-1 or OB-2 for three hours led to significantly reduced STOML3-FLAG cluster sizes compared to vehicle treated cells (FIG. 1e,f). The effects of OB-1 did not reflect changes in the levels of Stoml3 mRNA in these cells (FIG. 9a). Thus we obtained independent support that OB-1 and OB-2 reduce STOML3 oligomerization state, an important consequence of which is a reduced STOML3 cluster size at the plasma membrane.

STOML3 Inhibitors Modulate Mechanotransduction Currents

Figure 2:
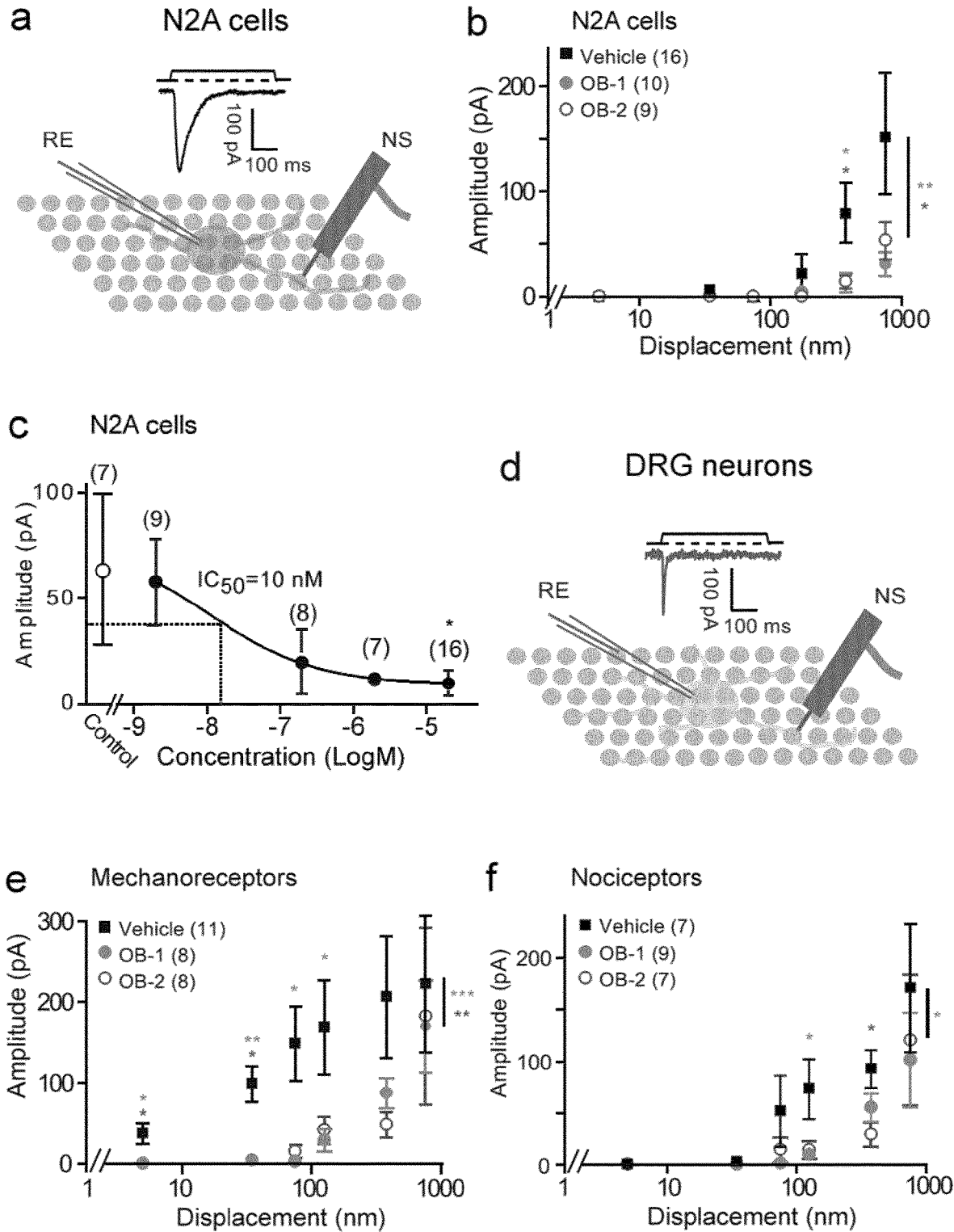
FIG. 2: Quantitative analysis of the effect of hit compounds on mechanotransduction. a, Schematic of pillar array analysis of mechanotransduction in N2A cells. b, Stimulus-response curves for N2A treated with either OB-1 or OB-2; both compounds significantly inhibit mechanically-gated currents in N2A cells (number of cells indicated on graph; OB-1 **$p<0.01$, OB-2 *$p<0.05$; two way ANOVA). c, Hill plot of the concentration dependence of the OB-1 effect on the Piezo1 current in N2A cells, (*$p<0.05$; Mann-Whitney U test; numbers indicate cells recorded, data are displayed as mean of individual bins±s.e.m.). d, Schematic of pillar array analysis of mechanotransduction in acutely prepared DRG neurons. e, Stimulus-response curves for mechanoreceptors treated with either OB-1 or OB-2; both compounds significantly inhibit mechanically-gated currents activated by pillar deflections less than 50 nm, OB-1 significantly inhibits currents gated by deflections up to 250 nm (data displayed as mean±s.e.m., numbers of cells indicated on graph, OB-1 *$p<0.001$, OB-2 $p<0.01$; two way ANOVA). f, Stimulus-response curves for nociceptors treated with either OB-1 significantly inhibit mechanically-gated currents in these cells (numbers indicate cells recorded, data are displayed as mean of individual bins±s.e.m; OB-1 *$p<0.05$; two way ANOVA). g-i, In the presence of OB-1 there was no detectable difference in action potentials generated by current injection in either (h) mechanoreceptors or (i) nociceptors (ns; Mann-Whitney U test (Mechanoreceptors), Student's t-test; numbers indicate cultivated neurons recorded; data are displayed as mean of individual bins±s.e.m).
Figure 2:
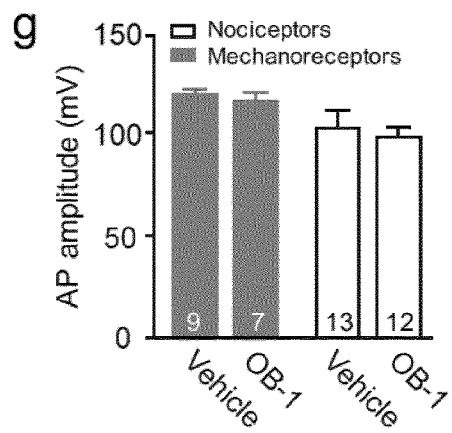
Figure 2:
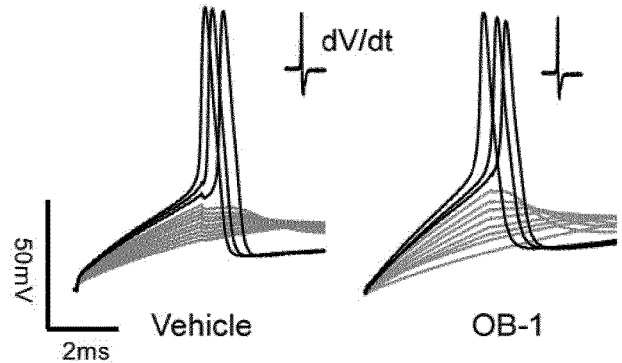
Figure 2:
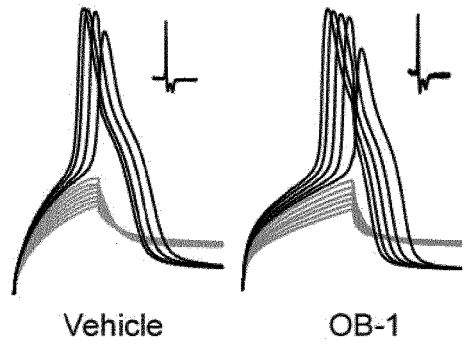

Endogenously expressed STOML3 in N2A cells is required to maintain Piezo channel sensitivity to membrane deflection[2]. By precisely deflecting defined areas of the membrane-substrate interface using a pillar array we could activate Piezo1 currents in N2A cells with displacements ranging from 100-1000 nm (FIG. 2a). Both OB-1 and OB-2 reduced the sensitivity of mechanosensitive currents to pillar deflection (FIG. 2b). Pre-incubation of cells with OB-1 for periods of between 1 and 3 h reduced Piezo1 current amplitudes, but the effect was only maximal after 3 h (FIG. 9b). Recording mechanically-activated currents in the presence of different concentrations of OB-1 revealed a steep concentration dependence with a calculated $IC_{50}$ of 10 nM, Hill coefficient 0.6 (FIG. 2c).

Figure 11:
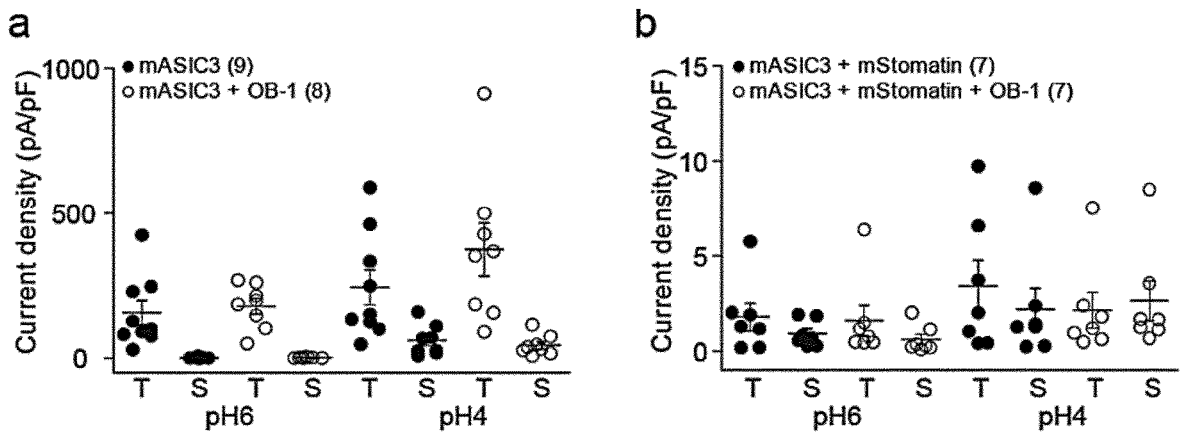
FIG. 11: OB-1 has no effect upon ASIC3-mediated currents, nor stomatin inhibition of ASIC3. (a) Neither the transient (T), nor sustained (S) phases of pH-evoked currents in CHO cells expressing ASIC3 were inhibited by OB-1 (20 μm). (b) Stomatin inhibits ASIC3-mediated pH gated currents, which is not modulated by OB-1.
Figure 12:
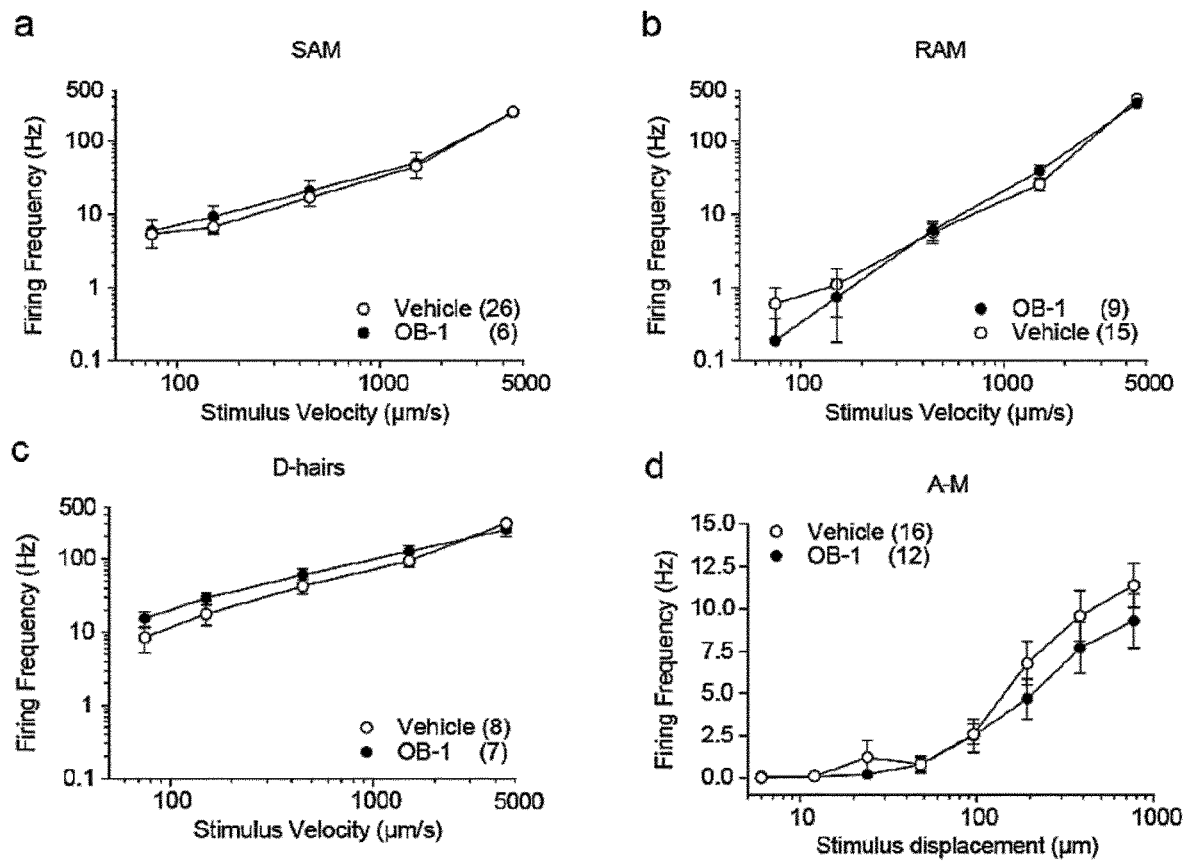
FIG. 12: Non silenced mechanoreceptors are functional after OB-1 treatment. (a-d) Receptive field properties of single cutaneous afferents in control and OB-1 treated skin are shown. Series of ramp and hold stimuli with increasing velocities (0.075, 0.15, 0.45, 1.5 and 15 mm/s at 92 μm displacements) were applied to low threshold mechanoreceptors, i.e. slowly adapting mechanoreceptors (SAM) (a), rapidly adapting mechanoreceptors (RAM) (b) and D-hairs (c). Mean firing frequencies during the ramp phase were plotted as function of stimulus velocity; numbers indicate fibers recorded; data are displayed as mean number of action potentials±s.e.m. (d) An ascending series of displacements (32-1024 μm) using a constant stimulus velocity was applied to A-mechanonociceptors (AM). Mean firing frequencies were plotted as function of displacement amplitudes showing no changes in mechanosenitivity in AMs. Numbers indicate fibers recorded; data are displayed as mean number of action potentials±s.e.m.
Figure 13:
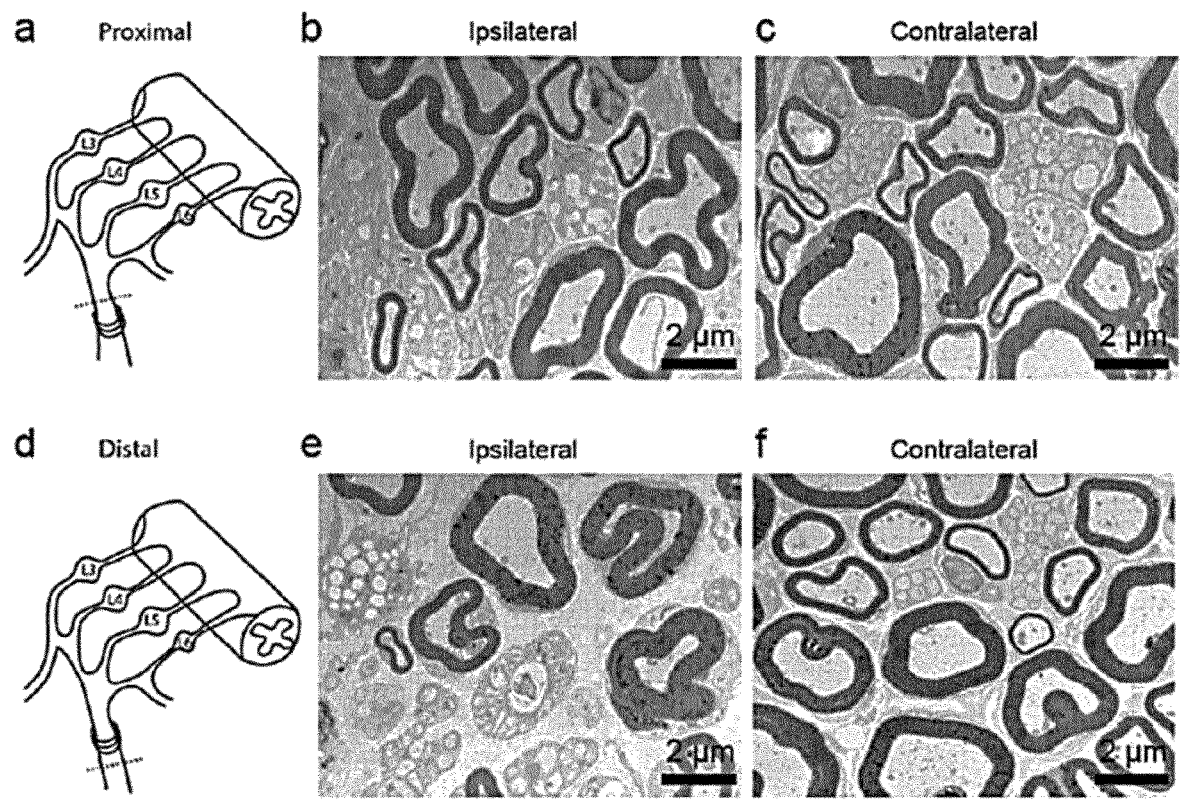
FIG. 13: Ultrastructure of the Sciatic nerve after unilateral CCI and effects of OB-1. (a, d) Schematic drawings of the section plane. (b-f) High magnification electron micrograph images of the ipsilateral or contralateral side proximal and distal to the ligation. Myelinated and unmyelinated nerve fibers showing normal ultrastructure and intact myelin sheaths or Remak bundles (c, f) demyelination and axonal degeneration was observed ipsilateral to the nerve injury (b, e). Many myelinated axon remained intact showing no demyelination or mitochondrial swelling proximal to the injury.

We evaluated the effects of OB-1 and OB-2 on mechanosensitive currents in acutely cultured mouse sensory neurons. Neurons were classified on the basis of their AP configuration as mechanoreceptors or nociceptors[2,21]. We found that mechanically gated currents in mechanoreceptors start to activate with membrane deflections of <50 nm², but this sensitivity was substantially reduced after exposure to OB-1 or OB-2 (FIG. 2d,e). Thus significant mechanically gated currents were only observed in OB-1 or OB-2 treated cells with deflections that exceeded 100 nm. The threshold for activation of mechanosensitive currents in nociceptive sensory neurons is normally considerably higher than that found in mechanoreceptors[2] a finding that we have reproduced here (FIG. 2f). However, we also observed that OB-1 or OB-2 treatment produced a significant reduction in the amplitude of mechanically gated currents in nociceptors with stimulus magnitudes between 100 and 500 nm (FIG. 2f). In addition the latency for mechanically gated currents as well as the activation time constant for current activation $\tau_1$ was significantly slowed in nociceptors after treatment with OB-2 (Supplementary FIG. 2c,d). The exposure of sensory neurons to OB-1 for 3 hours did not lead to any changes in the level of Stoml3 transcripts (FIG. 9a), suggesting that the compounds tested herein do not work by regulating gene expression, or transcript stability. Cell soma indentation can also be used to evoke so called Rapidly-adapting currents (RA-currents, inactivation constant $1_2$<5 ms) in mechanoreceptor sensory neurons[21,22] and after exposure to OB-1~60% of the neurons (12/21 neurons) displayed no mechanosensitive current compared to control or vehicle treated neurons (21%, 8/38 neurons), this effect was statistically significant (Fisher's exact test p<0.01 FIG. 10a-e). Neither of the two compounds tested had any discernable effects on voltage-gated currents or membrane excitability as evidenced by the fact that APs were of normal amplitude and shape after treatment (FIG. 2h,i). For example, cultured sensory neurons treated for at least 3 h with 20 μM OB-1 displayed no alteration in a number of parameters indicative of electrical excitability (FIG. 2g-i, Table 1). In summary, using two independent assays we found that OB-1 is a strong inhibitor of native mechanosensitive currents. Stomatin-domain proteins can also negatively regulate members of the acid sensing ion channel family (ASICs) in a subunit-specific manner[6,10,23,24] However, OB-1 had no detectable effect on the negative modulation of ASIC3 mediated currents by mouse stomatin (FIG. 11).

A STOML3 Inhibitor can Silence Touch Receptors

Many cutaneous mechanoreceptors in Stoml3$^{-/-}$ mice innervate the skin, but cannot be activated by mechanical stimulation[5,6]. We made subcutaneous injections of the OB-1 compound (250-500 pmol per paw) into the hairy skin of the mouse lateral foot innervated by the saphenous nerve and recorded from sensory afferents 3 h later using an ex vivo skin—nerve preparation[5,25]. In wild type mice the vast majority of myelinated and unmyelinated fibers are mechanosensitive[4-6], demonstrated by tracing the spike evoked by local electrical stimulation of nerve branches and then searching for the nearby mechanosensitive receptive field (FIG. 3a). In contrast, in skin pre-treated with OB-1 over 40% of Aβ-fibers (19/44) lacked a mechanosensitive receptive field, and this was significantly different from vehicle-injected controls where less than 7% (5/69 fibers) were found to be insensitive to mechanical stimuli, p<0.001 Fischer's exact test (FIG. 3a).

Amongst the Aβ-fibers we also observed an increase in the proportion of fibers for which no mechanosensitive receptive field could be found (21%, 8/38 fibers compared to 5%, 1/18 fibers in controls, but this was not significantly different; Fischer's exact test, p>0.14). There was also no change in the proportion of C-fibers that lack a mechanosensitive receptive field (FIG. 3a). We next examined the physiological properties of the remaining mechanosensitive afferents in OB-1 treated skin. However, the proportion of mechanoreceptor types found, as well as the mechanosensitivity of the remaining Aβ-fiber mechanoreceptors (Rapidly and Slowly adapting mechanoreceptors, RAMs and SAMs) was unchanged compared to controls (FIG. 3b-f, FIG. 12). The mechanoreceptor silencing effect of local OB-1 treatment was completely reversible as recordings from afferents 24 h after treatment revealed no significant loss of mechanosensitivity, also compared to vehicle treated skin (FIG. 3a). Thus, a STOML3 oligomerization inhibitor can specifically and reversibly silence touch receptor activity without modifying axonal excitability.

Although, we found no evidence that C-fiber nociceptors are silenced by OB-1 treatment (FIG. 3a) we did note a statistically significant effect of local OB-1 treatment on the mechanosensitivity of C-fiber afferents that respond to both thermal and mechanical stimuli (C-mechanoheat fibers, C-MH, Two-way ANOVA, p<0.05) (FIG. 3c). C-mechanoheat fibers also displayed significantly elevated mechanical thresholds for activation that were on average almost twice that of control fibers (196.5±35.6 mN in OB-1 treated skin vs 106.9±17.4 mN in vehicle treated skin, Mann-Whitney U test, p<0.05) as measured using a force measurement system attached to the stimulus probe (FIG. 3d). The firing rates of C-mechanonociceptors (C-Ms) that lack heat sensitivity, to suprathreshold mechanical stimuli were not significantly attenuated in OB-1 treated skin (FIG. 3e,f).

Touch Perception is Attenuated by Local OB-1 Treatment

Figure 4:
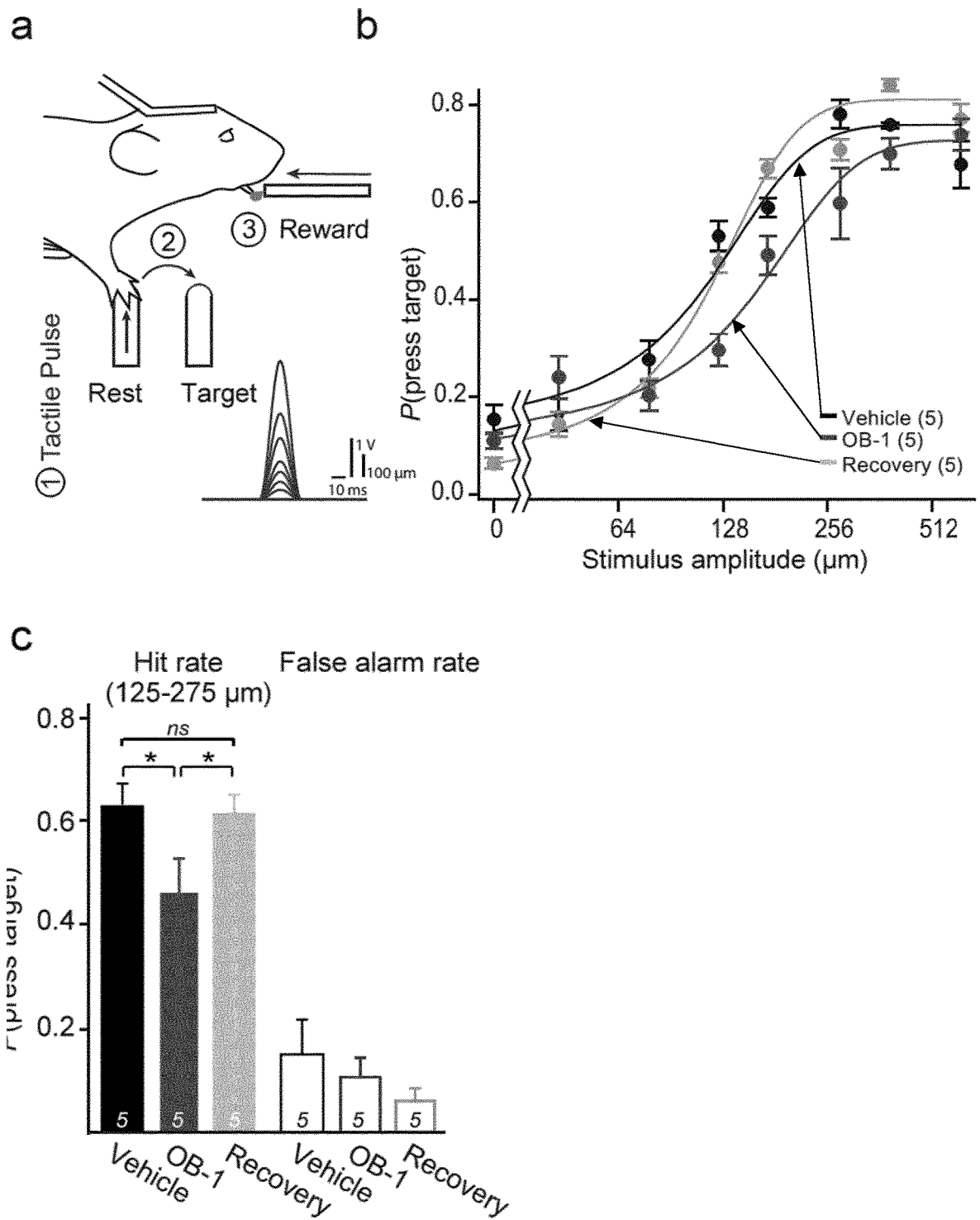
FIG. 4: OB-1 reduces the touch perception in mice. A tactile perception task for head-restrained mice. a, Mice were trained to report a single tactile pulse stimulus (inset shows stimulus voltage command pulse for all 8 amplitudes). Trial structure: mice were trained to (1) hold the rest sensor and wait for a stimulus; (2) on detection of the stimulus reach and press the target sensor within 500 ms from stimulus onset; (3) obtain water reward by licking providing it was a successful trial. b, Psychometric curves to different amplitude tactile stimuli are affected by injection of OB-1 into forepaw. Curves were constructed with a sigmoid fitting of the mean hit rates to 7 different amplitudes of tactile stimuli and a no stimulus trial (false alarm). Three conditions are displayed, injection of the vehicle (black), injection of OB-1 (magenta) and a recovery session with no prior injection (grey). c, OB-1 application to forepaw attenuates perception of near threshold tactile stimuli. Grouped hit rates to 3 threshold amplitude values (125, 175 and 275 µm) from 5 mice were significantly reduced after OB-1 injection as compared to hit rates after vehicle injection or on recovery session without prior injection. Statistical tests were made on hit rates after subtraction of the corresponding false alarm rates (*$p<0.05$; Wilcoxon Signed Rank Test; numbers indicate mice treated, data are displayed as average of individual hit rates of each mouse, grouped for 3 amplitudes±s.e.m.).

We used a tactile perception task in head-restrained mice to assess the effects of OB-1 on touch sensation. Water-restricted mice were trained to press a sensor with their forepaw within 500 ms after the onset of a 30 ms cosine mechanical stimulus applied to the same paw. Correct responses were rewarded with water. Mice learned this task to a high degree of reliability after a 10 day training period (FIG. 4a). Different stimulus amplitudes were then used to determine a psychometric curve for each mouse (FIG. 4a,b). We next injected the drug vehicle solution into the forepaw and obtained a new psychometric curve for each mouse 3-5 hours later. On the next day, the forepaw was injected with the OB-1 compound (11 nmol per paw) followed by behavioral testing. At least 24 h after the OB-1 testing day, the recovery behavior was tested without any prior injection. Following OB-1 treatment the psychometric curve was shifted to the right for stimulus strengths between 125-275 μm indicating less reliable stimulus detection (Wilcoxon Signed Rank Test, vehicle vs OB-1, p=0.026; OB-1 vs recovery, p=0.0043) (FIG. 4b,c). Vehicle treatment produced no significant change in the psychometric curve (Wilcoxon Signed Rank Test, control vs vehicle p=0.30). The detection rates of threshold stimuli returned to pre-treatment levels 1-4 d after drug treatment (Wilcoxon Signed Rank Test, vehicle vs recovery, p=0.12). These data indicate that silencing of a subset of mechanoreceptors via STOML3 inhibition is sufficient to reduce the reliability of near threshold touch perception in mice.

Peripheral STOML3 Blockade Reverses Tactile Allodynia

Neuropathic pain is a debilitating condition in which intense pain can be initiated by merely brushing the skin, activating low-threshold mechanoreceptors[7-9,26,27]. We used the chronic constriction injury model (CCI), which involves direct damage to sciatic nerve axons (FIG. 13a-f) that innervate the hypersensitive plantar hindpaw skin. Baseline paw withdrawal thresholds in wild type and Stoml3$^{-/-}$ mice did not differ, as measured with von Frey hairs using an adapted up-down method[28] (FIG. 5a). However, after induction of a unilateral CCI[9], paw withdrawal thresholds dropped profoundly in wild type mice but were only moderately reduced in Stoml3$^{-/-}$ mice, Two-way ANOVA, p<0.001 (FIG. 5a). It is well described that thermal hyperalgesia also accompanies neuropathic injury[7,9,29], a phenomenon that we also observed. However, the heat hyperalgesia observed in Stoml3$^{-/-}$ mice was identical to that in wild type controls (FIG. 5b).

We next interrogated whether local application of OB-1 can ameliorate tactile-evoked pain behavior in neuropathic models. We found no change in paw withdrawal thresholds to mechanical stimuli or withdrawal latency for radiant heat stimuli in the paws of naïve mice treated with an intraplantar dose of OB-1 (250-500 pmol per paw) (FIG. 5c). However, when we applied an intraplantar dose of OB-1 to the paws of wild type mice with established neuropathic pain (CCI model 6-21 days after induction) we observed a complete reversal of the tactile-evoked pain or allodynia, p<0.001; Mann-Whitney U-test (FIG. 5d). The reversal of tactile allodynia observed with local OB-1 treatment was indistinguishable from that found with systemic gabapentin treatment (FIG. 5d), a standard, centrally acting drug, in clinical use for the treatment of neuropathic pain[30]. We also applied OB-1 to the contralateral paw at the same concentration that was effective at reversing allodynia present in the paw ipsilateral to the injury, but observed no reversal of established hypersensitivity (FIG. 5d). These results strongly suggest that the actions of OB-1 in reversing hypersensitivity are due to inhibition of sensory neuron mechanotransduction in the skin and not to systemic or central actions. The effects of a single OB-1 dose became maximal 3 h after the injections and wore off slowly over the next 12 h so that the effect was absent after 24 h (FIG. 5e). Using a series of OB-1 concentrations we could determine a half-maximal effective dose (ED$_{50}$) of 4.42 μM (or approximately 20 pmol per paw) (FIG. 5f). We assume that local application of OB-1 reverses mechanical hypersensitivity after CCI primarily by inhibiting STOML3 oligomerization. We decided to test this idea more directly by testing the effects of local OB-1 on the mechanical sensitivity of Stoml3$^{-/-}$ mice with CCI. Mechanical hypersensitivity following CCI is much less prominent in Stoml3$^{-/-}$ mice (FIG. 5a,g) but we observed no change in paw withdrawal threshold after treatment of neuropathic paws of Stoml3$^{-/-}$ mice with OB-1 (FIG. 5g). Off-target effects are an issue for any biologically active small molecule. We therefore tested the effects of 20 μM OB-1 in a commercially available in vitro pharmacology panel (www.cerep.fr) consisting of 79 receptors and ion channels. Significant inhibition of specific ligand binding to the selected receptors was seen in a few cases (6/79), but there is at present no data implicating any of these receptors in peripheral nociception. The agreement between the in vitro and in vivo effects of STOML3 inhibition and the results of genetic ablation of the Stoml3 in the mouse suggest that OB-1 exerts its biological effects primarily on STOML3. The remarkable protection from touch-evoked pain in animals lacking STOML3 led us to hypothesize that the nerve injury may itself lead to a change in the levels of Stoml3 mRNA expression in the DRG. Up-regulation of STOML3 could in turn exacerbate touch-evoked pain by enhancing the sensitivity of mechanotransduction in injured sensory afferents. Using real-time quantitative PCR we measured a doubling in Stoml3 mRNA expression levels (mRNA copy no. 68.5±4.6) in the lumbar DRGs that project axons to the ligation site compared to the control uninjured side (35.2±3.6, p<0.01; Mann-Whitney U-test) (FIG. 5h).

Figure 14:
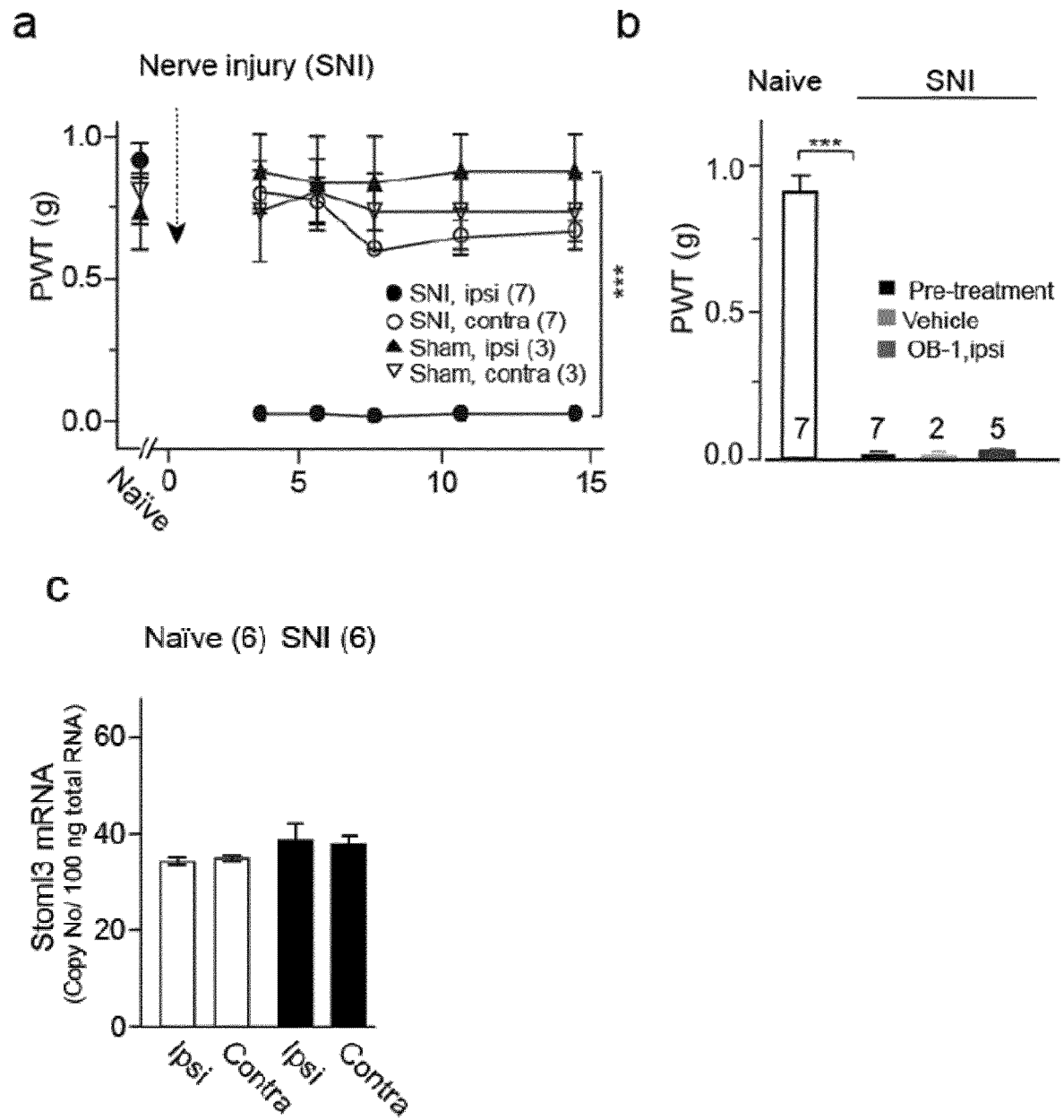
FIG. 14: OB-1 treatment in additional pain models. (a) Development of tactile-evoked pain using the spared nerve injury (SNI) model. Paw withdrawal thresholds (PWTs) are displayed; note that wild type mice develop a prolonged tactile-evoked pain ipsilateral to the injury. (b) PWTs are displayed, showing no alleviation of tactile-evoked pain behavior after local OB-1 treatment. (c) Stoml3 copy number derived from lumbar DRG L4-6 (two mice per preparation) determined using real-time PCR showing no up-regulation of Stoml3 mRNA after SNI. (d-g) A single dose of NGF (1 μg/g body weight) was injected i.p. into adult mice to induce hyperalgesia in wild type and Stoml3−/− mice. (d, e) PWT or paw withdrawal latencies (PWL) are displayed before and after NGF-induced hyperalgesia in wild type and Stoml3−/− mice showing that prominent symptoms of thermal and mechanical hyperalgesia were not different between the genotypes. (f, g) Both, PWTs and PWLs were measured in response to OB-1 before and after systemic NGF-injection, note that OB-1 does obviously not alleviate NGF-induced mechanical (g) or thermal (h) hyperalgesia. (***p<0.001; Two-way ANOVA; numbers indicate mice examined; data are displayed as mean of individual median PWTs; error bars indicate s.e.m.).
Figure 14:
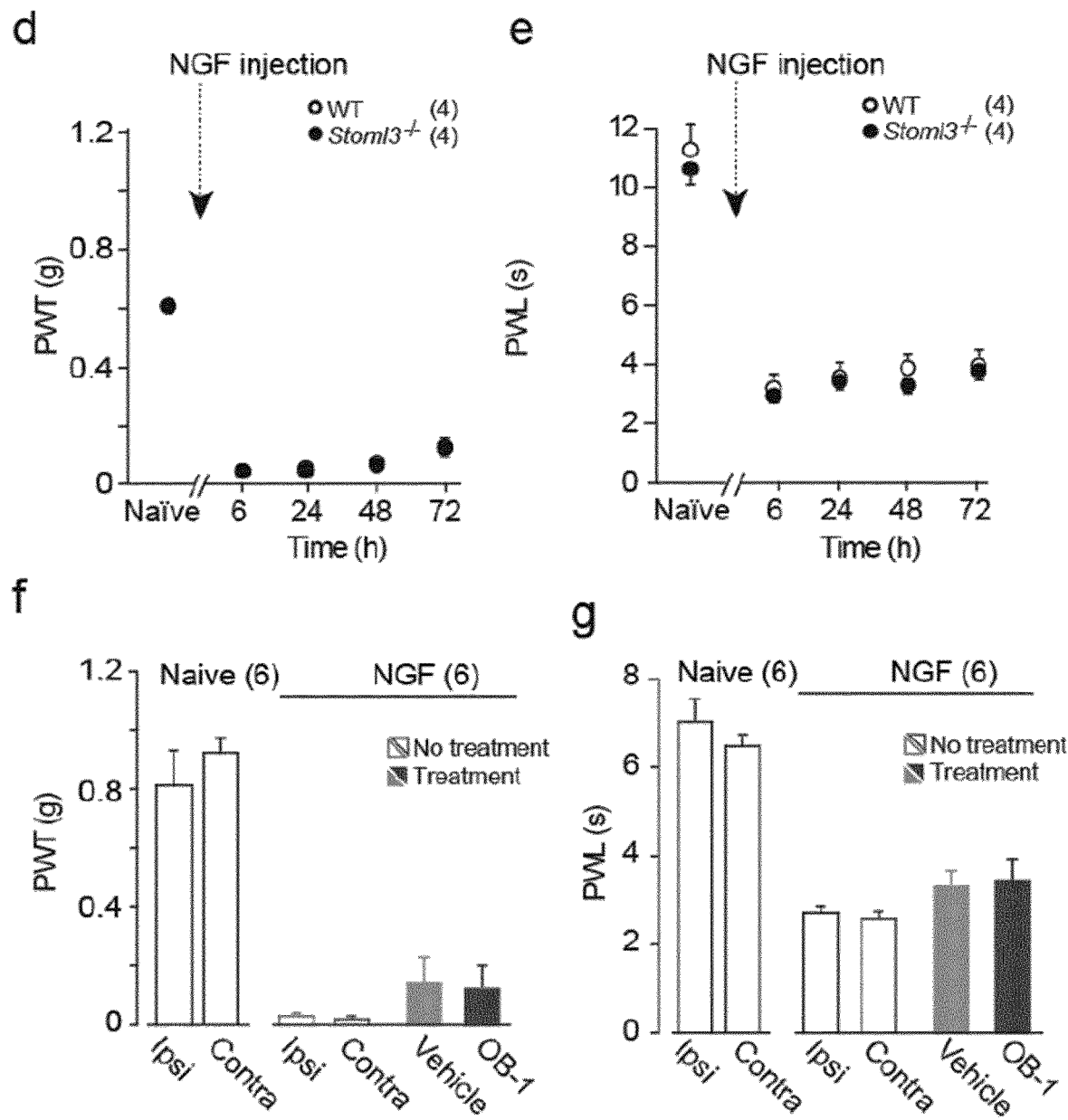

The CCI model involves direct damage to the axons that innervate the hypersensitive skin, in this case the plantar hindpaw[31]. Neuropathic touch hypersensitivity is also induced in the same skin area by cutting adjacent nerves to the tibial nerve that innervates the plantar foot[32,33]. Spared tibial nerve injury (SNI) mice develop a long lasting hypersensitivity of similar magnitude to that observed following CCI (FIG. 14a). Administration of OB-1 to the plantar skin in the SNI model produced no reversal of allodynia (FIG. 14b). We removed the lumbar DRGs from these animals and found no change in the levels of Stoml3 mRNA between the injured and uninjured side in this model (FIG. 14c). This finding suggests that the effects of OB-1 in alleviating mechanical hypersensitivity may in part depend on whether STOML3 levels are up-regulated.

Mechanical hyperalgesia is also a prominent feature in inflammatory pain, which is largely dependent on increased nerve growth factor (NGF) levels[34]. Systemic dosing with NGF (1 mg/kg) is sufficient to provoke long-lasting mechanical and heat hyperalgesia[34,35], which were both unchanged in NGF-injected Stoml3$^{-/-}$ mice (FIG. 14d,e). Additionally, mechanical hypersensitivity after NGF was also not reversed by local intraplantar OB-1 (FIG. 14f,g). This data is consistent with the prevailing view that NGF-dependent cutaneous mechanical hyperalgesia is primarily driven by central sensitization[34,36].

Regulation of Stoml3 mRNA and Protein after Injury

Figure 15:
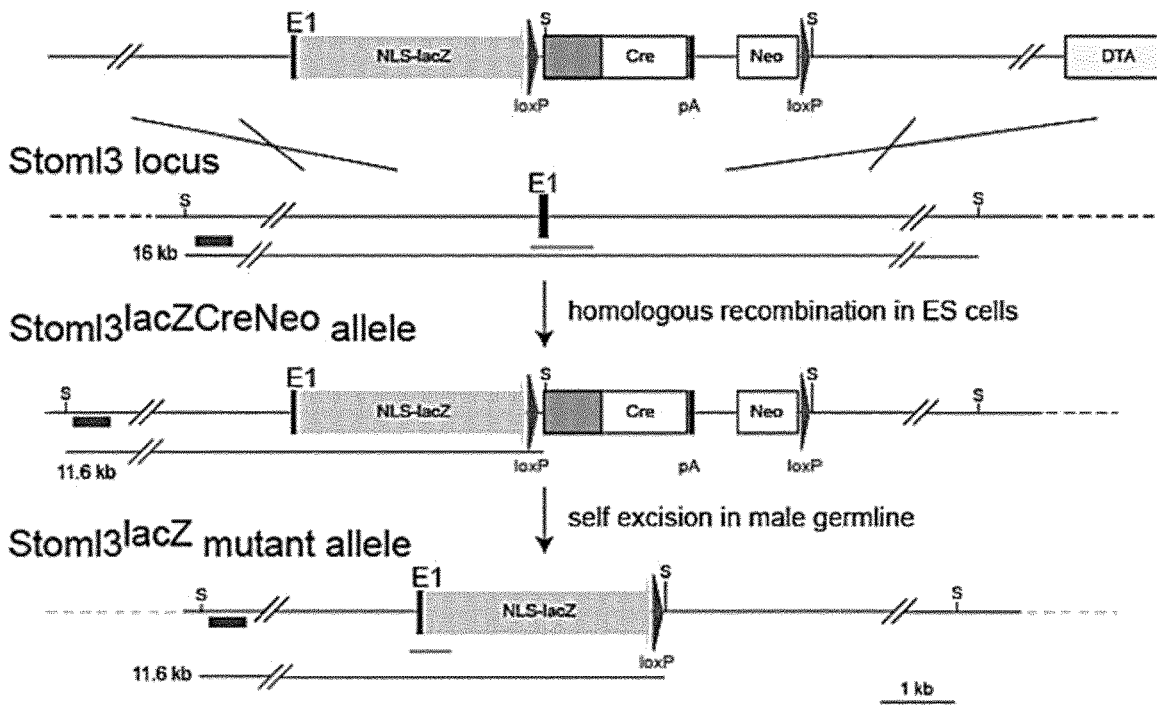
FIG. 15: Generation of the Stoml3LacZ and Stoml3Strep mouse strains. (a) Schematic representation of the targeting vector, the wild-type Stoml3 locus, and the mutated Stoml3LacZ allele, before and after removal of the self-excision neomycin (cre, neo) cassette. A 12 kb genomic region of Stoml3 locus containing exon 1 (E1, black), NLS-LacZ (blue), DTA (yellow), the self-excision neomycin cassette, loxP (red arrowhead), and SpeI (S) restriction sites are depicted. Green lines indicate the predicted fragment sizes obtained after SpeI digestion of genomic DNA. A green bar shows the 5' sequence used as a probe for Southern blot analyses shown in B. Blue lines indicate the predicted fragment sizes obtained by genotyping the tail genomic DNA as shown in C. (b) Southern blot analysis of SpeI digested tail genomic DNA from Stoml3+/LacZ and wild type mice. (c) Genotyping analysis of tail genomic DNA from Stoml3+/LacZ, wild type, and Stoml3LacZ/LacZ mice. Stoml3-LacZ F and LacZ int R primers amplified a 649 bp fragment from the Stoml3LacZ mutant allele. Stoml3-LacZ F and Stoml3-LacZ R primers amplified a 875 bp fragment from the Stoml3 wild type allele, M: 100 bp ladder (Invitrogen). (d) Schematic representation of the targeting vector, the wild-type Stoml3 locus, and the mutated Stoml3Strep allele, before and after removal of the neomycin (neo) cassette. A 12 kb genomic region of Stoml3 locus containing exon 1 (E1, black), Strep-TagII (red), DTA (yellow), the neomycin cassette (neo), loxP (blue arrowhead), and SpeI (S) restriction sites are depicted. Green lines indicate the predicted fragment sizes obtained after SpeI digestion of genomic DNA. A green bar shows the 5' sequence used as a probe for Southern blot analyses shown in E. Blue lines indicate the predicted fragment sizes obtained by genotyping the tail genomic DNA as shown in F. (e) Southern blot analysis of SpeI digested tail genomic DNA from Stoml3+/Strep and wild type mice. (f) Genotyping analysis of tail genomic DNA from wild type, Stoml3+/StrepII, and Stoml3StrepII/StrepII mice. Stoml3-Strep F and Stoml3-Strep R2 primers amplified a 321 bp fragment from the Stoml3StrepII mutant allele. Stoml3-Strep F and Stoml3-Strep R1 primers amplified a 438 bp fragment from the Stoml3 wild type allele, M: 100 bp ladder (Invitrogen).
Figure 15:
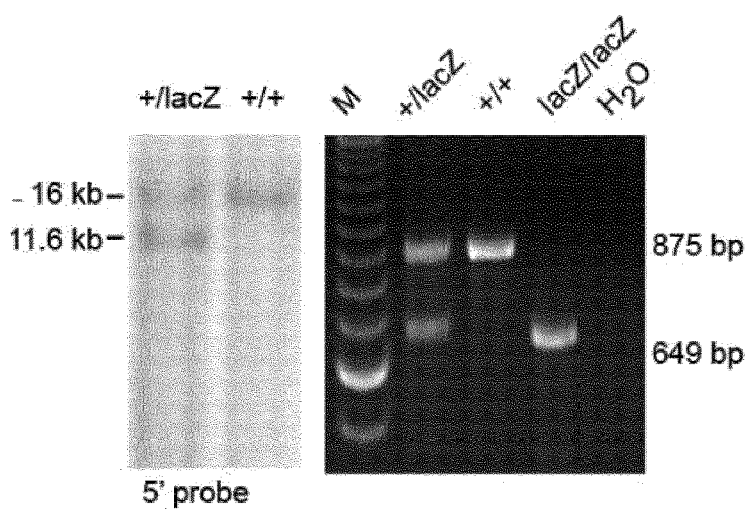
Figure 15:
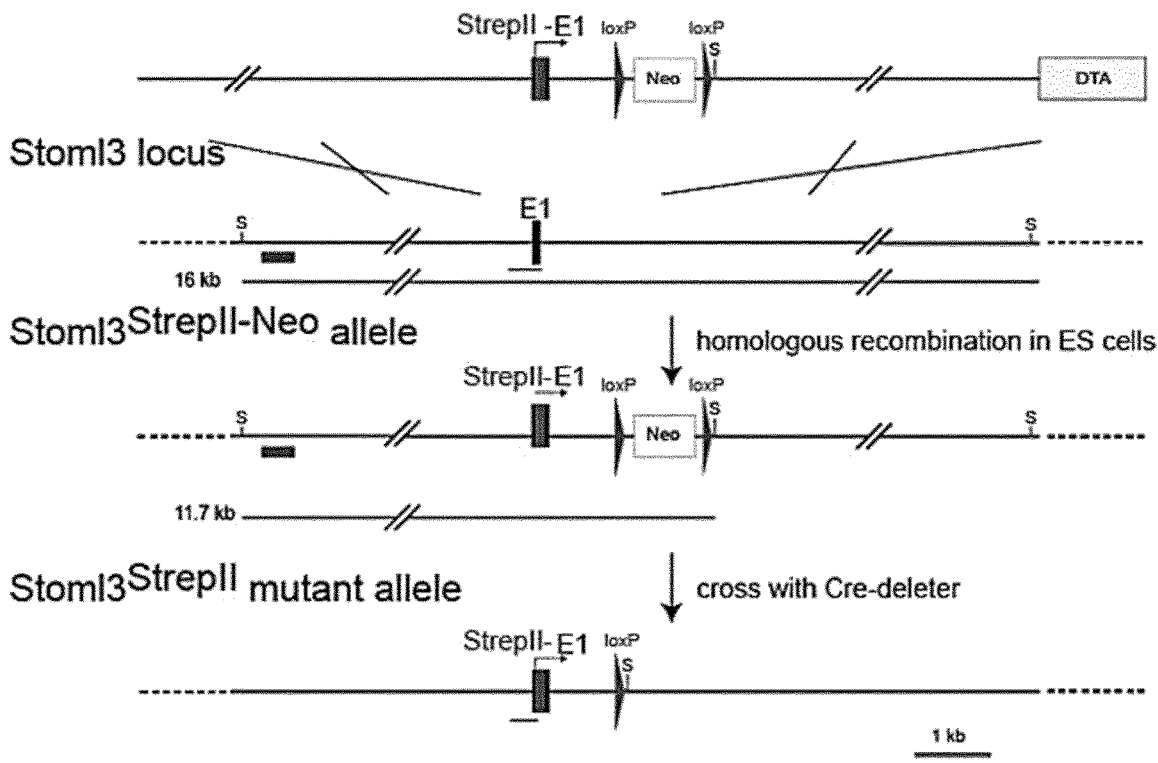
Figure 15:
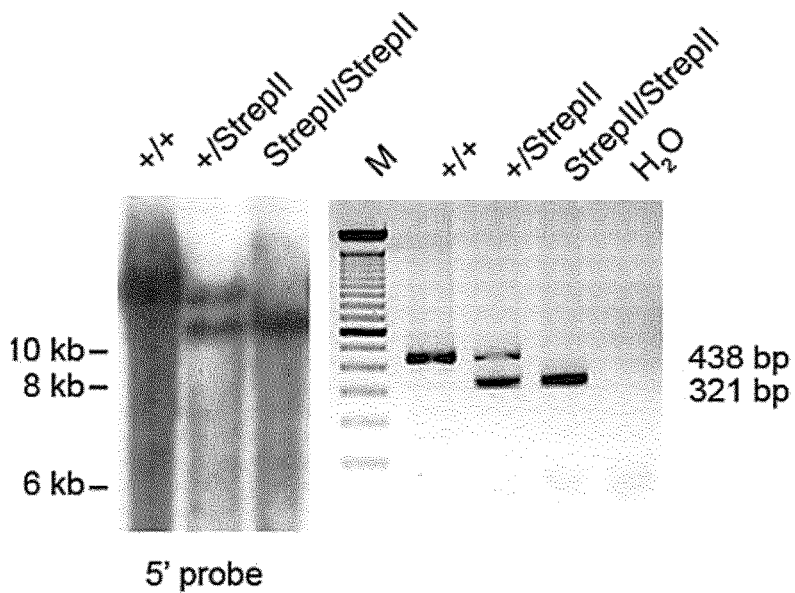

The levels of Stoml3 mRNA are very low in the DRG and we have never found an antibody that is sensitive or specific enough to detect endogenous STOML3. We therefore generated two new knock-in mouse models to monitor in the first case Stoml3 gene expression and in the second case STOML3 protein. Thus, we generated a knockin allele in which a β-galactosidase cassette with a nuclear localization signal (NLS) was fused in frame with the start codon of the Stoml3 gene (Stoml3$^{lacZ}$ mice) (FIG. 15a-c). This reporter allele allowed us to visualize subsets of sensory neurons that express Stoml3 (FIG. 6a). We observed lacZ staining in around half of sensory neurons with cell bodies >20 μm in diameter, a population known to consist of mechanoreceptors (FIG. 6a). The number of lacZ-positive neurons more than doubled in the L6-L4 ganglia after a unilateral CCI challenge and the cells were predominantly >20 μm in diameter, Fisher's exact test, p<0.0001 (FIG. 6b). This data is consistent with the idea that chronic nerve constriction leads to an increase in the number of large and medium sized sensory neurons that express higher levels of Stoml3. Consistent with our observation that Stoml3 mRNA levels are very low in the DRG, the LacZ-positive cells were difficult to visualize when screening for β-galactosidase activity and antibodies directed against the β-galactosidase protein did not give us any positive staining.

In the second knock-in mouse we introduced nucleotides encoding the StrepII tag[37] 3' to the start codon (FIG. 6c, FIG. 15d-f). The genomic fusion was successful as we could amplify Stoml3 mRNA transcripts containing the nucleotide sequence encoding an N-terminally StrepII-tagged Stoml3. We carried out Western blotting for the StrepII-tagged protein in Stoml3$^{StrepII}$ CCI mice and extracted protein from sciatic nerve at day 2, day 6 and day 13 post-injury. We could detect a specific band (absent in Stoml3$^{-/-}$ nerve) of the appropriate molecular weight in protein extracts from the sciatic nerve, but only after using a strong denaturing buffer containing 8M urea (FIG. 6d). We could sometimes detect the StrepII-STOML3 band from extracts made from DRG but this was much weaker and less reliable. Notably, we found more intense StrepII-STOML3 positive bands on the injured side at day 2, day 6 and to a lesser extent at day 13 compared to the non-injured contralateral nerve (FIG. 6d). The fact that the neuronal marker PGP9.5 band, dramatically decreased in intensity on the injured side several days after injury, probably reflects axon loss and atrophy, but despite this STOML3 levels were increased. These results suggest that endogenous STOML3 is transported preferentially to the peripheral endings of sensory neurons[38] to modulate mechanotransduction and that there is more STOML3 transported to sensory endings after traumatic nerve injury.

Figure 16:
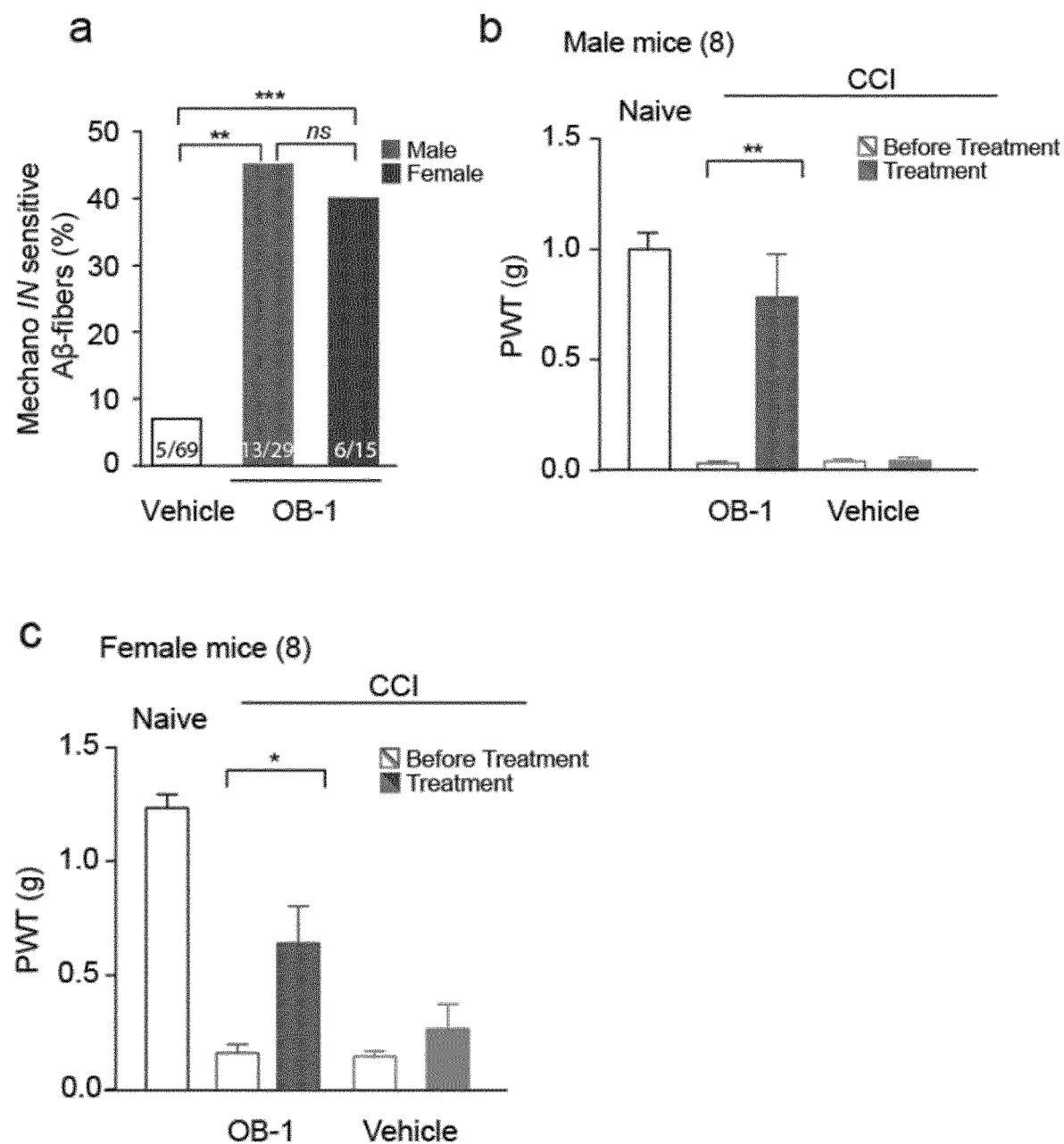
FIG. 16: Behavioral and electrophysiological measurements in female mice. (a) An electrical search protocol was used in order to trace electrically identified units to their receptive fields. Proportions of mechanolNsensitive Aβ-fibers are found to be almost identical in female mice as in male mice, (p<0.01 *p<0.001; Fisher's exact test; numbers indicate fibers recorded. (b, c) Paw withdrawal thresholds (PWT) to varying forces of von Frey filaments before and after nerve injury were measured showing that OB-1 reversed mechanical hypersensitivity to a similar extent female mice as in male mice, (*p<0.05;**p<0.01; Mann-Whitney U test; Wilcoxon Signed Rank Test; numbers indicate mice treated; data are displayed as mean of individual median PWTs; error bars indicate s.e.m.).

Recent reports have indicated that the central mechanisms of nerve injury associated hypersensitivity in male and female rodents differ[39]. Most of our behavioral and electrophysiological measurements were made in male mice but we found that an almost identical proportion of OB-1 treated Aβ-fibers were insensitive to mechanical stimuli in female mice as in male mice (FIG. 16a). Treatment of the paws of female mice with CCI with OB-1 also reversed mechanical hypersensitivity to a similar extent to that seen in males (FIG. 16b,c).

STOML3 and Painful Diabetic Neuropathy

Figure 7:
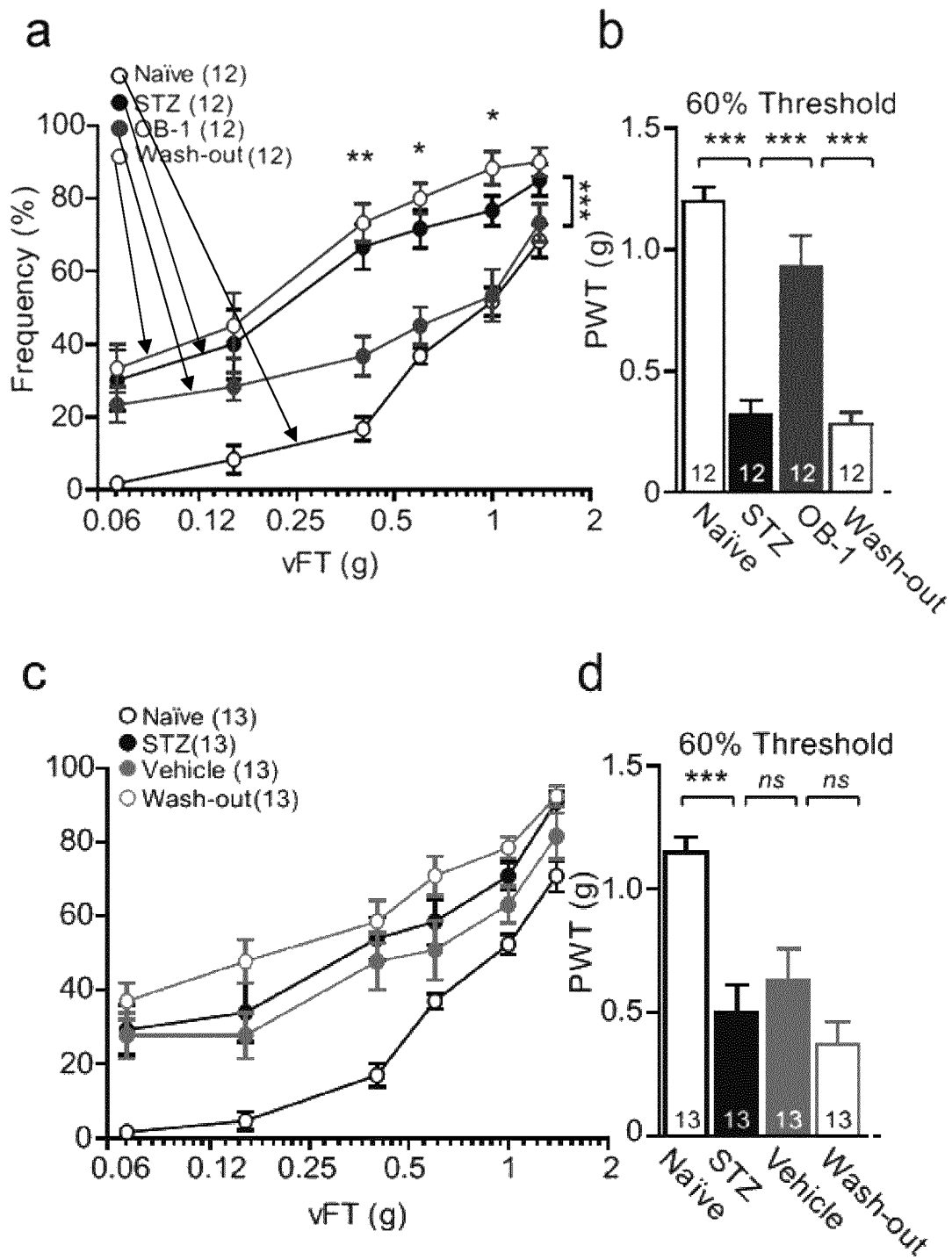
FIG. 7: Inhibition of STOML3 alleviates painful diabetic neuropathy. a, Diabetic peripheral neuropathy was induced using streptozotocin (STZ). After development of peripheral neuropathy, diabetic mice received a single injection of OB-1 or vehicle respectively into the plantar surface of the hind paw. a, Three hours after injection, OB-1 treated mice showed attenuated mechanical sensitivity displayed as percentage of withdrawal to increasing von Frey filaments (*$p<0.001$; Two-way ANOVA OB-1 vs STZ; numbers indicate mice treated; data are displayed as mean of individual PWTs; error bars indicate s.e.m.) or b, mechanical thresholds required to elicit 60% withdrawal frequency ($p<0.01$, ***$p<0.001$; Wilcoxon Signed Rank Test; paired t-test; numbers indicate mice treated; data are displayed as mean of individual PWTs; error bars indicate s.e.m.). c,d, Diabetic mice in the vehicle treated group showed no reversal of mechanical hypersensitivity (numbers indicate mice treated; data are displayed as mean of individual PWTs; error bars indicate s.e.m.).

Neuropathy is a prominent symptom of diabetes, and is often characterized by pain initiated by normally innocuous tactile stimulation in up to 20% of all patients[40]. We next asked whether OB-1 shows efficacy in a mouse model of painful diabetic neuropathy. We used the streptozotocin model (STZ) to induce mechanical hypersensitivity in mice with diabetes[41]. Between 6-7 weeks after STZ treatment, mice assigned to the drug and vehicle group began to display hypersensitivity to mechanical stimuli as reflected in increased frequency of paw withdrawal to von Frey filaments below 0.5 g (FIG. 7a-d). Local treatment of the hindpaw glabrous skin with OB-1 (250 pmol per paw) substantially reversed the mechanical hypersensitivity 4 h after treatment whereas vehicle treatment was without effect (FIG. 7a-d). The mechanical hypersensitivity returned to pre-drug treatment levels 24 h after a single treatment, as assessed by the mean 60% withdrawal threshold (FIG. 7a,b).

TriGFP Assay for Validation of Derivatives

We identified three novel STOML3 inhibitors structurally related to OB-1 using a protein-protein interaction assay based on the tripartite association between two twenty amino-acid long GFP tags, GFP10 and GFP11, which were fused to hsSTOML3 protein partners, and the complementary GFP1-9 detector (Reference 50). In this assay, N2a cells were co-transfected with plasmids encoding GFP1-9, STOML3-GFP10 and STOML3-GFP11 and incubated with either vehicle (0.4% DMSO) or OB-1 derivatives at 20 μM final concentration for 16 h. Twenty-four hours after transfection cells were collected, fixed with 4% PFA and resuspended in PBS. GFP signal intensity was measured using flow cytometry technology showing that derivatives of OB-1 strongly reduce hsSTOML3 self-association resulting in substantially lower GFP signal intensity compared to vehicle treated cells (FIG. 17).

Discussion of the Results

Mammalian touch sensation is beginning to be unraveled at the molecular level[42,43]. Mechanosensitive ion channels, like Piezo1 and Piezo2, may prove difficult targets to exploit for pharmacological intervention[44]. For example, the early embryonic or post-natal lethality associated with Piezo1 or Piezo2 gene deletion[45,46] and Piezo2's role in proprioception[47] could prove problematic for the development of Piezo antagonists for therapeutic purposes.

Figure 3:
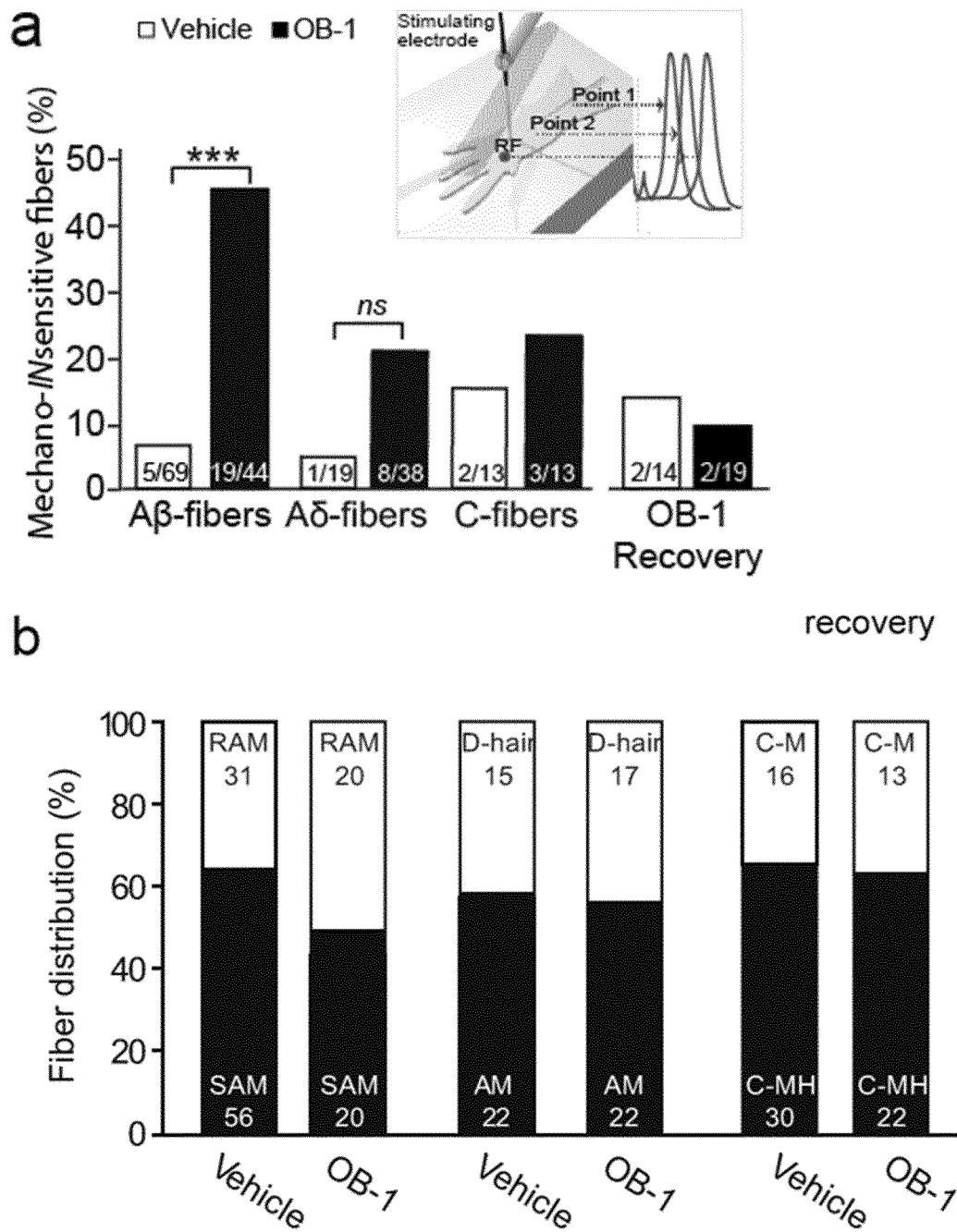
FIG. 3: Mechanoreceptors can be silenced with local OB-1 treatment. a, Electrical search protocol schema. A micro electrode (~1MΩ) was used to deliver electrical stimuli at two distant points of the saphenous nerve trunk in order to trace electrically identified units to their receptive fields. Proportions of mechanoINsensitive fibers are shown. Three hours after local OB-1 treatment (250-500 pmol OB-1 per paw) an increase in mechanically INsensitive Aβ-fibers was observed; note that mechanosensitivity had recovered 24 h post-injection. (***$p<0.001$; Fisher's exact test; numbers indicate fibers recorded). b, The proportion of each class of mechanosensitive afferents is displayed. No significant differences were observed in the proportions of receptor types in Aβ-Aδ- and C-fibers. c, Stimulus response function of C-MH fibers is shown using a series of ascending displacements (32-1024 μm). C-MH fibers were significantly less responsive in OB-1 treated mice compared to vehicle treated controls (*$p<0.05$, Two-way ANOVA; numbers indicate fibers recorded data are displayed as mean number of action potentials±s.e.m.). d, Mean force thresholds for C-MH fiber discharge are displayed showing a significant elevation of mechanical thresholds (*$p<0.05$; Mann-Whitney U test; data are displayed as individual thresholds and mean threshold±s.e.m.). e, For CM fibers stimulus response functions were not different in vehicle and OB-1 skin (Two-way ANOVA). f, Mean force thresholds for C-M fiber were also not different between vehicle and OB-1 treatments (Mann-Whitney U test).
Figure 3:
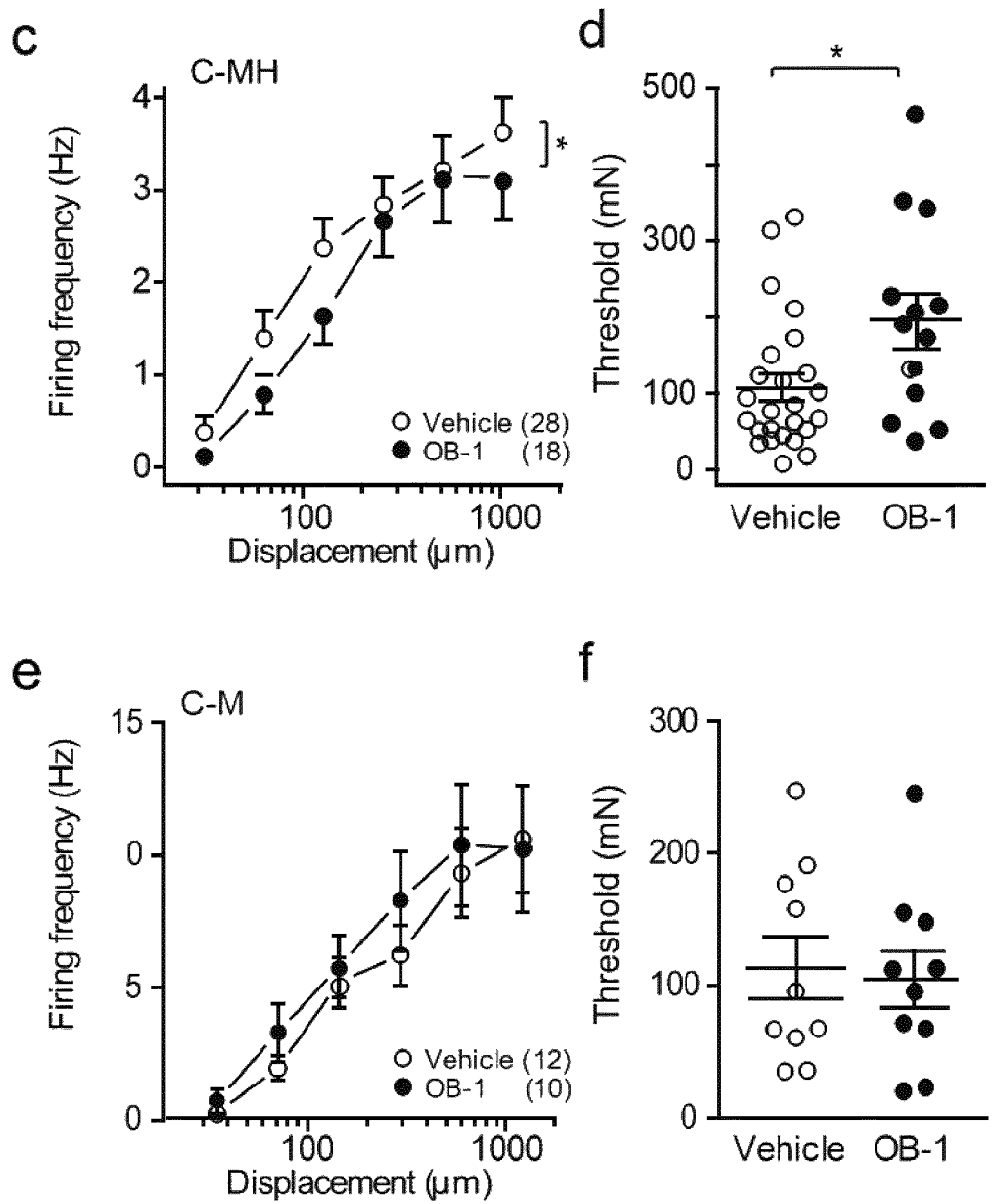
Figure 6:
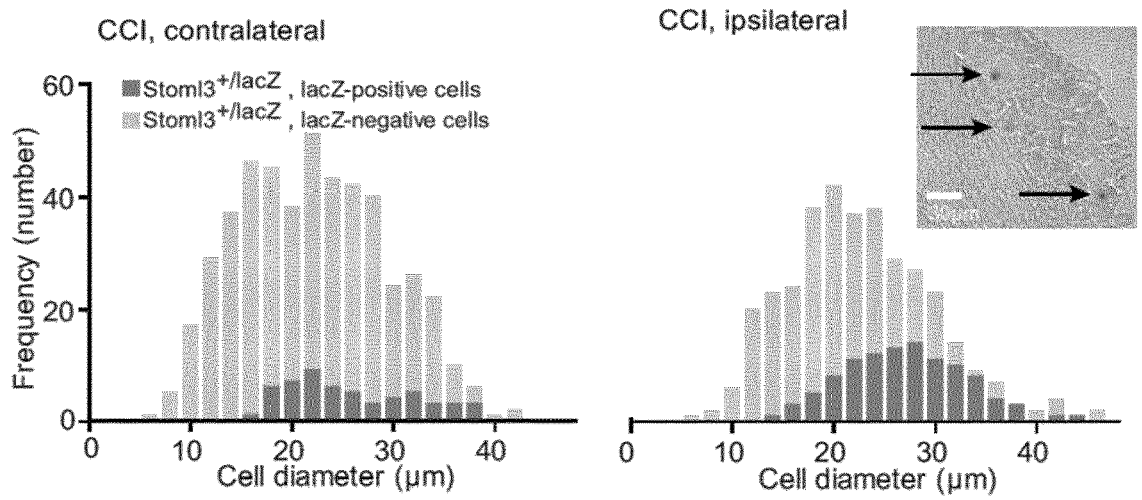
FIG. 6: Regulation of STOML3 in painful neuropathy. a, Cytochemistry of lumbar DRGs from Stoml3+/lacZ mice that had received a nerve injury (CCI). b, Note that the number of lacZ-positive neurons increased after a unilateral CCI predominantly in large cells (***$p<0.001$; Fisher's exact test; numbers indicate cells counted). c, schematic of the modified locus of StrepII knockin mice. d, Western blots of protein extracts taken from the sciatic nerve of Stoml3StrepII/StrepII knockin mice subjected to unilateral CCI. Extracts were made from two mice per time point note that a specific StrepII-STOML3 band was detected ipsilateral and contralateral to the injury at all time points (bands are not detected in protein extracts from sciatic nerves of Stoml3−/− mice). At day 2 (d2), day 6 (d6) and to a lesser extent day 13 (d13) post-injury there was clearly much more protein found on the injured side compared to the uninjured sciatic nerve. The same protein extracts were probed with antibodies against PGP9.5 a neuronal marker which decreased dramatically on the injured side consistent with the known loss and atrophy of axons in the CCI model.
Figure 6:
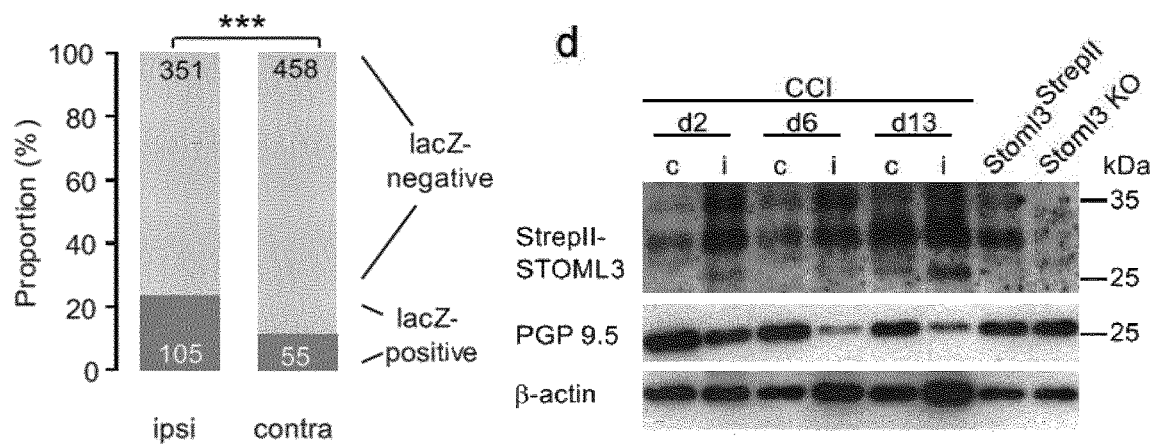
Figure 6:
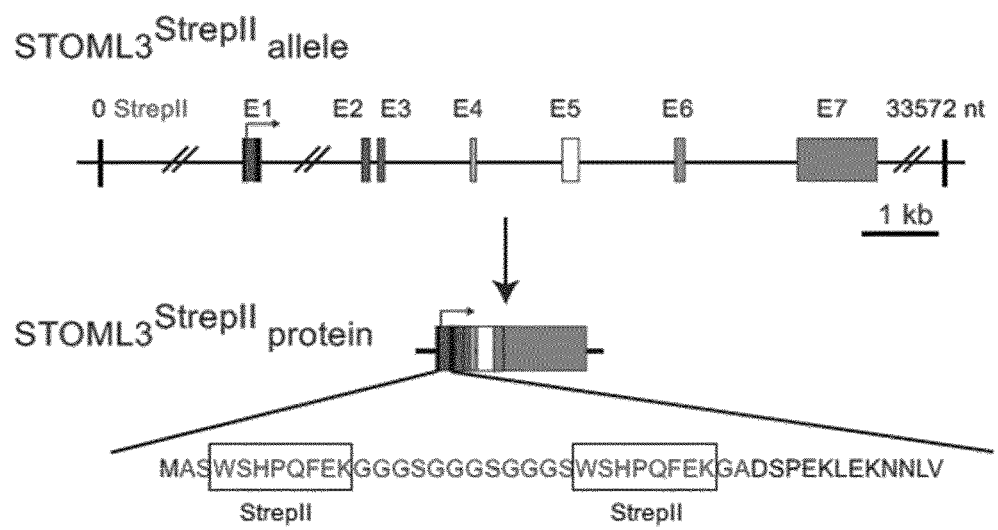

The present invention describes an intersectional approach to modulate sensory mechanotransduction, as the compounds described herein are preferably effective in cells in which both STOML3 and Piezo channels are present. This approach has the advantage that essential functions of Piezo proteins will not be directly affected by the compounds described herein, yet we can gain selective and powerful inhibition of sensory mechanotransduction, especially under certain pathophysiological conditions. We show that OB-1 has a powerful silencing effect on around 40% of mechanoreceptors and conclude that the transformation of the mechanical stimulus into receptor potential is severely impaired in these cells. Mechanosensitive currents were also inhibited by OB-1 in some nociceptors in our in vitro studies (FIG. 2f) and consistent with this mechanical thresholds were significantly elevated in many cutaneous C-fibers using the ex vivo skin-nerve preparation (FIG. 3). We propose that STOML3 inhibition silences mechanoreceptors primarily by reducing the displacement sensitivity of Piezo2 ion channels in mechanoreceptors. Mechanically gated currents in nociceptors may not be dependent on Piezo2[4], but deep sequencing studies have detected Piezo1 transcripts in many single mouse sensory neurons[48] and Piezo1 channels are also strongly modulated by STOML3[2]. Skin application of the STOML3 inhibitor OB-1 shows remarkable efficacy in reducing touch-evoked pain behavior in two mouse models of neuropathic pain. There is direct damage to the axons that innervate the sensitized skin in the CCI model that is associated with increased Stoml3 expression as well as increased STOML3 protein transport to the periphery (FIG. 6). Thus, we speculate that the remarkable efficacy of OB-1 in pain models, including painful diabetic neuropathy is directly linked to changes in STOML3 availability at sensory endings during disease progression. In summary, the present invention provides validation of novel pharmacological agents to modulate sensory mechanotransduction to treat sensory disorders, including pain.

TABLE 1

Lack of effect of OB-1 on action potential properties in dissociated mouse DRG neurons:

|  | Neuron Type | Vrest (mV) | APamp (mV) | AHP (mV) | APtime (ms) | Tpeak (ms) | Trep (ms) | Threshold (pA) | Input R (MΩ) |
|---|---|---|---|---|---|---|---|---|---|
| Vehicle | Nociceptors (n = 13) | −57.1 ± 1.6 | 118.7 ± 2.3 | −66.2 ± 1.3 | 10.0 ± 1.6 | 3.5 ± 1.5 | 6.5 ± 0.5 | 858.3 ± 231.3 | 86.2 ± 15.6 |
| OB-1 | Nociceptors (n = 12) | −59.5 ± 1.2 | 115.4 ± 4.0 | −67.4 ± 1.3 | 10.0 ± 1.5 | 5.0 ± 0.7 | 5.0 ± 1.1 | 1276.4 ± 256.0 | 56.7 ± 5.2 |
|  | P Value | 0.31 | 0.47 | 0.49 | 1 | 0.32 | 0.46 | 0.31 | 0.22 |
| Vehicle | Mechanoreceptors (n = 7) | −58.0 ± 2.2 | 102.1 ± 8.7 | −67.0 ± 1.7 | 6.7 ± 1.2 | 4.3 ± 0.9 | 2.4 ± 0.5 | 1012.9 ± 287.0 | 80.4 ± 26.5 |
| OB-1 | Mechanoreceptors (n = 9) | −56.6 ± 2.0 | 97.8 ± 4.9 | −62.3 ± 1.6 | 11.90 ± 2.9 | 7.5 ± 2.0 | 4.5 ± 1.7 | 700.0 ± 305.9 | 40.8 ± 6.7 |
|  | P Value | 0.68 | 0.35 | 0.06 | 0.23 | 0.19 | 0.46 | 0.35 | 0.22 |

Vrest (Resting potential), APamp (action potential amplitude), AHP (after-hyperpolarization potential), APtime (total duration of action potential), Tpeak (Time to action potential peak), Trep (Time to repolarizing peak).
All data presented as mean ± s.e.m.

REFERENCES

1. Bensmaia, S. J. Tactile intensity and population codes. Behav. Brain Res. 190, 165-173 (2008).
2. Poole, K., Herget, R., Lapatsina, L., Ngo, H.-D. & Lewin, G. R. Tuning Piezo ion channels to detect molecular-scale movements relevant for fine touch. Nat. Commun. 5, 3520 (2014).
3. Woo, S.-H. et al. Piezo2 is required for Merkel-cell mechanotransduction. Nature (2014). doi:10.1038/nature13251
4. Ranade, S. S. et al. Piezo2 is the major transducer of mechanical forces for touch sensation in mice. Nature 516, 121-125 (2014).
5. Moshourab, R. A., Wetzel, C., Martinez-Salgado, C. & Lewin, G. R. Stomatin-domain protein interactions with acid-sensing ion channels modulate nociceptor mechanosensitivity. J. Physiol. 591, 5555-5574 (2013).
6. Wetzel, C. et al. A stomatin-domain protein essential for touch sensation in the mouse. Nature 445, 206-209 (2007).
7. Costigan, M., Scholz, J. & Woolf, C. J. Neuropathic pain: a maladaptive response of the nervous system to damage. Annu. Rev. Neurosci. 32, 1-32 (2009).
8. von Hehn, C. A., Baron, R. & Woolf, C. J. Deconstructing the Neuropathic Pain Phenotype to Reveal Neural Mechanisms. Neuron 73, 638-652 (2012).
9. Tal, M. & Bennett, G. J. Extra-territorial pain in rats with a peripheral mononeuropathy: mechano-hyperalgesia and mechano-allodynia in the territory of an uninjured nerve. Pain 57, 375-382 (1994).
10. Brand, J. et al. A stomatin dimer modulates the activity of acid-sensing ion channels. EMBO J. 31, 3635-3646 (2012).
11. Poole, K. et al. Tuning Piezo ion channels to detect molecular-scale movements relevant for fine touch. Nat. Commun. 5, 3520 (2014).
12. Wang, Y. & Morrow, J. S. Identification and characterization of human SLP-2, a novel homologue of stomatin (band 7.2b) present in erythrocytes and other tissues. J. Biol. Chem. 275, 8062-8071 (2000).
13. Boute, N. et al. NPHS2, encoding the glomerular protein podocin, is mutated in autosomal recessive steroid-resistant nephrotic syndrome. Nat. Genet. 24, 349-354 (2000).
14. Mairhofer, M., Steiner, M., Salzer, U. & Prohaska, R. Stomatin-like protein-1 interacts with stomatin and is targeted to late endosomes. J. Biol. Chem. 284, 29218-29229 (2009).
15. Da Cruz, S. et al. SLP-2 interacts with prohibitins in the mitochondrial inner membrane and contributes to their stability. Biochim. Biophys. Acta 1783, 904-911 (2008).
16. Lapatsina, L., Brand, J., Poole, K., Daumke, O. & Lewin, G. R. Stomatin-domain proteins. Eur. J. Cell Biol. 91, 240-245 (2012).

17. Hu, C.-D., Chinenov, Y. & Kerppola, T. K. Visualization of interactions among bZIP and Rel family proteins in living cells using bimolecular fluorescence complementation. *Mol. Cell* 9, 789-798 (2002).
18. Heilemann, M. et al. Subdiffraction-resolution fluorescence imaging with conventional fluorescent probes. *Angew. Chem. Int. Ed. Engl.* 47, 6172-6176 (2008).
19. Lampe, A., Haucke, V., Sigrist, S. J., Heilemann, M. & Schmoranzer, J. Multi-colour direct STORM with red emitting carbocyanines. *Biol. Cell* 104, 229-237 (2012).
20. Wolter, S. et al. rapidSTORM: accurate, fast open-source software for localization microscopy. *Nat. Methods* 9, 1040-1041 (2012).
21. Hu, J. & Lewin, G. R. Mechanosensitive currents in the neurites of cultured mouse sensory neurones. *J. Physiol.* 577, 815-828 (2006).
22. McCarter, G. C., Reichling, D. B. & Levine, J. D. Mechanical transduction by rat dorsal root ganglion neurons in vitro. *Neurosci. Lett.* 273, 179-182 (1999).
23. Price, M. P., Thompson, R. J., Eshcol, J. O., Wemmie, J. A. & Benson, C. J. Stomatin modulates gating of acid-sensing ion channels. *J. Biol. Chem.* 279, 53886-53891 (2004).
24. Kozlenkov, A., Lapatsina, L., Lewin, G. R. & Smith, E. S. J. Subunit-specific inhibition of acid sensing ion channels by stomatin-like protein 1. *J. Physiol.* 592, 557-569 (2014).
25. Milenkovic, N., Wetzel, C., Moshourab, R. & Lewin, G. R. Speed and temperature dependences of mechanotransduction in afferent fibers recorded from the mouse saphenous nerve. *J. Neurophysiol.* 100, 2771-2783 (2008).
26. Lewin, G. R. & Moshourab, R. Mechanosensation and pain. *J. Neurobiol.* 61, 30-44 (2004).
27. Beggs, S., Trang, T. & Salter, M. W. P2X4R+ microglia drive neuropathic pain. *Nat. Neurosci.* 15, 1068-1073 (2012).
28. Chaplan, S. R., Bach, F. W., Pogrel, J. W., Chung, J. M. & Yaksh, T. L. Quantitative assessment of tactile allodynia in the rat paw. *J. Neurosci. Methods* 53, 55-63 (1994).
29. Baron, R. Neuropathic pain: a clinical perspective. *Handb. Exp. Pharmacol.* 3-30 (2009). doi:10.1007/978-3-540-79090-7_1
30. Dworkin, R. H. et al. Recommendations for the pharmacological management of neuropathic pain: an overview and literature update. *Mayo Clin. Proc.* 85, S3-14 (2010).
31. Basbaum, A. I., Gautron, M., Jazat, F., Mayes, M. & Guilbaud, G. The spectrum of fiber loss in a model of neuropathic pain in the rat: an electron microscopic study. *Pain* 47, 359-67 (1991).
32. Decosterd, I. & Woolf, C. J. Spared nerve injury: an animal model of persistent peripheral neuropathic pain. *Pain* 87, 149-158 (2000).
33. Shields, S. D., Eckert, W. A. & Basbaum, A. I. Spared nerve injury model of neuropathic pain in the mouse: a behavioral and anatomic analysis. *J. Pain Off. J. Am. Pain Soc.* 4, 465-470 (2003).
34. Lewin, G. R., Lechner, S. G. & Smith, E. S. J. Nerve growth factor and nociception: from experimental embryology to new analgesic therapy. *Handb. Exp. Pharmacol.* 220, 251-282 (2014).
35. Lewin, G. R. et al. Nerve growth factor-induced hyperalgesia in the neonatal and adult rat. *J. Neurosci.* 13, 2136-48 (1993).
36. Lewin, G. R., Rueff, A. & Mendell, L. M. Peripheral and central mechanisms of NGF-induced hyperalgesia. *Eur. J. Neurosci.* 6, 1903-12 (1994).
37. Korndörfer, I. P. & Skerra, A. Improved affinity of engineered streptavidin for the Strep-tag II peptide is due to a fixed open conformation of the lid-like loop at the binding site. *Protein Sci.* 11, 883-93 (2002).
38. Lapatsina, L. et al. Regulation of ASIC channels by a stomatin/STOML3 complex located in a mobile vesicle pool in sensory neurons. *Open Biol.* 2, 120096 (2012).
39. Sorge, R. E. et al. Different immune cells mediate mechanical pain hypersensitivity in male and female mice. *Nat. Neurosci.* 18, 1081-1083 (2015).
40. van Hecke, O., Austin, S. K., Khan, R. A., Smith, B. H. & Torrance, N. Neuropathic pain in the general population: a systematic review of epidemiological studies. *Pain* 155, 654-662 (2014).
41. Bierhaus, A. et al. Methylglyoxal modification of Nav1.8 facilitates nociceptive neuron firing and causes hyperalgesia in diabetic neuropathy. *Nat. Med.* 18, 926-933 (2012).
42. Abraira, V. E. & Ginty, D. D. The sensory neurons of touch. *Neuron* 79, 618-639 (2013).
43. Lechner, S. G. & Lewin, G. R. Hairy sensation. *Physiology (Bethesda)*. 28, 142-150 (2013).
44. Syeda, R. et al. Chemical activation of the mechanotransduction channel Piezo1. *Elife* 4, (2015).
45. Li, J. et al. Piezo1 integration of vascular architecture with physiological force. *Nature* (2014). doi:10.1038/nature13701
46. Ranade, S. S. et al. Piezo1, a mechanically activated ion channel, is required for vascular development in mice. *Proc. Natl. Acad. Sci. U.S.A* 111, 10347-10352 (2014).
47. Woo, S.-H. et al. Piezo2 is the principal mechanotransduction channel for proprioception. *Nat. Neurosci.* 18, 1756-62 (2015).
48. Usoskin, D. et al. Unbiased classification of sensory neuron types by large-scale single-cell RNA sequencing. *Nat. Neurosci.* 18, 145-153 (2015).
49. Milenkovic, N. et al. A somatosensory circuit for cooling perception in mice. *Nat. Neurosci.* 17, 1560-1566 (2014).
50. Cabantous S, et al. A new protein-protein interaction sensor based on tripartite split-GFP association. *Sci Rep.* 2013 Oct. 4; 3:2854

The invention claimed is:

1. A method of treating pain in a subject comprising administering a compound according to Formula I to the subject,

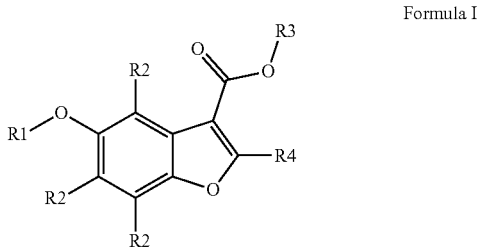

Formula I wherein
R1=5-membered aromatic heterocycle, comprising one or more of N, O and/or S, optionally substituted with $Y_x$, wherein x=0, 1, 2, 3, wherein Y can be the same or different, and wherein Y is nitro, halogen, or C1-C7 alkyl;

R2=H;

R3=H, C1-C7 alkyl;

R4=phenyl, optionally substituted with one or more halogens.

2. A method of treating pain in a subject according to claim 1, the method comprising administering a compound according to Formula II to the subject,

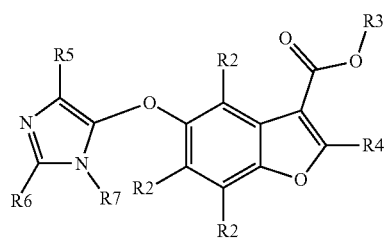

Formula II wherein

R2=H;

R3=H, C1-C7 alkyl;

R4=phenyl, optionally substituted with one or more halogens;

R5=H, nitro;

R6=H;

R7=H, C1-C7 alkyl.

3. A method of treating pain in a subject according to claim 1, the method comprising administering a compound to the subject selected from the group consisting of:

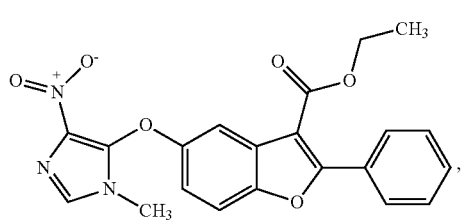

OB-1

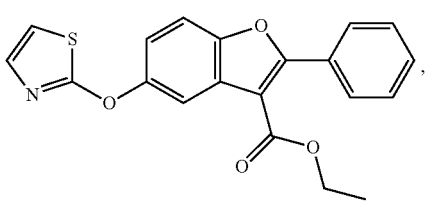

MDC-D38

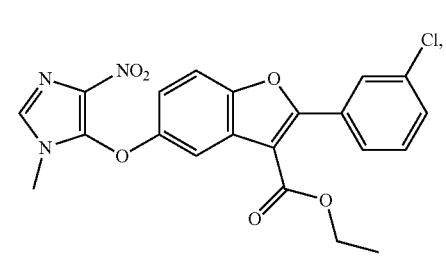

MDC-D30 Cl, and

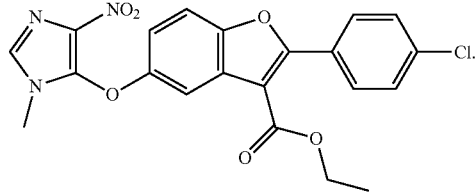

MDC-D34

4. Compound according to Formula V:

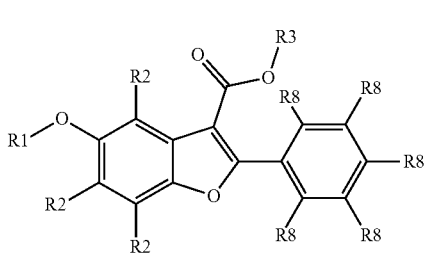

Formula V wherein

R1=5-membered aromatic heterocycle, comprising one or more of N, O and/or S, optionally substituted with Yx, wherein x=0, 1, 2, 3, wherein Y can be the same or different, and wherein Y is nitro, halogen, C1-C7 alkyl, alkoxy, optionally substituted with halogen;

R2=can be the same or different, H, halogen, C1-C7 alkyl, alkoxy;

R3=H, C1-C7 alkyl, cycloalkyl, alkoxy, aryl, optionally substituted with one or more halogens;

R8=can be the same or different, H, halogen, wherein at least one of R8 is halogen.

5. Compound according to claim 4, according to Formula V:

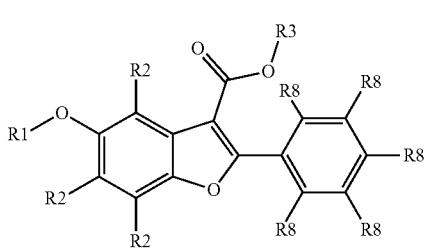

Formula V wherein

R1=5-membered aromatic heterocycle, comprising 1-2 N atoms, optionally substituted with Yx, wherein x=0, 1, 2, 3, wherein Y can be the same or different, and wherein Y is nitro, halogen, C1-C7 alkyl, optionally substituted with halogen;

R2=H,

R3=H, C1-C7 alkyl, optionally substituted with one or more halogens,

R8=can be the same or different, H, halogen, wherein at least one of R8 is halogen.

6. Compound according to claim 4, according to Formula VI:

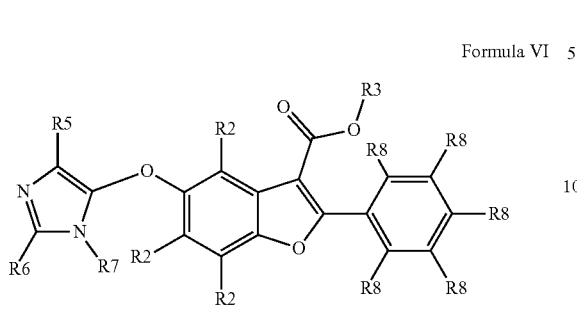

Formula VI wherein
R2=can be the same or different, H, halogen, C1-C7 alkyl, alkoxy;
R3=H, C1-C7 alkyl, cycloalkyl, alkoxy, aryl, optionally substituted with one or more halogens;
R5=H, nitro, halogen, C1-C7) alkyl, cycloalkyl, alkoxy, optionally substituted with one or more halogens;
R6=H, halogen), C1-C7 alkyl, cycloalkyl, alkoxy, optionally substituted with one or more halogens;
R7=H, C1-C7 alkyl, cycloalkyl, optionally substituted with one or more halogens,
R8=can be the same or different, H, halogen, wherein at least one of R8 is halogen.

7. Compound according to claim 4, according to Formula VI:

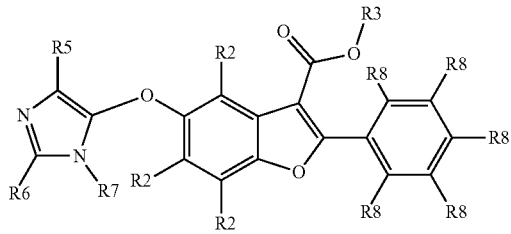

Formula VI wherein
R2=H,
R3=H, C1-C7 alkyl, optionally substituted with one or more halogens,
R5=H, nitro, halogen, C1-C7 alkyl, optionally substituted with one or more halogens;
R6=H, halogen, C1-C7 alkyl, optionally substituted with one or more halogens;
R7=H, C1-C7 (preferably C1-05 or C1-C3) alkyl, optionally substituted with one or more halogens,
R8=can be the same or different, H, halogen, wherein at least one of R8 is halogen.

8. Compound according to claim 4, according to Formula VII:

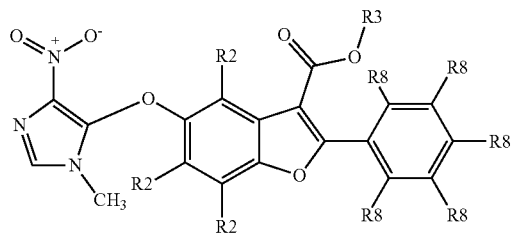

Formula VII wherein
R2=can be the same or different, H, halogen, C1-C7 alkyl, alkoxy;
R3=H, C1-C7 alkyl, cycloalkyl, alkoxy, aryl, optionally substituted with one or more halogens;
R8=can be the same or different, H, halogen, wherein at least one of R8 is halogen.

9. Compound according to claim 8,
wherein
R2=H,
R3=H, C1-C7 alkyl,
R8=can be the same or different, H, halogen 1), wherein at least one of R8 is halogen.

10. Compound according to Formula I:

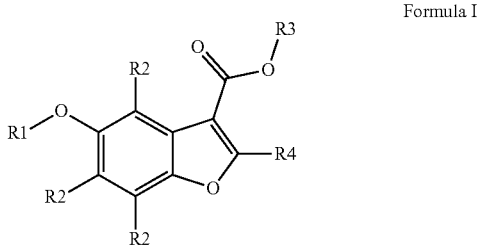

Formula I wherein
R1=5-membered aromatic heterocycle, comprising at least one N and at least one S,
R2=H,
R3=H, C1-C7 alkyl, optionally substituted with one or more halogens,
R4=aryl, optionally substituted with one or more halogens.

11. Compound according to claim 10, according to Formula VIII:

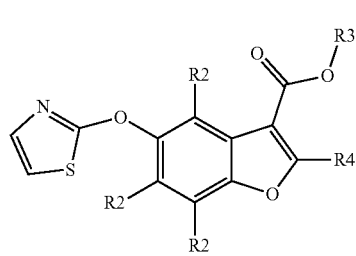

Formula VIII wherein
R2=can be the same or different, H, halogen, C1-C7 alkyl, alkoxy;
R3=H, C1-C7 alkyl, cycloalkyl, alkoxy, aryl, optionally substituted with one or more halogens;

R4=H, C1-C7 alkyl, cycloalkyl, alkoxy, aryl, optionally substituted with one or more halogens.

12. Compound according to claim 11:
wherein
R2=H,
R3=H, C1-C7) alkyl, optionally substituted with one or more halogens,
R4=H, C1-C7 alkyl, cycloalkyl, aryl, optionally substituted with one or more halogens.

13. Compound according to claim 10, according to Formula IX:

Formula IX

*[chemical structure]* wherein
R2=can be the same or different, H, halogen, C1-C7 alkyl, alkoxy;
R3=H, C1-C7 alkyl, cycloalkyl, alkoxy, aryl, optionally substituted with one or more halogens;
R8=can be the same or different, H, halogen, preferably wherein at least one of R8 is halogen.

14. Compound according to claim 13,
wherein
R2=H,
R3=H, C1-C7 alkyl, optionally substituted with one or more halogens,
R8=can be the same or different, H, halogen, preferably wherein at least one of R8 is halogen.

15. Compound according to claim 10, with a structure selected from the group consisting of:

MDC-D38

*[chemical structure]*

MDC-D30

*[chemical structure]* and

MDC-D34

*[chemical structure]*

16. A method of treating pain in a subject comprising administering a compound according to Formula III to the subject, Formula III

*[chemical structure]* wherein
X=NR6, wherein R6 is H, C1-C7 alkyl, alkoxy, optionally substituted with one or more halogens;
R1=can be the same or different, H, C1-C7 alkyl, optionally substituted with one or more halogens;
R2=5- or 6-membered carbon ring structure,
optionally aromatic, optionally substituted with $Z_x$, wherein x=0, 1, 2, 3, 4, 5, wherein Z can be the same or different, and wherein Z is selected from halogen, C1-C7 alkyl, alkoxy, wherein Z is optionally substituted with one or more halogens;
R3=can be the same or different, H, C1-C7 alkyl, optionally substituted with one or more halogens;
R4=can be the same or different, H, halogen, C1-C7 alkyl, alkoxy, optionally substituted with one or more halogens;
R5=6-membered aromatic heterocycle, comprising one or more of N, O and/or S, optionally substituted with $Z_x$, wherein x=0, 1, 2, 3, 4, 5, wherein Z can be the same or different, and wherein Z is selected from halogen, C1-C7 alkyl, alkoxy, wherein Y is optionally substituted with one or more halogens;
Y=C, N.

17. A method of treating pain in a subject according to claim 16, the method comprising administering a compound according to Formula III to the subject,
wherein
X=NR6, wherein R6 is H, C1-C7 alkyl, optionally substituted with one or more halogens;
R1=can be the same or different, H, C1-C7 alkyl, optionally substituted with one or more halogens;
R2=6-membered carbon ring structure,
optionally aromatic, optionally substituted with $Z_x$, wherein x=0, 1, 2, 3, 4, 5, wherein Z can be the same or different, and wherein Z is selected from halogen, C1-C7 alkyl, alkoxy, wherein Z is optionally substituted with one or more halogens;

R3=can be the same or different, H, C1-C7 alkyl, optionally substituted with one or more halogens;
R4=can be the same or different, H, halogen, C1-C7 alkyl, optionally substituted with one or more halogens;
R5=6-membered aromatic heterocycle, comprising one or more of N, O and/or S, optionally substituted with $Z_x$, wherein x=0, 1, 2, 3, 4, 5, wherein Z can be the same or different, and wherein Z is selected from halogen, C1-C7 alkyl, alkoxy, wherein Y is optionally substituted with one or more halogens;
Y=C, N, wherein at least one Y is N.

18. A method of treating pain in a subject according to claim 16, the method comprising administering a compound according to Formula IV to the subject,

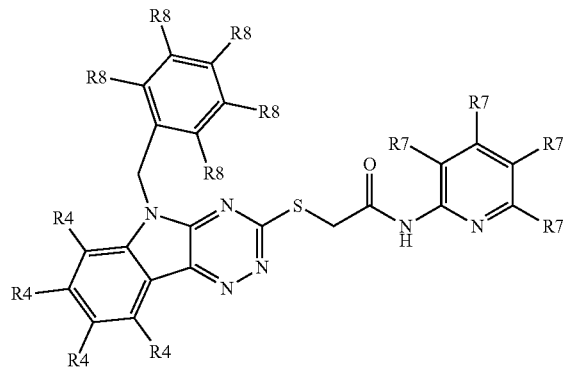

Formula IV wherein
R4=can be the same or different, H, halogen, C1-C7 alkyl, optionally substituted with one or more halogens;
R7=can be the same or different, H, halogen, C1-C7 alkyl, optionally substituted with one or more halogens;
R8=can be the same or different, H, halogen, C1-C7 alkyl, optionally substituted with one or more halogens.

19. A method of treating pain in a subject according to claim 16, the method comprising administering a compound to the subject, according to:

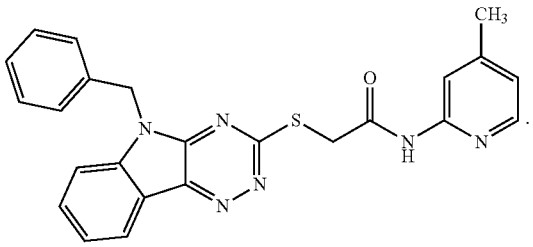

OB-2

20. A method of treating pain in a subject according to claim 1, wherein said pain is neuropathic pain.

21. A method of treating pain in a subject according to claim 1, wherein said pain is induced by and/or associated with tactile stimulation.

22. A method of treating pain according to claim 1, wherein the subject of treatment exhibits painful diabetic neuropathy.

23. A method of treating pain in a subject according to claim 1, wherein said treatment comprises topical administration of the compound.

24. A method of modulating touch perception comprising administering a compound according to claim 10, or a composition comprising said compound, to a subject.

* * * * *